(12) United States Patent
Shigeta

(10) Patent No.: US 12,702,270 B2
(45) Date of Patent: Aug. 11, 2026

(54) ENDOSCOPE SYSTEM AND METHOD FOR OPERATING THE SAME

(71) Applicant: FUJIFILM Corporation, Tokyo (JP)

(72) Inventor: Norimasa Shigeta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 233 days.

(21) Appl. No.: 18/749,519

(22) Filed: Jun. 20, 2024

(65) Prior Publication Data

US 2024/0335092 A1 Oct. 10, 2024

Related U.S. Application Data

(63) Continuation of application No. PCT/JP2022/039943, filed on Oct. 26, 2022.

(30) Foreign Application Priority Data

Dec. 22, 2021 (JP) ................................ 2021-208312
Sep. 2, 2022 (JP) ................................ 2022-139982

(51) Int. Cl.
*A61B 1/00* (2006.01)

(52) U.S. Cl.
CPC .... *A61B 1/000095* (2022.02); *A61B 1/00006* (2013.01); *A61B 1/00045* (2013.01)

(58) Field of Classification Search
CPC .......... A61B 1/000095; A61B 1/00006; A61B 1/00045; A61B 1/000094; A61B 1/0005
See application file for complete search history.

(56) References Cited

U.S. PATENT DOCUMENTS 8,825,125 B2 * 9/2014 Saito .................. A61B 5/14551 600/323
9,014,772 B2 * 4/2015 Yamaguchi .......... A61B 5/1459 600/309
9,097,589 B2 * 8/2015 Yamaguchi .......... A61B 5/0084
10,194,849 B2 * 2/2019 Otani .................. A61B 1/0646
11,478,136 B2 * 10/2022 Endo .................... A61B 5/1075
2011/0077462 A1 * 3/2011 Saitou ................. A61B 5/0059 600/109
2012/0053434 A1 * 3/2012 Saito .................... A61B 5/1459 600/324

(Continued)

FOREIGN PATENT DOCUMENTS

EP 2368480 A1 * 9/2011 ....... A61B 1/000094
EP 2474853 A2 * 7/2012 .......... A61B 5/1459

(Continued)

OTHER PUBLICATIONS

"International Search Report (Form PCT/ISA/210) of PCT/JP2022/039943," mailed on Dec. 27, 2022, with English translation thereof, pp. 1-5.

(Continued)

*Primary Examiner* — Manav Seth
(74) *Attorney, Agent, or Firm* — JCIPRNET

(57) ABSTRACT

In a correction mode, a correction image is displayed on an extension display, and a specific region is displayed on the extension display. In the correction mode, a display style control unit performs at least one of changing a display style of the correction image or changing a display style of the specific region in accordance with reliability related to calculation of the oxygen saturation.

13 Claims, 45 Drawing Sheets

(56) References Cited

U.S. PATENT DOCUMENTS

| | | | | |
|---|---|---|---|---|
| 2013/0278738 | A1* | 10/2013 | Hayashi | A61B 1/00194 348/68 |
| 2015/0238126 | A1 | 8/2015 | Saito | |
| 2017/0135555 | A1* | 5/2017 | Yoshizaki | A61B 1/00055 |
| 2018/0020903 | A1 | 1/2018 | Saito | |
| 2018/0271412 | A1* | 9/2018 | Shigeta | A61B 1/00009 |
| 2018/0317754 | A1 | 11/2018 | Yamamoto | |
| 2019/0038111 | A1* | 2/2019 | Endo | A61B 1/000094 |
| 2020/0359940 | A1 | 11/2020 | Saito | |
| 2022/0322974 | A1 | 10/2022 | Shigeta | |
| 2024/0111145 | A1* | 4/2024 | Chiba | A61B 1/05 |
| 2026/0053399 | A1* | 2/2026 | Peikon | A61B 5/0075 |

FOREIGN PATENT DOCUMENTS

| | | | | |
|---|---|---|---|---|
| EP | 2550910 | A1 * | 1/2013 | A61B 1/313 |
| EP | 2912992 | A1 * | 9/2015 | H04N 23/555 |
| EP | 3117759 | A1 * | 1/2017 | H04N 23/56 |
| JP | 6039639 | | 12/2016 | |
| JP | 2017113184 | | 6/2017 | |
| JP | 2017158782 | | 9/2017 | |
| JP | 6412252 | | 10/2018 | |
| WO | 2019155816 | | 8/2019 | |

OTHER PUBLICATIONS

"Written Opinion of the International Searching Authority (Form PCT/ISA/237) of PCT/JP2022/039943," mailed on Dec. 27, 2022, with English translation thereof, pp. 1-8.

* cited by examiner

FIG. 2
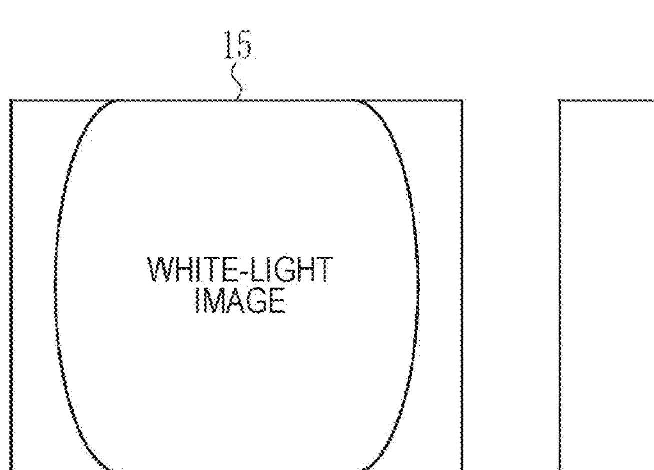
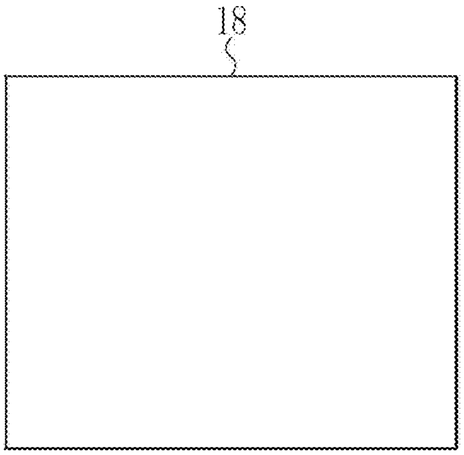
FIG. 3
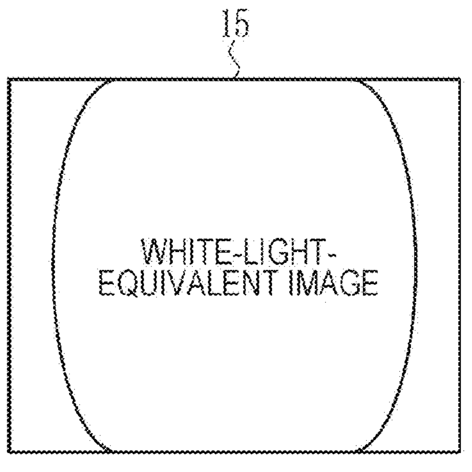
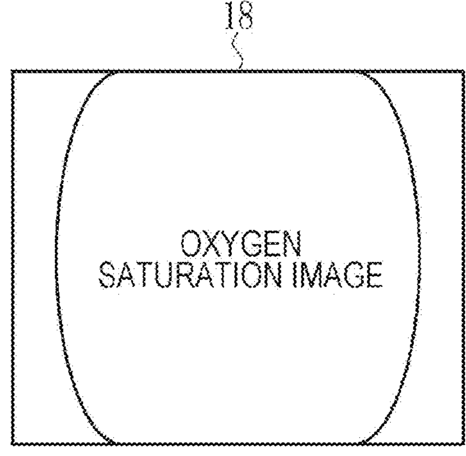

18

MS0

Please perform correction processing.

FIG. 10

| ILLUMINATION | IMAGE SIGNAL |
|---|---|
| EMISSION OF VIOLET LIGHT<br>EMISSION OF SECOND BLUE LIGHT<br>EMISSION OF GREEN LIGHT<br>EMISSION OF RED LIGHT | (Bc, Gc, Rc) |

FIG. 11

| | ILLUMINATION | IMAGE SIGNAL |
|---|---|---|
| FIRST FRAME | EMISSION OF FIRST BLUE LIGHT<br>EMISSION OF GREEN LIGHT<br>EMISSION OF RED LIGHT | (B1,G1,R1) |
| SECOND FRAME | EMISSION OF SECOND BLUE LIGHT<br>EMISSION OF GREEN LIGHT<br>EMISSION OF RED LIGHT | (B2,G2,R2) |
| THIRD FRAME | EMISSION OF GREEN LIGHT | (B3,G3,R3) |

| | B1 | G2 | R2 |
|---|---|---|---|
| OXYGEN SATURATION DEPENDENCE | HIGH | LOW | MEDIUM |
| BLOOD CONCENTRATION DEPENDENCE | MEDIUM | HIGH | LOW |
| BRIGHTNESS DEPENDENCE | PRESENCE | PRESENCE | PRESENCE |

FIG. 17

| | X | Y |
|---|---|---|
| OXYGEN SATURATION DEPENDENCE | MEDIUM | HIGH |
| BLOOD CONCENTRATION DEPENDENCE | HIGH | MEDIUM |
| BRIGHTNESS DEPENDENCE | ABSENCE | ABSENCE |

FIG. 18

| | B1 | G2 | R2 |
|---|---|---|---|
| OXYGEN SATURATION DEPENDENCE | HIGH | LOW | MEDIUM |
| BLOOD CONCENTRATION DEPENDENCE | MEDIUM | HIGH | LOW |
| YELLOW PIGMENT DEPENDENCE | HIGH | LOW TO MEDIUM | LOW |
| BRIGHTNESS DEPENDENCE | PRESENCE | PRESENCE | PRESENCE |

Figures 19, 20:
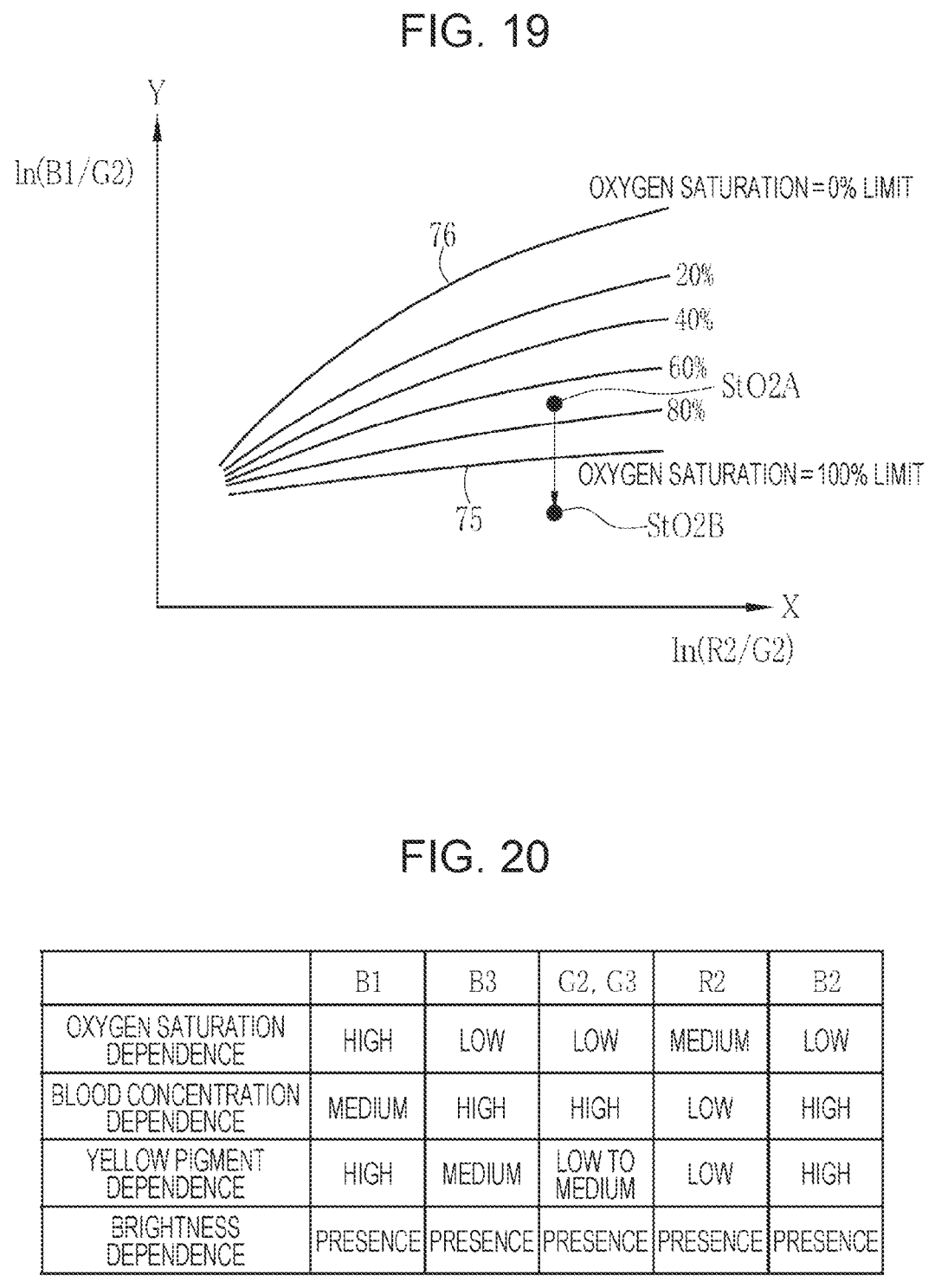

| | B1 | B3 | G2, G3 | R2 | B2 |
|---|---|---|---|---|---|
| OXYGEN SATURATION DEPENDENCE | HIGH | LOW | LOW | MEDIUM | LOW |
| BLOOD CONCENTRATION DEPENDENCE | MEDIUM | HIGH | HIGH | LOW | HIGH |
| YELLOW PIGMENT DEPENDENCE | HIGH | MEDIUM | LOW TO MEDIUM | LOW | HIGH |
| BRIGHTNESS DEPENDENCE | PRESENCE | PRESENCE | PRESENCE | PRESENCE | PRESENCE |

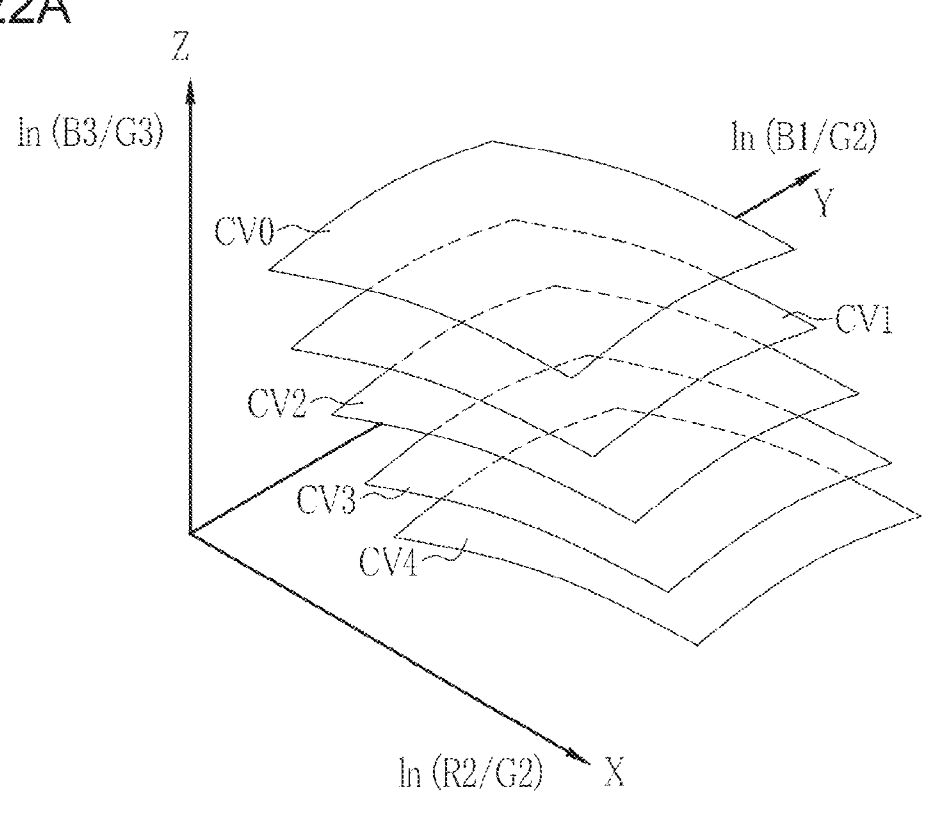
FIG. 22B
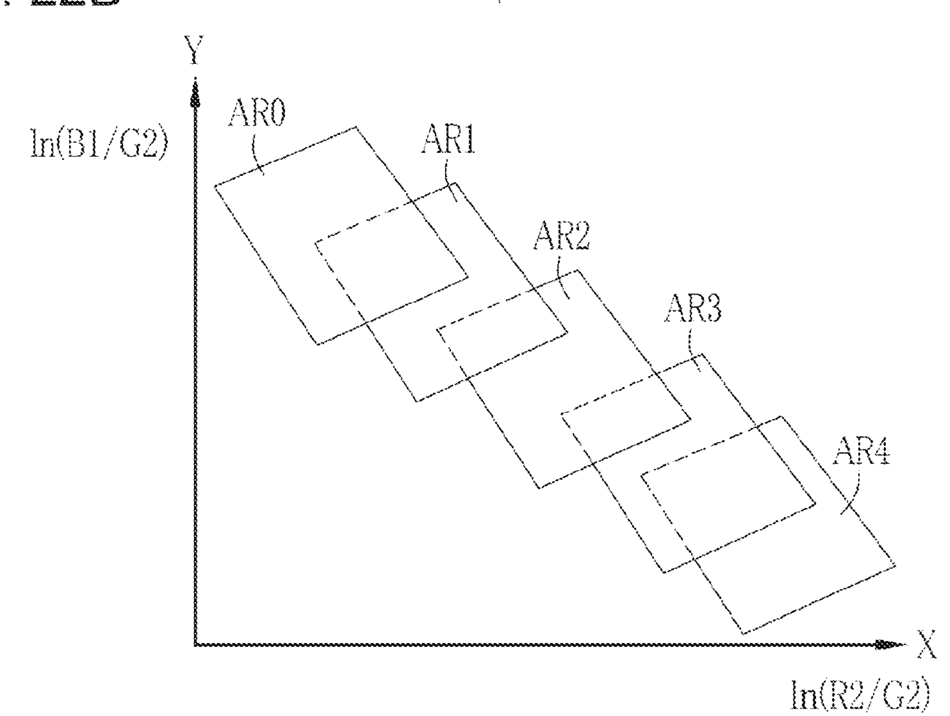

FIG. 23

| | X | Y | Z |
|---|---|---|---|
| OXYGEN SATURATION DEPENDENCE | MEDIUM | HIGH | LOW TO MEDIUM |
| BLOOD CONCENTRATION DEPENDENCE | HIGH | MEDIUM | LOW TO MEDIUM |
| YELLOW PIGMENT DEPENDENCE | LOW TO MEDIUM | HIGH | MEDIUM |
| BRIGHTNESS DEPENDENCE | ABSENCE | ABSENCE | ABSENCE |

FIG. 26
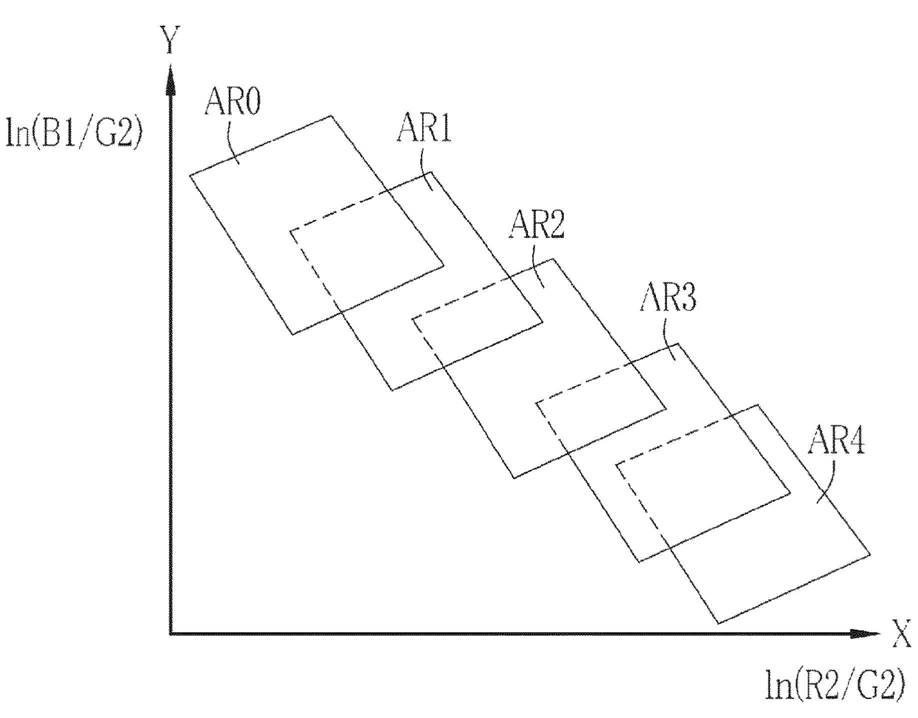
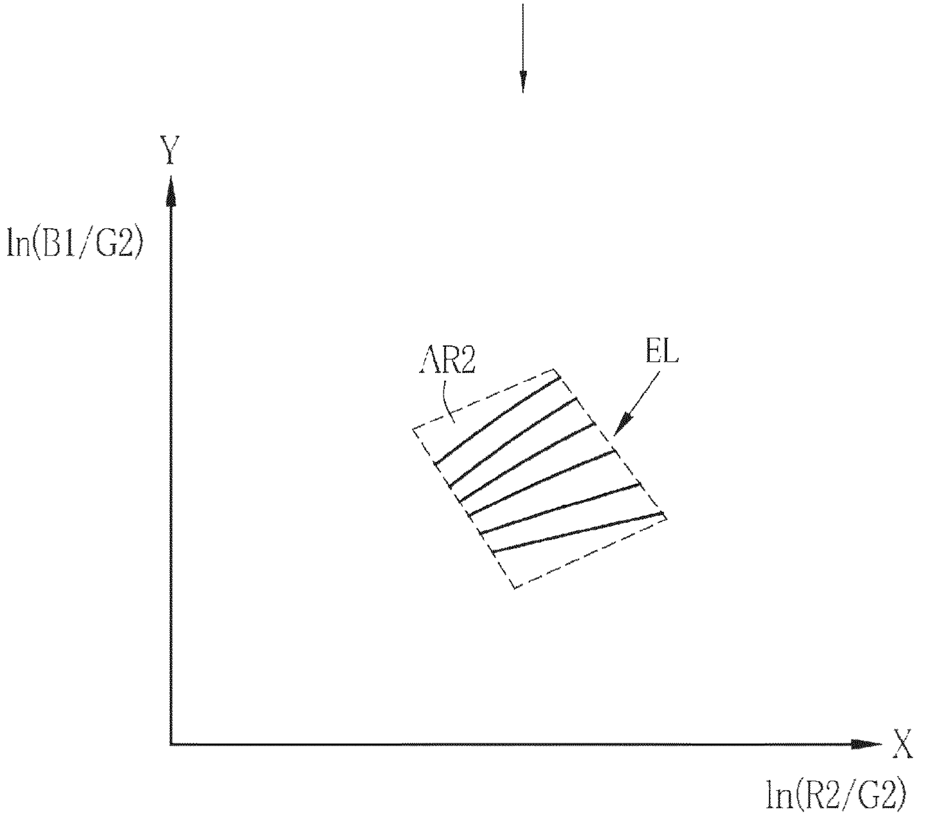

RELIABILITY

Rx

G2 IMAGE SIGNAL PIXEL VALUE

Figure 36:
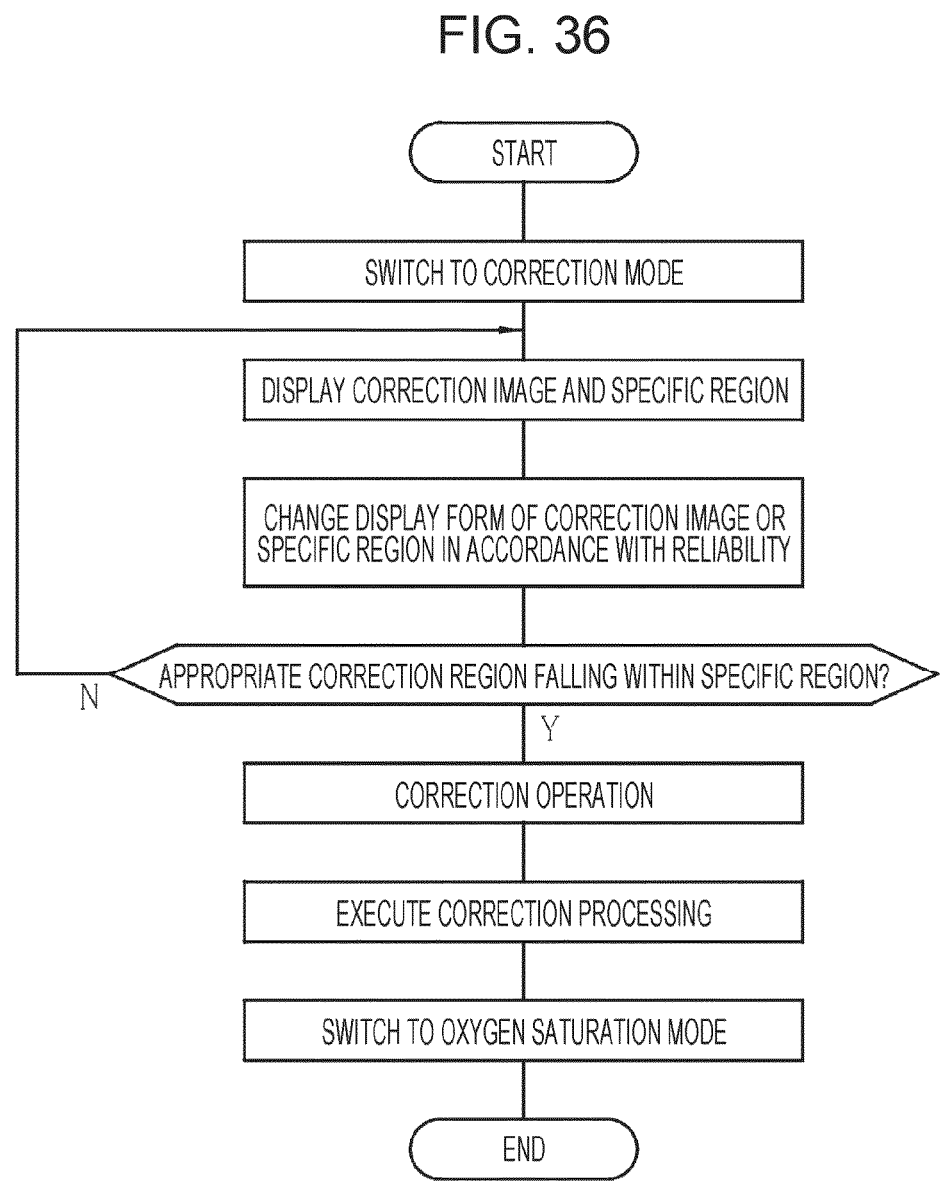

START
SWITCH TO CORRECTION MODE
DISPLAY CORRECTION IMAGE AND SPECIFIC REGION
CHANGE DISPLAY FORM OF CORRECTION IMAGE OR SPECIFIC REGION IN ACCORDANCE WITH RELIABILITY
APPROPRIATE CORRECTION REGION FALLING WITHIN SPECIFIC REGION?
N
Y
CORRECTION OPERATION
EXECUTE CORRECTION PROCESSING
SWITCH TO OXYGEN SATURATION MODE
END

INTENSITY OF LIGHT 350 450 550 650 750

WAVELENGTH (nm)

Figures 48, 49:
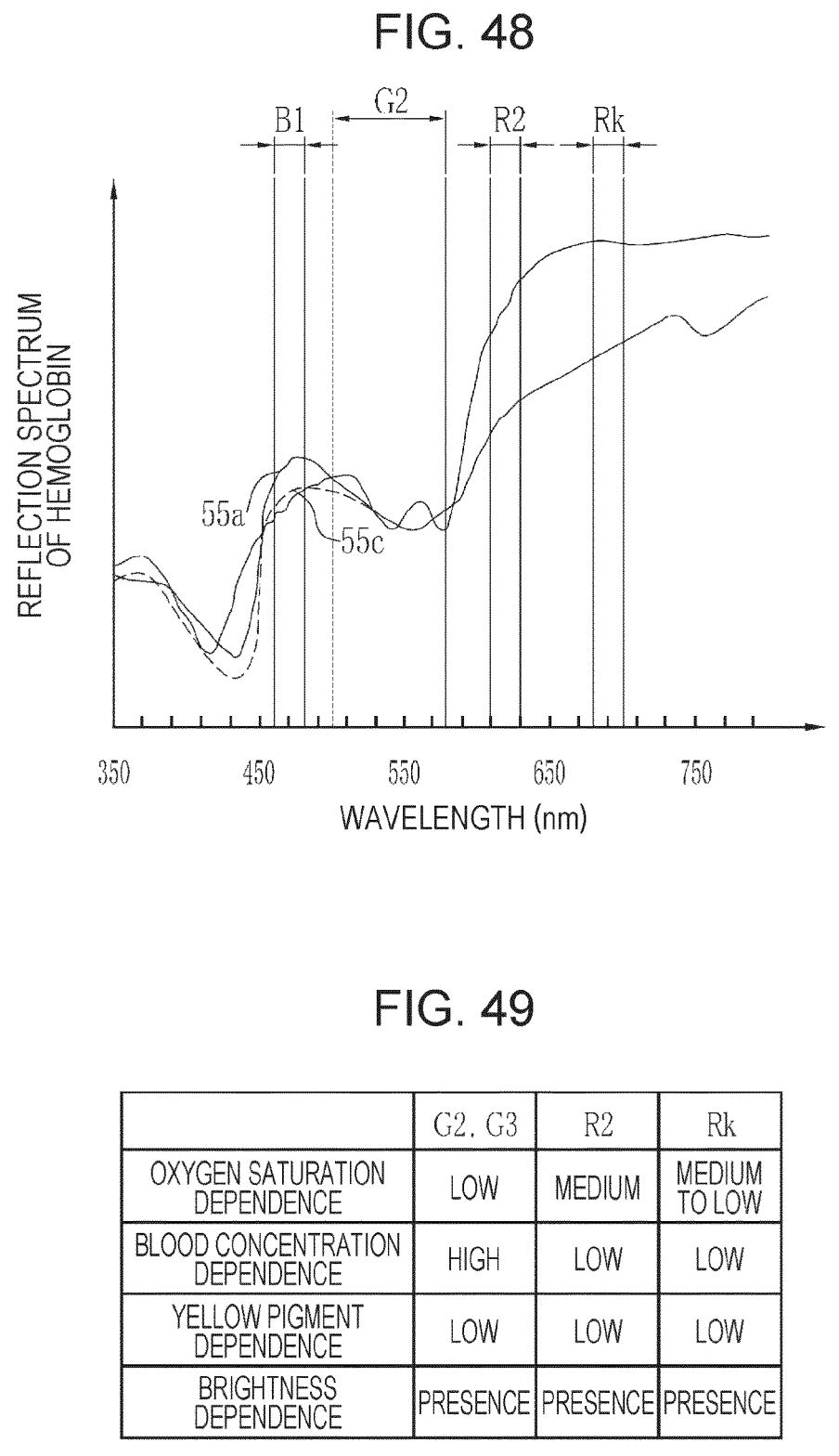

| | G2, G3 | R2 | Rk |
|---|---|---|---|
| OXYGEN SATURATION DEPENDENCE | LOW | MEDIUM | MEDIUM TO LOW |
| BLOOD CONCENTRATION DEPENDENCE | HIGH | LOW | LOW |
| YELLOW PIGMENT DEPENDENCE | LOW | LOW | LOW |
| BRIGHTNESS DEPENDENCE | PRESENCE | PRESENCE | PRESENCE |

INTENSITY OF LIGHT
350
450
550
650
750
WAVELENGTH (nm)

TRANSMITTANCE
350
450
550
650
750
WAVELENGTH (nm)

SENSITIVITY
350
450
550
650
750
WAVELENGTH (nm)

PIXEL VALUE
350
450
550
650
750
WAVELENGTH (nm)

INTENSITY OF LIGHT
WAVELENGTH (nm)
350
450
550
650
750

TRANSMITTANCE
WAVELENGTH (nm)
350
450
550
650
750

SENSITIVITY
WAVELENGTH (nm)
350
450
550
650
750

PIXEL VALUE
WAVELENGTH (nm)
350
450
550
650
750

INTENSITY OF LIGHT
WAVELENGTH (nm)
350
450
550
650
750

TRANSMITTANCE
WAVELENGTH (nm)
350
450
550
650
750

SENSITIVITY
WAVELENGTH (nm)
350
450
550
650
750

PIXEL VALUE
WAVELENGTH (nm)
450
550

PIXEL VALUE
WAVELENGTH (nm)
450
550

FIG. 55

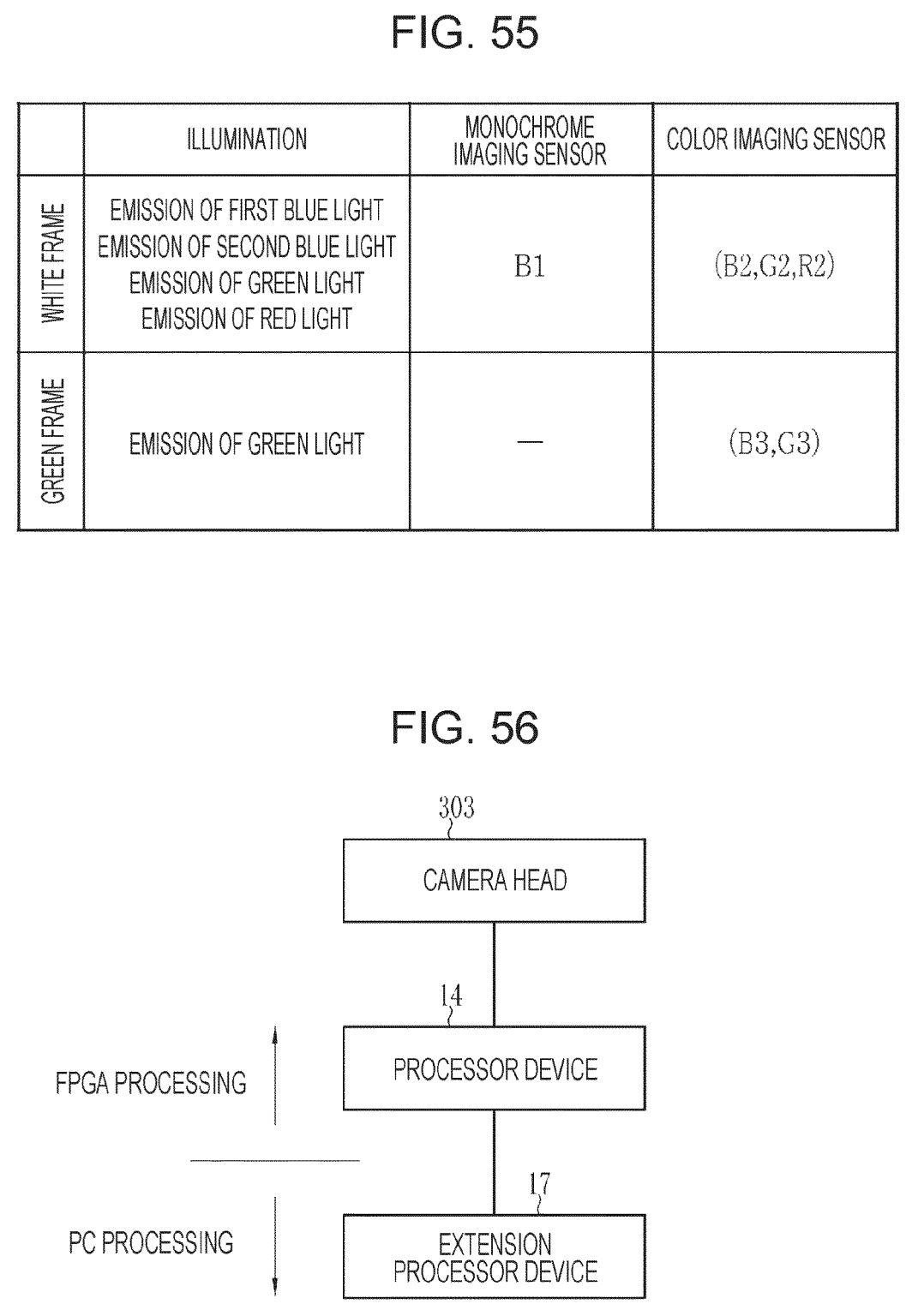

| | ILLUMINATION | MONOCHROME IMAGING SENSOR | COLOR IMAGING SENSOR |
|---|---|---|---|
| WHITE FRAME | EMISSION OF FIRST BLUE LIGHT<br>EMISSION OF SECOND BLUE LIGHT<br>EMISSION OF GREEN LIGHT<br>EMISSION OF RED LIGHT | B1 | (B2,G2,R2) |
| GREEN FRAME | EMISSION OF GREEN LIGHT | — | (B3,G3) |

Figure 57:
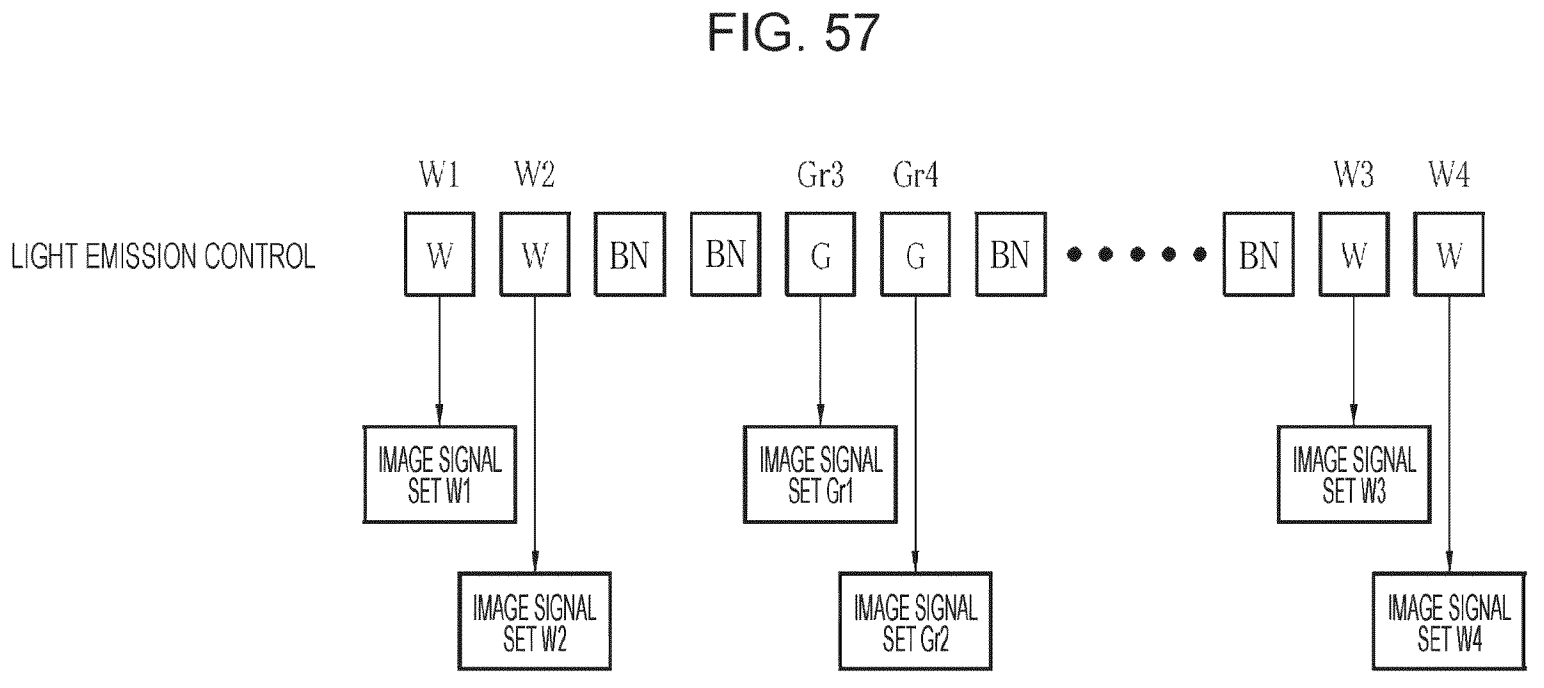

LIGHT EMISSION CONTROL

W1 W
W2 W
BN
BN
Gr3 G
Gr4 G
BN
BN
W3 W
W4 W

IMAGE SIGNAL SET W1
IMAGE SIGNAL SET W2
IMAGE SIGNAL SET Gr1
IMAGE SIGNAL SET Gr2
IMAGE SIGNAL SET W3
IMAGE SIGNAL SET W4

EFFECTIVE PIXEL DATA W2
EFFECTIVE PIXEL DATA Gr1
RELIABILITY CALCULATION
SPECIFIC PIGMENT CONCENTRATION CALCULATION
EFFECTIVE PIXEL DATA Gr2
EFFECTIVE PIXEL DATA W3
RELIABILITY CALCULATION
SPECIFIC PIGMENT CONCENTRATION CALCULATION
SPECIFIC PIGMENT CONCENTRATION CORRELATION DETERMINATION
DETERMINATION OF SPECIFIC PIGMENT CONCENTRATION

ENDOSCOPE SYSTEM AND METHOD FOR OPERATING THE SAME

CROSS-REFERENCE TO RELATED APPLICATIONS

This application is a Continuation of PCT International Application No. PCT/JP2022/039943 filed on 26 Oct. 2022, which claims priorities under 35 U.S.C § 119 (a) to Japanese Patent Application No. 2021-208312 filed on 22 Dec. 2021, and Japanese Patent Application No. 2022-139982 filed on 2 Sep. 2022. The above application is hereby expressly incorporated by reference, in its entirety, into the present application.

BACKGROUND OF THE INVENTION

1. Field of the Invention

The present invention relates to an endoscope system for calculating the oxygen saturation of an observation target, and a method for operating the endoscope system.

2. Description of the Related Art

In recent years, oxygen saturation imaging has been known in the medical field using an endoscope. The oxygen saturation imaging is performed by capturing an image of an observation target irradiated with illumination light including a wavelength range in which the absorption coefficient changes in accordance with a change in the oxygen saturation of blood hemoglobin (e.g., JP6412252B (corresponding to US2018/0020903A1) and JP6039639B (corresponding to US2015/0238126A1)). Then, the captured image is used to change the color tone in accordance with the oxygen saturation to produce an oxygen saturation image, and the oxygen saturation image is displayed on a display.

However, if a yellow pigment or the like is present in the observation target, the yellow pigment or the like affects the absorption of light by blood hemoglobin, which causes a problem in that a calculated value of the oxygen saturation deviates. In JP6039639B, in contrast, in addition to an image necessary for calculation of the oxygen saturation, an image of around 450 nm having an absorption peak for the yellow pigment is used to calculate the oxygen saturation in consideration of the influence of the yellow pigment.

SUMMARY OF THE INVENTION

Examples of a method for eliminating the influence of the yellow pigment or the like include, in addition to the method as in JP6039639B for calculating the oxygen saturation in consideration of the influence of the yellow pigment, a method for performing a correction operation before the calculation of the oxygen saturation to calculate the yellow pigment contained in the observation target and correcting an oxygen saturation calculation table in accordance with the calculated yellow pigment.

In the correction operation described above, if a disturbance (such as bleeding, a residual liquid, an adherent such as mucus, or halation) affecting the calculation accuracy of the oxygen saturation, as well as the yellow pigment, is present in the observation target during the correction operation, the correction operation may fail, and the oxygen saturation calculation table may be incorrectly corrected. In addition, the range of an organ appearing in a region of interest changes each time imaging is performed. Thus, it is difficult to perform a correction operation while avoiding disturbance.

It is an object of the present invention to provide an endoscope system for correcting an oxygen saturation calculation table by a correction operation performed by a user, in which the user can correctly perform the correction operation even if a disturbance affecting the calculation of the oxygen saturation is present in an observation target, and a method for operating the endoscope system.

An endoscope system according to the present invention includes a processor, and the processor is configured to switch between an oxygen saturation mode for calculating an oxygen saturation of blood hemoglobin and a correction mode for displaying a correction image on a display and displaying a specific region on the display, the correction mode being a mode in which correction processing related to calculation of the oxygen saturation is performed based on a specific pigment concentration of a specific pigment other than the blood hemoglobin included in the specific region, the specific pigment concentration being calculated based on a specific pigment image signal including image information of a wavelength range having sensitivity to the specific pigment; and in the correction mode, perform at least one of changing a display style of the correction image or changing a display style of the specific region in accordance with reliability related to the calculation of the oxygen saturation.

Preferably, the processor is configured to generate a correction image with a reduced luminance of a dark portion. Preferably, the processor is configured to generate a correction image with saturation enhanced. Preferably, the processor is configured to: change the display style of the correction image so that a difference between a low-reliability region in which the reliability is low and a high-reliability region in which the reliability is high is emphasized. Preferably, the processor is configured to set a saturation of the low-reliability region to be higher than a saturation of the high-reliability region. Preferably, the processor is configured to reduce a luminance of a dark portion in the low-reliability region. Preferably, the processor is configured to perform at least one of superimposing a region highlighting line on the low-reliability region or displaying the low-reliability region in monochrome.

Preferably, the processor is configured to the processor is configured to determine whether it is possible to appropriately perform the correction processing, based on the reliability in the specific region; and make the display style of the specific region different between when it is possible to appropriately perform the correction processing and when it is not possible to appropriately perform the correction processing. Preferably, the processor is configured to processor is configured to make a determination as to whether it is possible to appropriately perform the correction processing, based on the reliability in the specific region at a timing at which a correction operation for performing the correction processing is performed; and provide a notification related to the determination.

Preferably, the processor is configured to provide a notification of operational guidance for performing the correction processing in an appropriate manner when it is determined that it is not possible to appropriately perform the correction processing. Preferably, the reliability for a brightness value outside a certain range is lower than the reliability for a brightness value within the certain range, and the reliability varies in accordance with a disturbance including at least bleeding, fat, a residue, mucus, or a residual liquid.

Preferably, the correction processing is either table correction processing or calculation value correction processing, the table correction processing being for correcting an oxygen saturation calculation table used to calculate the oxygen saturation based on a specific pigment concentration of the specific pigment, the calculation value correction processing being for adding or subtracting a correction value obtained from the specific pigment concentration to or from the oxygen saturation calculated based on the oxygen saturation calculation table.

Preferably, in the correction mode, instead of the correction processing, specific oxygen saturation calculation processing for calculating the oxygen saturation in accordance with the specific pigment concentration is performed based on an oxygen-saturation image signal and the specific pigment image signal, the oxygen-saturation image signal including at least image information of a wavelength range in which an absorption coefficient changes in accordance with a change in the oxygen saturation.

The present invention provides a method for operating an endoscope system including a processor. The method includes a step of, by the processor, switching between an oxygen saturation mode for calculating an oxygen saturation of blood hemoglobin and a correction mode for displaying a correction image on a display and displaying a specific region on the display, the correction mode being a mode in which correction processing related to calculation of the oxygen saturation is performed based on a specific pigment concentration of a specific pigment other than the blood hemoglobin included in the specific region. The specific pigment concentration is calculated based on a specific pigment image signal including image information of a wavelength range having sensitivity to the specific pigment. In the correction mode, at least one of changing a display style of the correction image or changing a display style of the specific region in accordance with reliability related to the calculation of the oxygen saturation is performed.

According to the present invention, in correction of an oxygen saturation calculation table by a correction operation performed by a user, the user can correctly perform the correction operation even if a disturbance affecting the calculation of the oxygen saturation is present in an observation target.

BRIEF DESCRIPTION OF THE DRAWINGS

FIG. 2 is an explanatory diagram illustrating display styles on a display and an extension display in a normal mode;

FIG. 3 is an explanatory diagram illustrating display styles on the display and the extension display in an oxygen saturation mode;

FIG. 5A is an image diagram of the extension display that displays an internal-digestive-tract oxygen saturation image, and FIG. 5B is an image diagram of the extension display that displays a serosa-side oxygen saturation image;

FIG. 10 is a table illustrating illumination and image signals to be acquired in the normal mode;

FIG. 11 is a table illustrating illumination and image signals to be acquired in the oxygen saturation mode or a correction mode;

FIG. 17 is a table illustrating oxygen saturation dependence, blood concentration dependence, and brightness dependence related to values on an X-axis indicating a signal ratio ln(R2/G2) and values on a Y-axis indicating a signal ratio ln(B1/G2);

FIG. 18 is a table illustrating oxygen saturation dependence, blood concentration dependence, yellow pigment dependence, and brightness dependence of a B1 image signal, a G2 image signal, and an R2 image signal with the influence of the yellow pigment;

FIG. 19 is an explanatory diagram illustrating the oxygen saturation in the presence of the yellow pigment and the oxygen saturation in the absence of the yellow pigment when the observation target has the same oxygen saturation;

FIG. 20 is a table illustrating oxygen saturation dependence, blood concentration dependence, yellow pigment dependence, and brightness dependence of a B1 image signal, a B3 image signal, G2 and G3 image signals, an R2 image signal, and a B2 image signal with the influence of the yellow pigment;

FIGS. 22A and 22B are explanatory diagrams of a case where the state of the oxygen saturation represented by three-dimensional coordinates of X, Y, and Z is represented by two-dimensional coordinates of X and Y;

FIG. 23 is a table illustrating oxygen saturation dependence, blood concentration dependence, yellow pigment dependence, and brightness dependence related to values on the X-axis indicating the signal ratio ln(R2/G2), values on the Y-axis indicating the signal ratio ln (B1/G2), and values on a Z-axis indicating a signal ratio ln(B3/G3);

FIG. 26 is an explanatory diagram illustrating a method for generating a contour corresponding to a specific pigment concentration;

FIG. 33A is an image diagram of the display that displays the specific region highlighted in a first color, and FIG. 33B is an image diagram of the display that displays the specific region highlighted in a second color;

FIG. 34 is an image diagram of the display when it is determined that it is possible to appropriately perform table correction processing;

FIG. 36 is a flowchart illustrating the flow of a series of operations in the correction mode;

FIG. 48 is a graph illustrating a wavelength range Rk in reflection spectra of hemoglobin that differ depending on the concentration of the yellow pigment;

FIG. 49 is a table illustrating oxygen saturation dependence, blood concentration dependence, yellow pigment dependence, and brightness dependence of G2 and G3 image signals, an R2 image signal, and an Rk image signal with the influence of the yellow pigment;

FIGS. 51A and 51B are graphs illustrating light emission patterns for the two-sensor laparoscopic endoscope, in which FIG. 51A illustrates a light emission pattern during a white frame, and FIG. 51B illustrates a light emission pattern during a green frame;

FIG. 55 is a table illustrating image signals to be used in the oxygen saturation mode or the correction mode among image signals obtained in the white frame or the green frame;

FIG. 56 is an explanatory diagram illustrating FPGA processing or PC processing;

FIG. 57 is an explanatory diagram illustrating light emission control and image signal sets for the two-sensor laparoscopic endoscope;

DESCRIPTION OF THE PREFERRED EMBODIMENTS

First Embodiment

Figure 1:
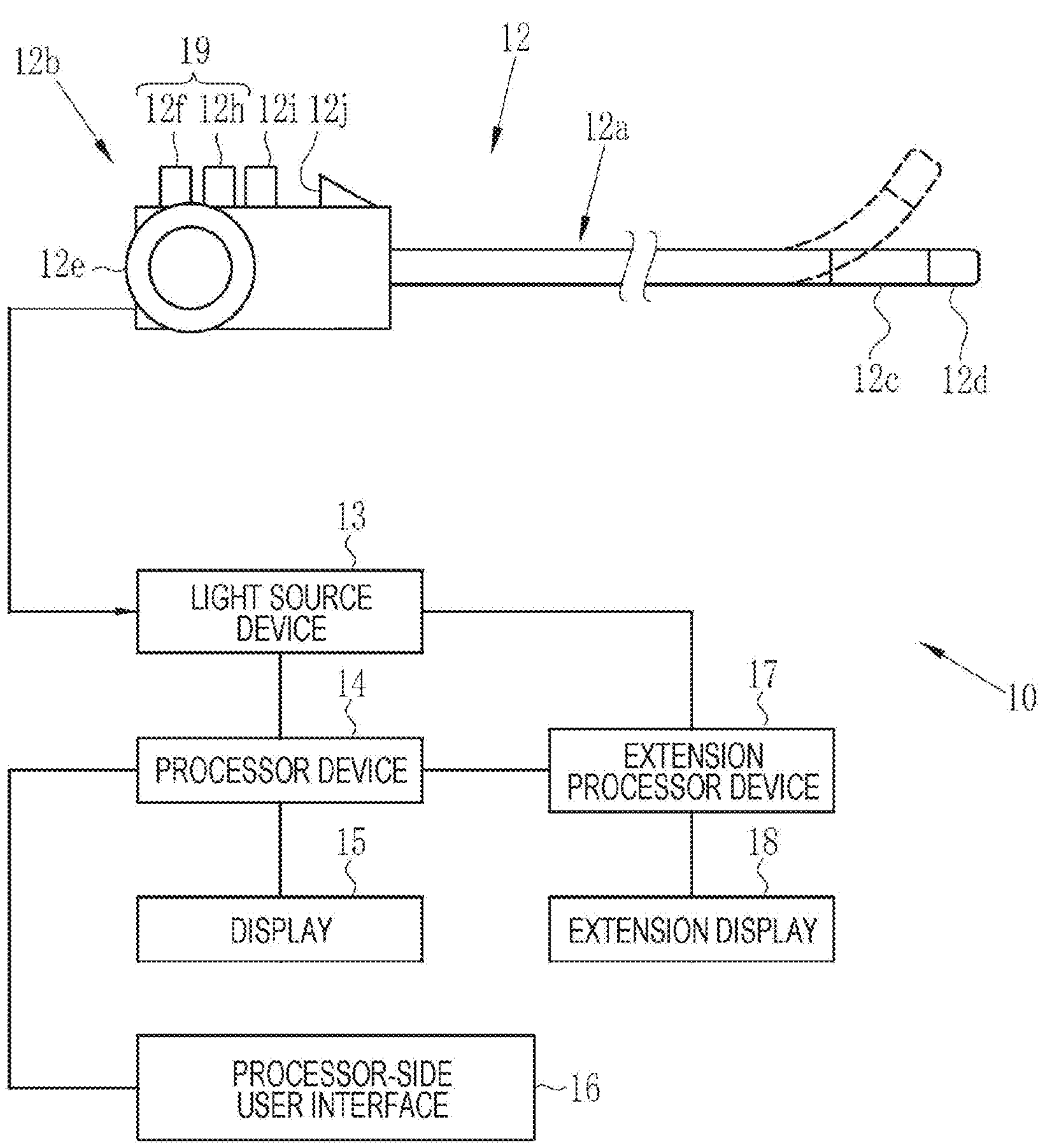
FIG. 1 is a schematic diagram of an endoscope system for digestive-tract endoscopy.

As illustrated in FIG. 1, an endoscope system 10 includes an endoscope 12, a light source device 13, a processor device 14, a display 15, a processor-side user interface 16, an extension processor device 17, and an extension display 18. The endoscope 12 is optically or electrically connected to the light source device 13 and is electrically connected to the processor device 14. The extension processor device 17 is electrically connected to the light source device 13 and the processor device 14. In the claims, a "display" includes the extension display 18 in addition to the display 15.

The endoscope 12 has an insertion section **12*a*, an operation section 12*b*, a bending part 12*c*, and a tip part 12*d*. The insertion section 12*a* is inserted into the body of a photographic subject. The operation section 12*b* is disposed in a proximal end portion of the insertion section 12*a*. The bending part 12*c* and the tip part 12*d* are disposed on the distal end side of the insertion section 12*a*. The bending part 12*c* performs a bending operation in response to an operation of an angle knob 12*e* of the operation section 12*b*. The tip part 12*d* is directed in a desired direction by the bending operation of the bending part 12*c*. A forceps channel (not illustrated) is provided from the insertion section 12***a* to the tip part 12*d* to insert a treatment tool or the like through the forceps channel. The treatment tool is inserted into the forceps channel from a forceps port 12*j*.

The endoscope 12 is internally provided with an optical system for forming a photographic subject image and an optical system for irradiating the photographic subject with illumination light. The operation section 12*b* is provided with the angle knob 12*e*, a mode switch 12*f*, a still-image acquisition instruction switch 12*h*, and a zoom operation unit 12*i*. The mode switch 12*f* is used for an observation mode switching operation. The still-image acquisition instruction switch 12*h* is used to provide an instruction to acquire a still image of the photographic subject. The zoom operation unit 12*i* is used to perform an operation of enlarging or shrinking the observation target. The operation section 12*b* may be provided with the mode switch 12*f*, the still-image acquisition instruction switch 12*h*, and a scope-side user interface 19 for performing various operations on the processor device 14.

The light source device 13 generates illumination light. The processor device 14 performs system control of the endoscope system 10 and further performs image processing and the like on an image signal transmitted from the endoscope 12 to generate an endoscopic image, for example. The display 15 displays a medical image transmitted from the processor device 14. The processor-side user interface 16 has a keyboard, a mouse, a microphone, a tablet, a foot switch, a touch pen, and the like, and accepts an input operation such as setting a function.

The endoscope system 10 has three modes, namely, a normal mode, an oxygen saturation mode, and a correction mode, and the three modes are switched by the user operating the mode switch 12*f*. As illustrated in FIG. 2, in the normal mode, a white-light image with a natural tint, which is obtained by imaging of the observation target using white light as illumination light, is displayed on the display 15, whereas nothing is displayed on the extension display 18.

Figure 4:
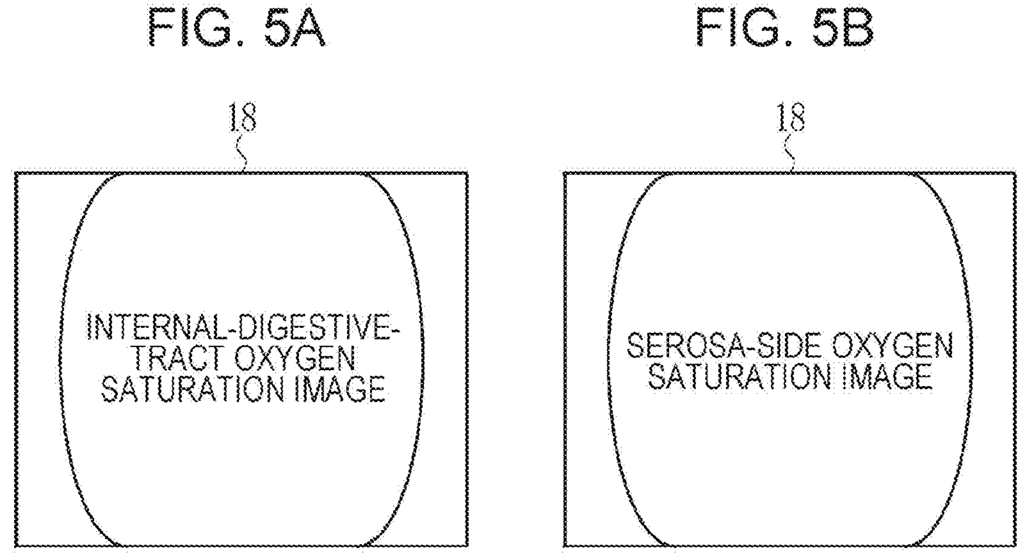
FIG. 4 is an explanatory diagram illustrating a display style of the extension display presented at a timing of switching to the oxygen saturation mode.

As illustrated in FIG. 3, in the oxygen saturation mode, the oxygen saturation of the observation target is calculated, and an oxygen saturation image that is an image of the calculated oxygen saturation is displayed on the extension display 18. In the oxygen saturation mode, furthermore, a white-light-equivalent image having fewer short-wavelength components than the white-light image is displayed on the display 15. In the correction mode, correction processing related to the calculation of the oxygen saturation is performed on the basis of the specific pigment concentration of a specific pigment other than blood hemoglobin, such as a yellow pigment. When the mode is switched to the oxygen saturation mode, as illustrated in FIG. 4, a message MS0 indicating "Please perform correction processing" is displayed on the extension display 18. When the correction processing is completed, the oxygen saturation image is displayed on the extension display 18.

The endoscope system 10 is of a soft endoscope type for the digestive tract such as the stomach or the large intestine. In the oxygen saturation mode, as illustrated in FIG. 5A, an internal-digestive-tract oxygen saturation image that is an image of the state of the oxygen saturation inside the digestive tract is displayed on the extension display 18. In an endoscope system described below, in the case of a rigid endoscope type for the abdominal cavity such as the serosa, as illustrated in FIG. 5B, a serosa-side oxygen saturation image that is an image of the state of the oxygen saturation on the serosa side is displayed on the extension display 18 in the oxygen saturation mode. The serosa-side oxygen saturation image is preferably an image obtained by adjusting the saturation of the white-light-equivalent image. The adjustment of the saturation is preferably performed in the correction mode regardless of the mucosa or the serosa and the soft endoscope or the rigid endoscope.

In the oxygen saturation mode, it is possible to accurately calculate the oxygen saturation in the following cases:

observation of a predetermined target site (e.g., the esophagus, the stomach, or the large intestine);

environments other than the extracorporeal environment with illumination therearound;

no residue, residual liquid, mucus, blood, or fat remaining on the mucous membrane and the serosa;

no pigment sprayed onto the mucous membrane;

the endoscope 12 located away more than 7 mm from the site to be observed;

observation of the site to be observed with the endoscope at an appropriate distance therebetween without large separation;

a region irradiated with sufficient illumination light;

small specular reflection of light from the site to be observed;

a ⅔ internal region of an oxygen saturation image;

small movement of the endoscope or small movement of the patient such as pulsation or breathing; and no observation of blood vessels in a deep portion of the mucous membrane of the digestive tract.

Figure 6:
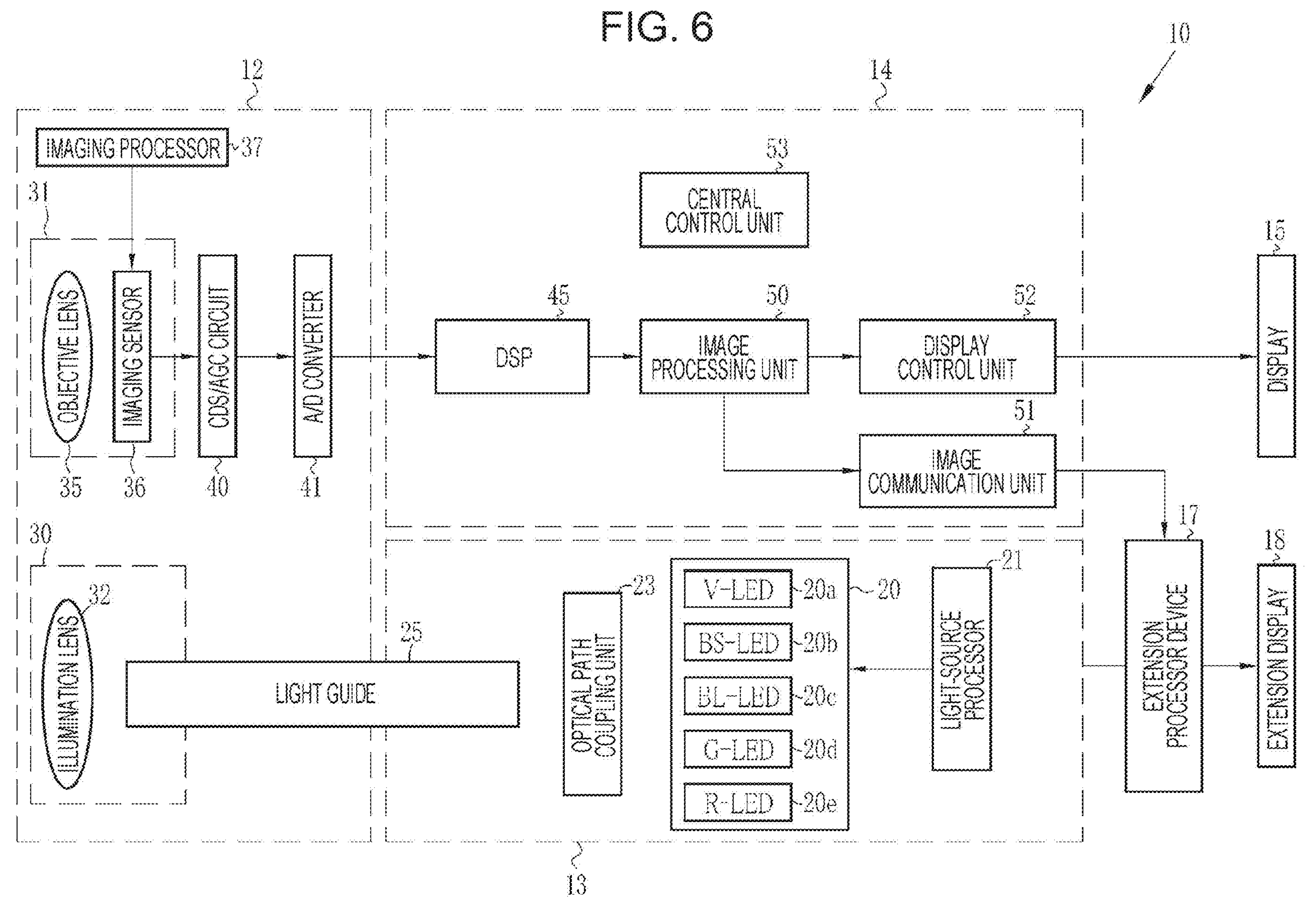
FIG. 6 is a block diagram illustrating functions of an endoscope system according to a first embodiment.

As illustrated in FIG. 6, the light source device 13 includes a light source unit 20 and a light-source processor 21 that controls the light source unit 20. The light source unit 20 has, for example, a plurality of semiconductor light sources and turns on or off each of the semiconductor light sources. The light source unit 20 turns on the semiconductor light sources by controlling the amounts of light to be emitted from the respective semiconductor light sources to emit illumination light for illuminating the observation target. In this embodiment, the light source unit 20 has LEDs of five colors, namely, a V-LED (Violet Light Emitting Diode) 20*a*, a BS-LED (Blue Short-wavelength Light Emitting Diode) 20*b*, a BL-LED (Blue Long-wavelength Light Emitting Diode) 20*c*, a G-LED (Green Light Emitting Diode) 20*d*, and an R-LED (Red Light Emitting Diode) 20*e*.

The V-LED 20*a* emits violet light V of 410 nm±10 nm. The BS-LED 20*b* emits second blue light BS of 450 nm±10 nm. The BL-LED 20*c* emits first blue light BL of 470 nm±10 nm. The G-LED 20*d* emits green light G in the green range. The green light G preferably has a center wavelength of 540 nm. The R-LED 20*e* emits red light R in the red range. The red light R preferably has a center wavelength of 620 nm. The center wavelengths and the peak wavelengths of the LEDs 20*a* to 20*e* may be the same or different.

The light-source processor 21 independently inputs control signals to the respective LEDs 20*a* to 20*e* to independently control turning on or off of the respective LEDs 20*a* to 20*e*, the amounts of light to be emitted at the time of turning on of the respective LEDs 20*a* to 20*e*, and so on. The turn-on or turn-off control performed by the light-source processor 21 differs depending on the mode, which will be described below.

The light emitted from each of the LEDs 20*a* to 20*e* is incident on a light guide 25 via an optical path coupling unit 23 constituted by a mirror, a lens, and the like. The light guide 25 is incorporated in the endoscope 12 and a universal cord (a cord that connects the endoscope 12 to the light source device 13 and the processor device 14). The light guide 25 propagates the light from the optical path coupling unit 23 to the tip part 12*d* of the endoscope 12.

The tip part 12*d* of the endoscope 12 is provided with an illumination optical system 30 and an imaging optical system 31. The illumination optical system 30 has an illumination lens 32. The illumination light propagating through the light guide 25 is applied to the observation target via the illumination lens 32. The imaging optical system 31 has an objective lens 35 and an imaging sensor 36. Light from the observation target irradiated with the illumination light is incident on the imaging sensor 36 via the objective lens 35. As a result, an image of the observation target is formed on the imaging sensor 36.

The imaging sensor 36 is a color imaging sensor that captures an image of the observation target being illuminated with the illumination light. Each pixel of the imaging sensor 36 is provided with any one of a B pixel (blue pixel) having a B (blue) color filter, a G pixel (green pixel) having a G (green) color filter, and an R pixel (red pixel) having an R (red) color filter. The spectral transmittances of the B color filter, the G color filter, and the R color filter will be described below. For example, the imaging sensor 36 is preferably a color imaging sensor with a Bayer array of B pixels, G pixels, and R pixels, the numbers of which are in the ratio of 1:2:1.

Examples of the imaging sensor 36 can include a CCD (Charge Coupled Device) imaging sensor and a CMOS (Complementary Metal-Oxide Semiconductor) imaging sensor. Instead of the imaging sensor 36 for primary colors, a complementary color imaging sensor including complementary color filters for C (cyan), M (magenta), Y (yellow), and G (green) may be used. When a complementary color imaging sensor is used, image signals of four colors of CMYG are output. Accordingly, the image signals of the four colors of CMYG are converted into image signals of three colors of RGB by complementary-color-to-primary-color conversion. As a result, image signals of the respective colors of RGB similar to those of the imaging sensor 36 can be obtained.

Driving of the imaging sensor 36 is controlled by an imaging processor 37. The control of the respective modes, which is performed by the imaging processor 37, will be described below. A CDS/AGC circuit 40 (Correlated Double Sampling/Automatic Gain Control) performs correlated double sampling (CDS) and automatic gain control (AGC) on an analog image signal obtained from the imaging sensor 36. The image signal having passed through the CDS/AGC circuit 40 is converted into a digital image signal by an A/D converter 41 (Analog/Digital). The digital image signal subjected to A/D conversion is input to the processor device 14.

The processor device 14 includes a DSP (Digital Signal Processor) 45, an image processing unit 50, a display control unit 52, and a central control unit 53. In the processor device 14, programs related to various types of processing are incorporated in a program memory (not illustrated). The central control unit 53, which is constituted by a processor, executes a program in the program memory to implement the functions of the DSP 45, the image processing unit 50, the display control unit 52, and the central control unit 53.

The DSP 45 performs various types of signal processing, such as defect correction processing, offset processing, gain correction processing, linear matrix processing, gamma conversion processing, demosaicing processing, white balance processing, YC conversion processing, and noise reducing processing, on the image signal received from the endoscope 12. In the defect correction processing, a signal of a defective pixel of the imaging sensor 36 is corrected. In the offset processing, a dark current component is removed from the image signal subjected to the defect correction processing, and an accurate zero level is set. The gain correction processing multiplies the image signal of each color after the offset processing by a specific gain to adjust the signal level of each image signal. After the gain correction processing, the image signal of each color is subjected to linear matrix processing for improving color reproducibility.

Thereafter, gamma conversion processing is performed to adjust the brightness and saturation of each image signal. After the linear matrix processing, the image signal is subjected to demosaicing processing (also referred to as isotropic processing or synchronization processing) to generate a signal of a missing color for each pixel by interpolation. Through the demosaicing processing, all the pixels have signals of RGB colors. The DSP 45 performs YC conversion processing on the respective image signals after the demosaicing processing, and obtains brightness signals Y and color difference signals Cb and Cr. The DSP 45 performs noise reducing processing on the image signals subjected to the demosaicing processing or the like, by using, for example, a moving average method, a median filter method, or the like.

The image processing unit 50 performs various types of image processing on the image signals from the DSP 45. The image processing includes, for example, color conversion processing such as 3×3 matrix processing, gradation transformation processing, and three-dimensional LUT (Look Up Table) processing, color enhancement processing, and structure enhancement processing such as spatial frequency enhancement. The image processing unit 50 performs image processing in accordance with the mode. In the normal mode, the image processing unit 50 performs image processing for the normal mode to generate a white-light image. In the oxygen saturation mode, the image processing unit 50 performs image processing for oxygen saturation to generate a white-light-equivalent image. In the oxygen saturation mode, furthermore, the image processing unit 50 transmits the image signals from the DSP 45 to the extension processor device 17 via an image communication unit 51.

The display control unit 52 performs display control for displaying image information such as the white-light image or the oxygen saturation image from the image processing unit 50 and other information on the display 15. In accordance with the display control, the white-light image or the white-light-equivalent image is displayed on the display 15.

The extension processor device 17 receives the image signals from the processor device 14 and performs various types of image processing. In the oxygen saturation mode, the extension processor device 17 calculates the oxygen saturation and generates an oxygen saturation image that is an image of the calculated oxygen saturation. The generated oxygen saturation image is displayed on the extension display 18. In the correction mode, the extension processor device 17 calculates a specific pigment concentration in accordance with a user operation and performs correction processing related to the calculation of the oxygen saturation on the basis of the calculated specific pigment concentration. The details of the oxygen saturation mode and the correction mode performed by the extension processor device 17 will be described below.

Figure 7:
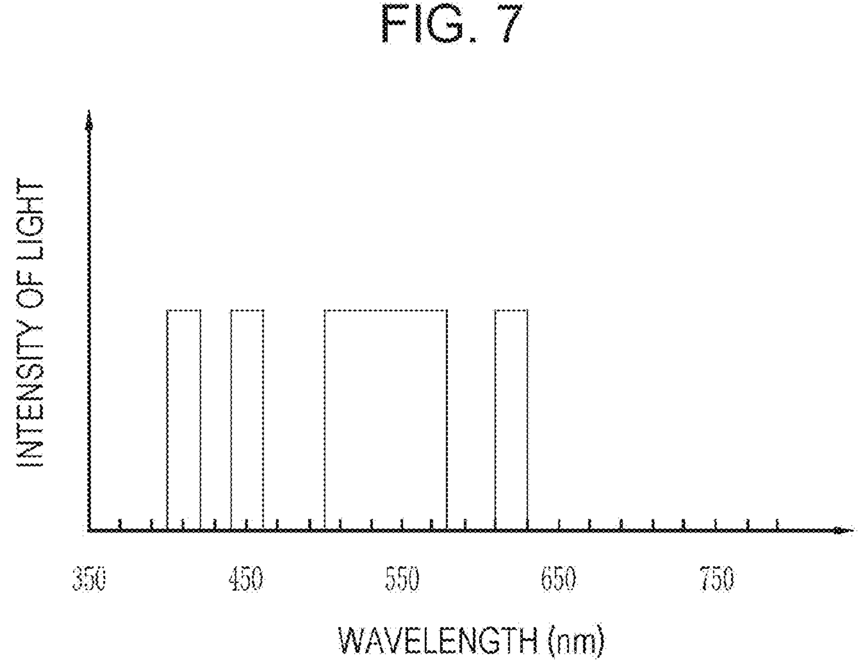
FIG. 7 is a graph illustrating emission spectra of white light.

The turn-on or turn-off control in each mode will be described. In the normal mode, when the V-LED 20*a*, the BS-LED 20*b*, the G-LED 20*d*, and the R-LED 20*e* are simultaneously turned on, as illustrated in FIG. 7, white light including violet light V having a center wavelength of 410 nm, second blue light BS having a center wavelength of 450 nm, broadband green light G in the green range, and red light R having a center wavelength of 620 nm is emitted.

Figure 8A:
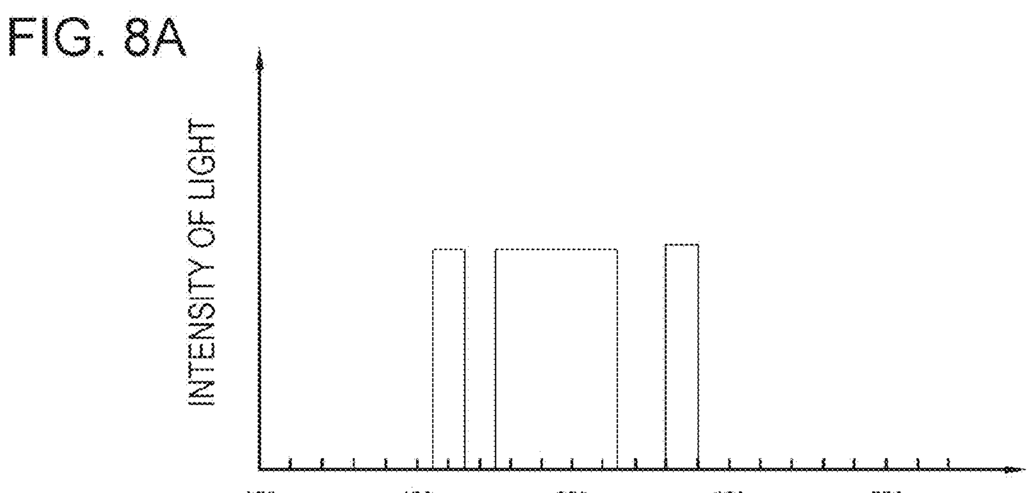
FIGS. 8A, 8B, and 8C are graphs illustrating emission spectra of first illumination light, emission spectra of second illumination light, and an emission spectrum of green light G, respectively.
Figure 8B:
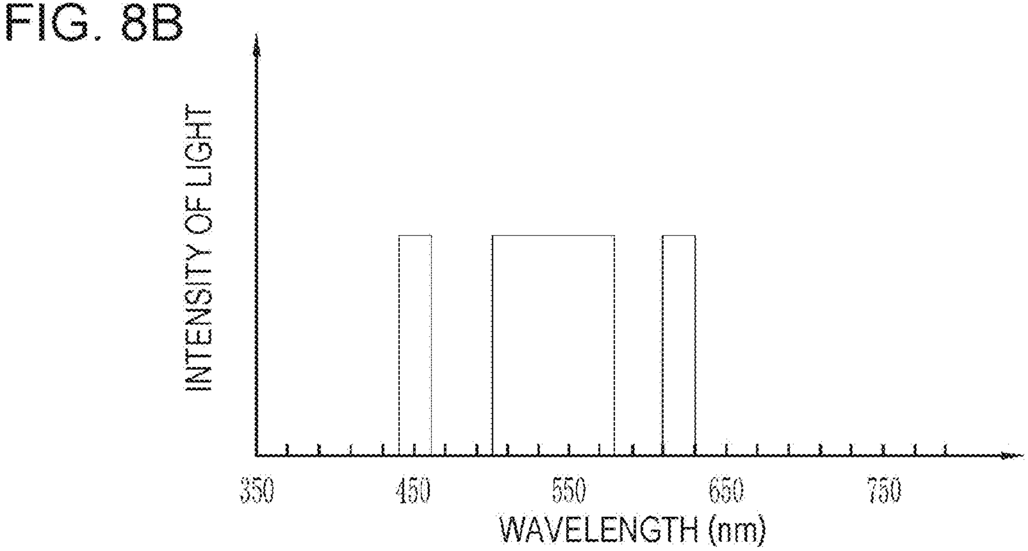
Figure 8C:
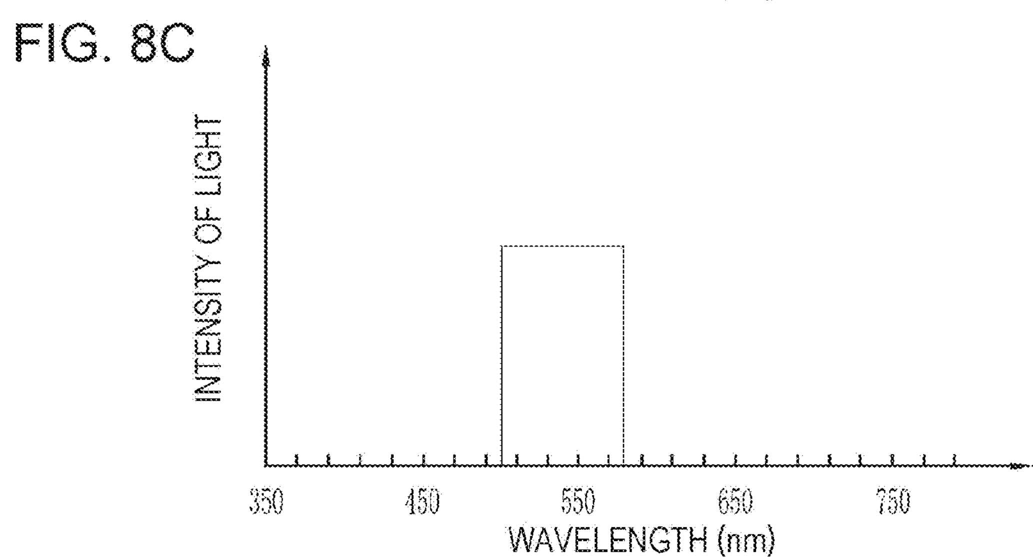

In the oxygen saturation mode and the correction mode, light emission for three frames with different light emission patterns is repeatedly performed. In the first frame, as illustrated in FIG. 8A, the BL-LED 20*c*, the G-LED 20*d*, and the R-LED 20*e* are simultaneously turned on to emit first illumination light including first blue light BL having a center wavelength of 470 nm, broadband green light G in the green range, and red light R having a center wavelength of 620 nm. In the second frame, as illustrated in FIG. 8B, the BS-LED 20*b*, the G-LED 20*d*, and the R-LED 20*e* are simultaneously turned on to emit second illumination light including second blue light BS having a center wavelength of 450 nm, broadband green light G in the green range, and red light R having a center wavelength of 620 nm. In the third frame, as illustrated in FIG. 8C, the G-LED 20*d* is turned on to emit broadband green light G in the green range. In the oxygen saturation mode, the first frame and the second frame are frames required to obtain an image signal to be required to calculate the oxygen saturation, and thus light may be emitted in only the first frame and the second frame.

Figure 9:
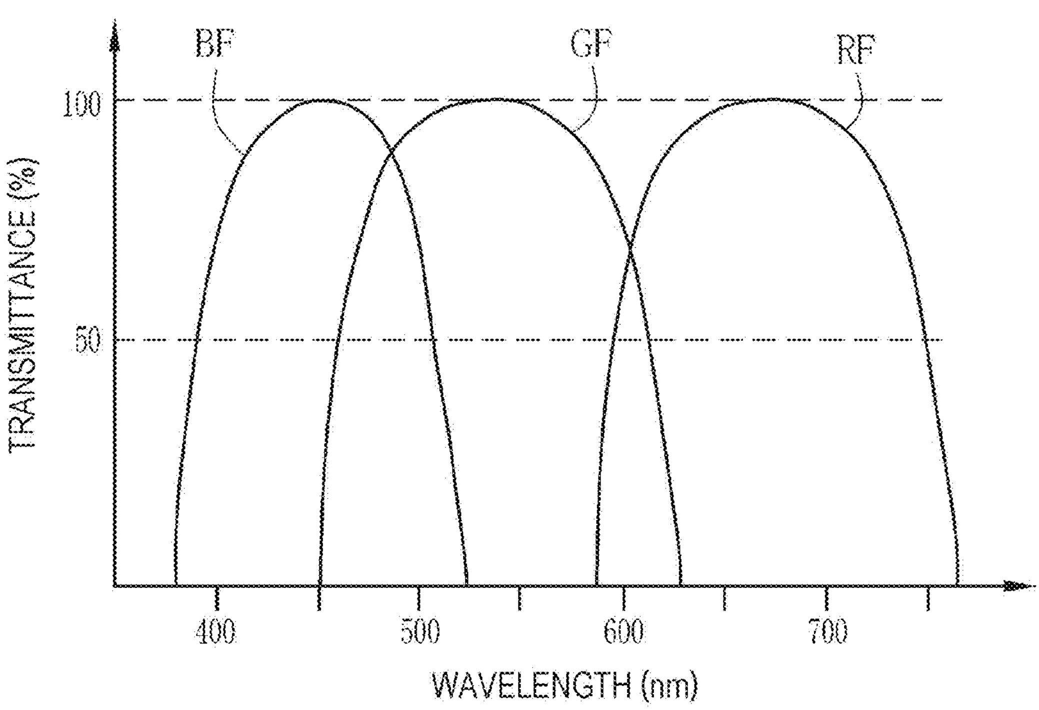
FIG. 9 is a graph illustrating spectral sensitivity of imaging sensors.

As illustrated in FIG. 9, the B pixels of the imaging sensor 36 are provided with a B color filter BF that mainly transmits light in the blue range, namely, light in the wavelength range of 380 to 560 nm (blue transmission range). A peak wavelength at which the transmittance is maximum appears around 460 to 470 nm. The G pixels of the imaging sensor 36 are provided with a G color filter GF that mainly transmits light in the green range, namely, light in the wavelength range of 450 to 630 nm (green transmission range). The R pixels of the imaging sensor 36 are provided with an R color filter RF that mainly transmits light in the red range, namely, light in the range of 580 to 760 nm (red transmission range).

As illustrated in FIG. 10, in the normal mode, the imaging processor 37 controls the imaging sensor 36 to perform imaging of the observation target, which is being illuminated with the violet light V, the second blue light BS, the green light G, and the red light R, frame by frame. As a result, a Bc image signal is output from the B pixels, a Gc image signal is output from the G pixels, and an Rc image signal is output from the R pixels of the imaging sensor 36.

As illustrated in FIG. 11, in the oxygen saturation mode, when the observation target is illuminated with the first illumination light including the first blue light BL, the green light G, and the red light R in the first frame, the imaging processor 37 outputs a B1 image signal from the B pixels, a G1 image signal from the G pixels, and an R1 image signal from the R pixels of the imaging sensor 36 as a first illumination light image. When the observation target is illuminated with the second illumination light including the second blue light BS, the green light G, and the red light R in the second frame, the imaging processor 37 outputs a B2 image signal from the B pixels, a G2 image signal from the G pixels, and an R2 image signal from the R pixels of the imaging sensor 36 as a second illumination light image.

When the observation target is illuminated with the third illumination light that is the green light G in the third frame, the imaging processor 37 outputs a B3 image signal from the B pixels, a G3 image signal from the G pixels, and an R3 image signal from the R pixels of the imaging sensor 36 as a third illumination light image.

Figure 12:
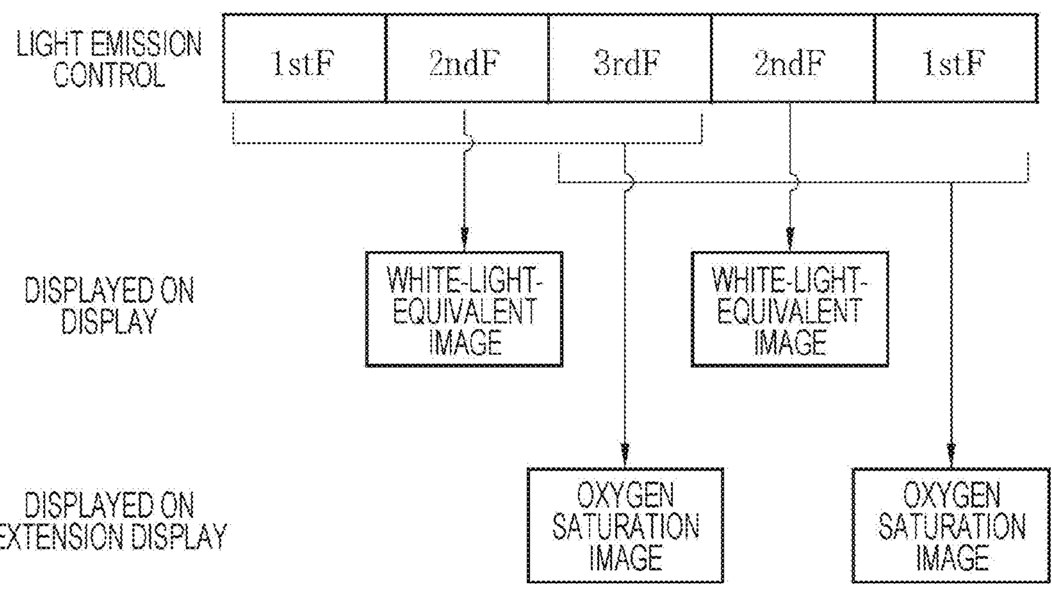
FIG. 12 is an explanatory diagram illustrating light emission control and display control in the oxygen saturation mode or the correction mode.

In the oxygen saturation mode, as illustrated in FIG. 12, the first illumination light is emitted in the first frame (1stF), the second illumination light is emitted in the second frame (2ndF), and the third illumination light is emitted in the third frame (3rdF). Thereafter, the second illumination light in the second frame is emitted, and the first illumination light in the first frame is emitted. A white-light-equivalent image obtained on the basis of emission of the second illumination light in the second frame is displayed on the display 15. Further, an oxygen saturation image obtained in response to emission of the first to third illumination light in the first to third frames is displayed on the extension display 18.

In the oxygen saturation mode, of the image signals for the three frames described above, the B1 image signal included in the first illumination light image, and the G2 image signal and the R2 image signal included in the second illumination light image are used. In the correction mode, to measure the concentration of a specific pigment (such as a yellow pigment) that affects the calculation accuracy of the oxygen saturation, the B3 image signal and the G3 image signal included in the third illumination light image, as well as the B1 image signal, the G2 image signal, and R2 image signal, are used.

Figure 13:
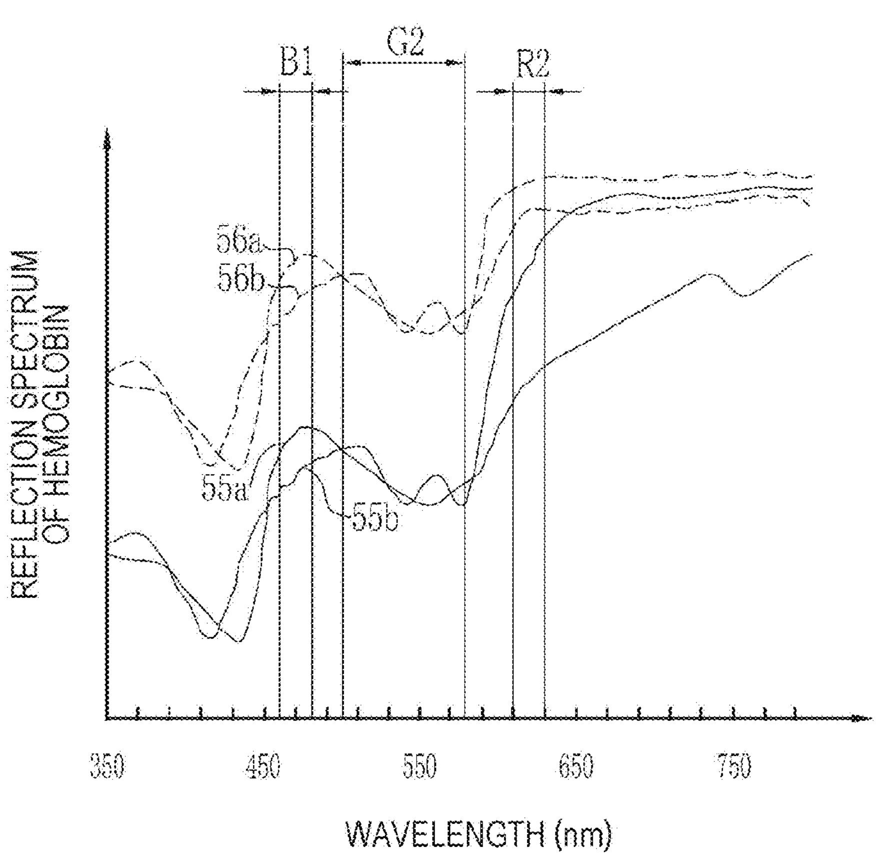
FIG. 13 is a graph illustrating reflection spectra of hemoglobin that differ depending on the blood concentration.

The B1 image signal includes image information related to at least the first blue light BL of the light transmitted through the B color filter BF out of the first illumination light. The B1 image signal (oxygen-saturation image signal) includes, as image information related to the first blue light BL, image information of a wavelength range B1 in which the reflection spectrum changes in accordance with a change in the oxygen saturation of blood hemoglobin. As illustrated in FIG. 13, for example, the wavelength range B1 is preferably a wavelength range from 460 nm to 480 nm including 470 nm at which the difference between the reflection spectra of oxyhemoglobin indicated by curves 55*b* and 56*b* and the reflection spectra of reduced hemoglobin indicated by curves 55*a* and 56*a* is maximized.

In FIG. 13, the curve 55*a* represents the reflection spectrum of reduced hemoglobin at a high blood concentration, and the curve 55*b* represents the reflection spectrum of oxyhemoglobin at a high blood concentration. In contrast, the curve 56*a* represents the reflection spectrum of reduced hemoglobin at a low blood concentration, and the curve 56*b* represents the reflection spectrum of oxyhemoglobin at a low blood concentration.

The G2 image signal includes image information of at least a wavelength range G2 related to the green light G of the light transmitted through the G color filter GF out of the first illumination light. For example, as illustrated in FIG. 13, the wavelength range G2 is preferably a wavelength range from 500 nm to 580 nm. The R2 image signal includes image information of at least a wavelength range R2 related to the red light R of the light transmitted through the R color filter RF out of the first illumination light. For example, as illustrated in FIG. 13, the wavelength range R2 is preferably a wavelength range from 610 nm to 630 nm.

Figure 14:
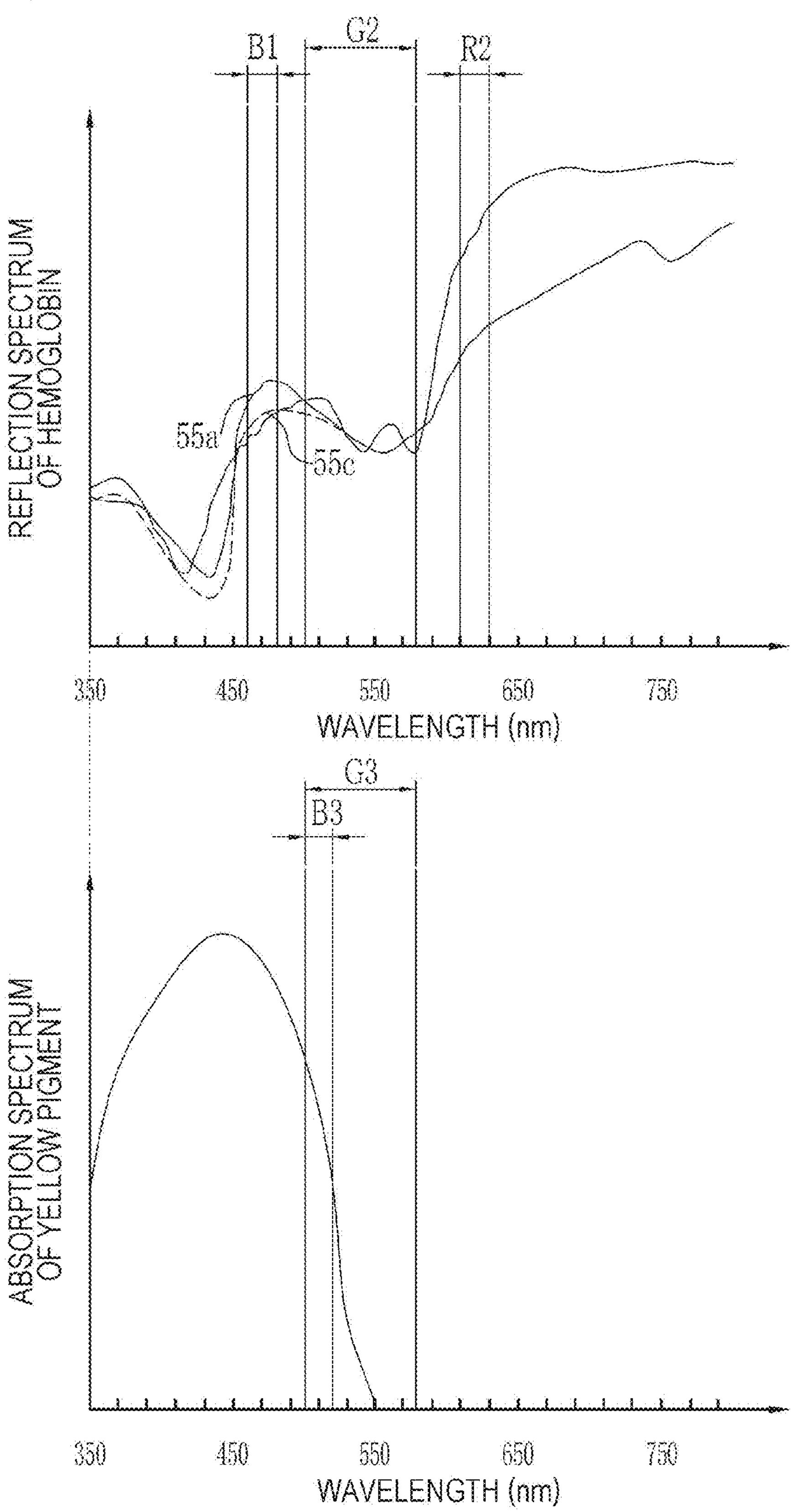
FIG. 14 is a graph illustrating reflection spectra of hemoglobin, which differ depending on the concentration of a yellow pigment, and an absorption spectrum of the yellow pigment.

As illustrated in FIG. 14, the image information of the wavelength range B1 includes image information related to the first blue light BL, and the image information of the wavelength range B3 includes image information related to the green light G. The image information related to the first blue light BL and the image information related to the green light G are image information in which the absorption spectrum of a specific pigment such as a yellow pigment changes in accordance with a change in the concentration of the specific pigment. As the absorption spectrum of the specific pigment changes, the reflection spectrum of hemoglobin also changes. The curve 55*a* represents the reflection spectrum of reduced hemoglobin without the influence of the yellow pigment, and a curve 55*c* represents the reflection spectrum of reduced hemoglobin with the influence of the yellow pigment. As indicated by the curves 55*a* and 55*c*, the reflection spectrum of reduced hemoglobin changes in accordance with the presence or absence of the yellow pigment (the same applies to the reflection spectrum of oxyhemoglobin). Accordingly, in the wavelength range B1 and the wavelength range B3, the reflection spectrum of reduced hemoglobin changes in accordance with a change in the oxygen saturation of blood hemoglobin due to the influence of the specific pigment such as the yellow pigment.

Figures 15, 16:
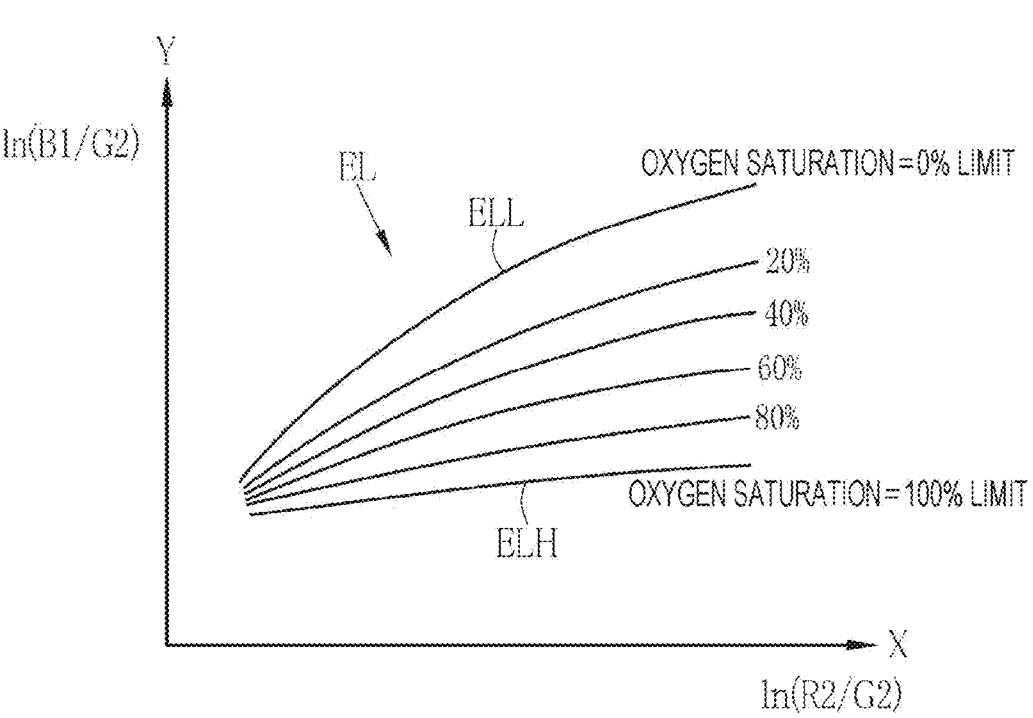
FIG. 15 is a table illustrating oxygen saturation dependence, blood concentration dependence, and brightness dependence of a B1 image signal, a G2 image signal, and an R2 image signal without the influence of the yellow pigment.
FIG. 16 is a graph illustrating contours representing the oxygen saturation.

In an ideal case where the observation target is not affected by a specific pigment such as the yellow pigment with the use of the endoscope 12, as illustrated in FIG. 15, the B1 image signal (denoted by "B1"), the G2 image signal (denoted by "G2"), and the R2 image signal (denoted by "R2") are affected by oxygen saturation dependence, blood concentration dependence, or brightness dependence. As described above, since the B1 image signal includes the wavelength range B1 in which the difference between the reflection spectrum of oxyhemoglobin and the reflection spectrum of reduced hemoglobin is maximized, the oxygen saturation dependence, which changes in accordance with the oxygen saturation, is approximately "high". As indicated by the curves 55*a* and 55*b* and the curves 56*a* and 56*b*, the B1 image signal is approximately "medium" for blood concentration dependence, which changes in accordance with the blood concentration. The B1 image signal has "presence" of brightness dependence, which changes in accordance with the brightness of the observation target. A measure of dependence has "high", "medium", and "low" levels, with the "high" level indicating that the dependence is higher than that of any other image signal, the "medium" level indicating that the dependence is intermediate compared to any other image signal, and the "low" level indicating that the dependence is lower than that of any other image signal.

The G2 image signal has "low" oxygen saturation dependence since the magnitude relationship between the reflection spectrum of oxyhemoglobin and the reflection spectrum of reduced hemoglobin is reversed over a wide wavelength range. As indicated by the curves 55*a* and 55*b* and the curves 56*a* and 56*b*, the G2 image signal has approximately "high" blood concentration dependence. Like the B1 image signal, the G2 image signal has "presence" of brightness dependence.

The R2 image signal is less likely to be changed by the oxygen saturation than the B1 image signal, but has approximately "medium" oxygen saturation dependence. As indicated by the curves 55*a* and 55*b* and the curves 56*a* and 56*b*, the R2 image signal has approximately "low" blood concentration dependence. Like the B1 image signal, the R2 image signal has "presence" of brightness dependence.

As described above, since all of the B1 image signal, the G2 image signal, and the R2 image signal have brightness dependence, the G2 image signal is used as a normalized signal to generate an oxygen saturation calculation table 73 for calculating the oxygen saturation by using a signal ratio ln(B1/G2) obtained by normalizing the B1 image signal by the G2 image signal and a signal ratio ln(R2/G2) obtained by normalizing the R2 image signal by the G2 image signal. The term "In" for the signal ratio ln(B1/G2) is a natural logarithm (the same applies to a signal ratio ln(R2/G2)).

When the relationship between the signal ratios ln(B1/G2) and ln(R2/G2) and the oxygen saturation are represented by two-dimensional coordinates with the signal ratio ln (R2/G2) on the X-axis and the signal ratio ln(B1/G2) on the Y-axis, as illustrated in FIG. 16, the oxygen saturation is represented by contours EL along the Y-axis direction. A contour ELH represents an oxygen saturation of "100%", and a contour ELL represents an oxygen saturation of "0%". The contours are distributed such that the oxygen saturation gradually decreases from the contour ELH to the contour ELL (in FIG. 16, contours for "80%", "60%", "40%", and "20%" are distributed).

The values (signal ratio ln(R2/G2)) on the X-axis and the values (signal ratio ln (B1/G2)) on the Y-axis are affected by the oxygen saturation dependence and the blood concentration dependence. For the brightness dependence, however, as illustrated in FIG. 17, the values on the X-axis and the values on the Y-axis are normalized by the G2 image signal, and are thus determined to have "absence" without being affected by the brightness dependence. The values on the X-axis have approximately "medium" oxygen saturation dependence and approximately "high" blood concentration dependence. In contrast, the values on the Y-axis have approximately "high" oxygen saturation dependence and approximately "medium" blood concentration dependence.

In an actual case where the observation target is affected by a specific pigment such as the yellow pigment with the use of the endoscope 12, by contrast, as illustrated in FIG. 18, the B1 image signal (denoted by "B1"), the G2 image signal (denoted by "G2"), and the R2 image signal (denoted by "R2") are affected by oxygen saturation dependence, blood concentration dependence, yellow pigment dependence, or brightness dependence. The B1 image signal includes image information in which the absorption spectrum of a specific pigment such as the yellow pigment changes in accordance with a change in the concentration of the specific pigment, and is thus approximately "high" for yellow pigment dependence, which changes in accordance with the yellow pigment. In contrast, the G2 image signal is less likely to be changed by the yellow pigment than the B1 image signal and thus has approximately "low to medium" yellow pigment dependence. The R1 image signal is less likely to be changed by the yellow pigment and thus has approximately "low" yellow pigment dependence.

When the signal ratio ln(R2/G2) and the signal ratio ln(B1/G2) are represented by two-dimensional coordinates with the signal ratio ln(R2/G2) on the X-axis and the signal ratio ln(B1/G2) on the Y-axis, even when the observation target has the same oxygen saturation, as illustrated in FIG. 19, an oxygen saturation StO2A in the absence of the yellow pigment and an oxygen saturation StO2B in the presence of the yellow pigment are represented differently. The oxygen saturation of StO2B is apparently shifted to be higher than the oxygen saturation of StO2A due to the presence of the yellow pigment.

Accordingly, for accurate calculation of the oxygen saturation also in the case of yellow pigment dependence, the B3 image signal and the G3 image signal included in the third illumination light image are used to calculate the oxygen saturation. The B3 image signal includes image information related to light transmitted through the B color filter BF out of the third illumination light. The B3 image signal (specific pigment image signal) includes image information of the wavelength range B3 having sensitivity to a specific pigment other than hemoglobin, such as the yellow pigment (see FIG. 14). The B3 image signal is less sensitive to the specific pigment than the B1 image signal, but has a certain degree of sensitivity to the specific pigment. Accordingly, as illustrated in FIG. 20, the B1 image signal has "high" yellow pigment dependence, whereas the B3 image signal has approximately "medium" yellow pigment dependence. The B3 image signal has "low" oxygen saturation dependence, "high" blood concentration dependence, and "presence" of brightness dependence.

The G3 image signal also includes an image signal in the wavelength range B3 that is less sensitive to the specific pigment than the G3 image signal but has a certain degree of sensitivity to the specific pigment (see FIG. 14). Accordingly, the G3 image signal has approximately "low to medium" yellow pigment dependence. The G3 image signal has "low" oxygen saturation dependence, "high" blood concentration dependence, and "presence" of brightness dependence. Since the B2 image signal also has "high" yellow pigment dependence, the B2 image signal may be used instead of the B3 image signal to calculate the oxygen saturation. The B2 image signal has "low" oxygen saturation dependence, "high" blood concentration dependence, and "presence" of brightness dependence.

Figure 21:
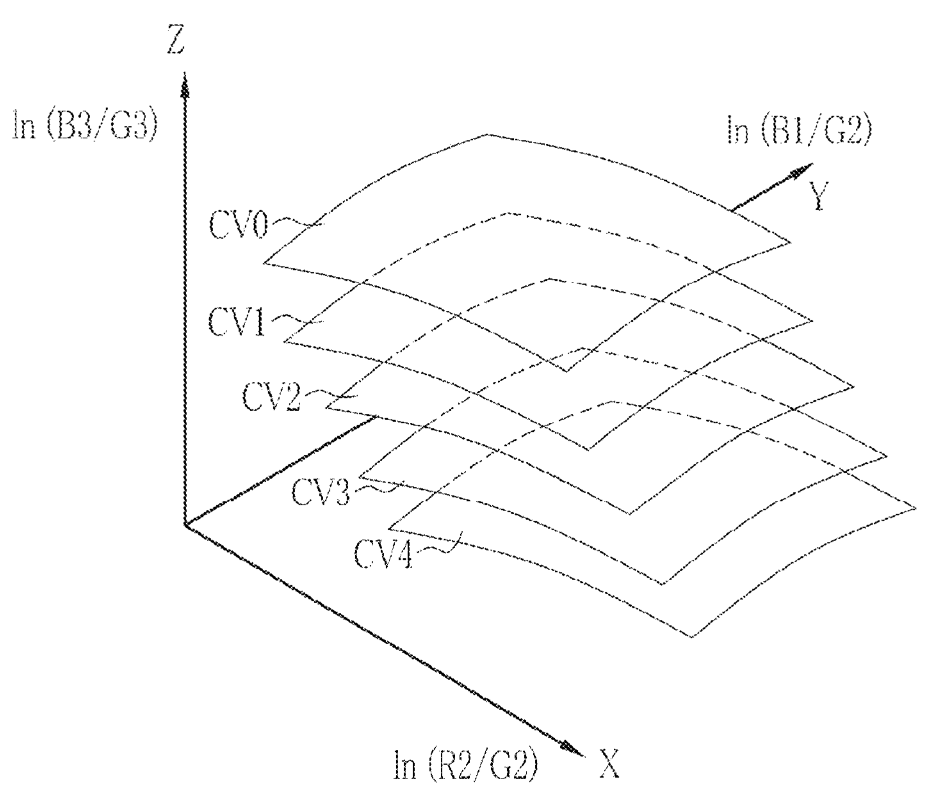
FIG. 21 is a graph illustrating curved surfaces representing the oxygen saturation in accordance with the yellow pigment.

When the relationship between the signal ratios ln(B1/G2) and ln(R2/G2), the yellow pigment, and the oxygen saturation are represented by three-dimensional coordinates with the signal ratio ln(R2/G2) on the X-axis, the signal ratio ln(B1/G2) on the Y-axis, and a signal ratio ln(B3/G3) on the Z-axis, as illustrated in FIG. 21, curved surfaces CV0 to CV4 representing the oxygen saturation are distributed in the Z-axis direction in accordance with the pigment concentration of the yellow pigment. The curved surface CV0 represents the oxygen saturation when the yellow pigment has a concentration of "0" (no influence of the yellow pigment). The curved surfaces CV1 to CV4 represent the oxygen saturations when the yellow pigment has concentrations of "1" to "4", respectively. The concentration having a larger value indicates a higher concentration of the yellow pigment. As indicated by the curved surfaces CV0 to CV4, the values on the Z-axis change so as to decrease as the concentration of the yellow pigment increases.

As illustrated in FIG. 22A, when the state of the oxygen saturation represented by three-dimensional coordinates of X, Y, and Z is represented by two-dimensional coordinates of X and Y, as illustrated in FIG. 22B, regions AR0 to AR4 representing the respective states of the oxygen saturations are distributed at different positions in accordance with the concentration of the yellow pigment. The regions AR0 to AR4 represent the distributions of the oxygen saturations when the yellow pigment has concentrations of "0" to "4", respectively. For each of the regions AR0 to AR4, contours EL indicating the oxygen saturations are determined, thereby making it possible to determine an oxygen saturation corresponding to the concentration of the yellow pigment (see FIG. 16). As indicated by the regions AR0 to AR4, as the concentration of the yellow pigment increases, the values on the X-axis increase and the values on the Y-axis decrease.

As illustrated in FIG. 23, the values on the X-axis (the signal ratio ln(R2/G2)), the values on the Y-axis (the signal ratio ln(B1/G2)), and the values on the Z-axis (the signal ratio ln(B3/G3)) are subject to yellow pigment dependence. The yellow pigment dependence for the values on the X-axis is "low to medium", the yellow pigment dependence for the values on the Y-axis is "high", and the yellow pigment dependence for the values on the Z-axis is "medium". The values on the Z-axis have "low to medium" oxygen saturation dependence and "low to medium" blood concentration dependence. The values on the Z-axis are normalized by the G3 image signal and thus have "absence" of the brightness dependence.

Figure 24:
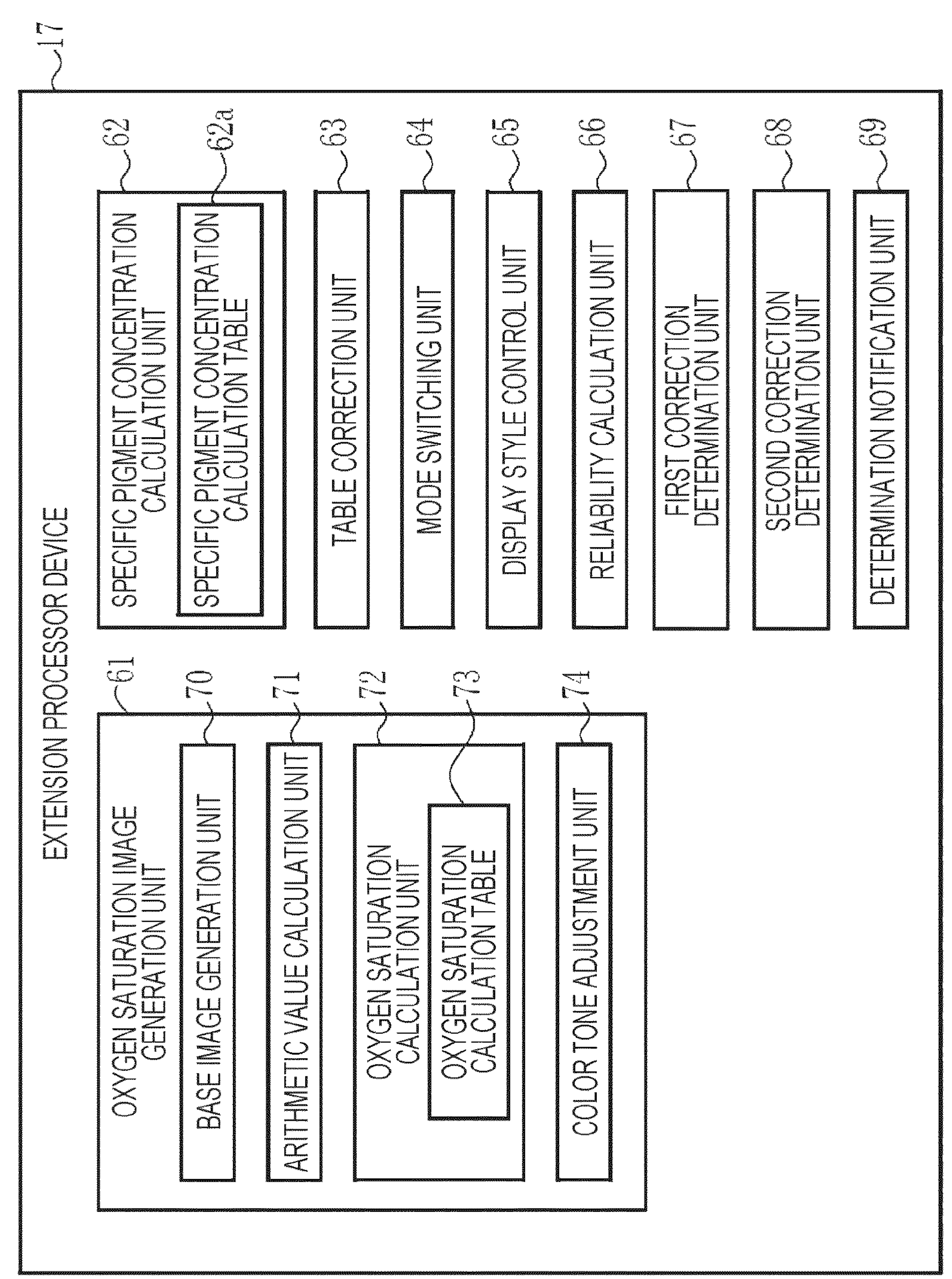
FIG. 24 is a block diagram illustrating functions of an image processing unit.

As illustrated in FIG. 24, the extension processor device 17 includes an oxygen saturation image generation unit 61, a specific pigment concentration calculation unit 62, a table correction unit 63, a mode switching unit 64, a display style control unit 65, a reliability calculation unit 66, a first correction determination unit 67, a second correction determination unit 68, and a determination notification unit 69. In the extension processor device 17, programs related to various types of processing are incorporated in a program memory (not illustrated). A central control unit (not illustrated), which is constituted by a processor, executes a program in the program memory to implement the functions of the oxygen saturation image generation unit 61, the specific pigment concentration calculation unit 62, the table correction unit 63, the mode switching unit 64, the display style control unit 65, the reliability calculation unit 66, the first correction determination unit 67, the second correction determination unit 68, and the determination notification unit 69.

The oxygen saturation image generation unit 61 includes a base image generation unit 70, an arithmetic value calculation unit 71, an oxygen saturation calculation unit 72, the oxygen saturation calculation table 73, and a color tone adjustment unit 74. The base image generation unit 70 generates a base image on the basis of the image signals from the processor device 14. The base image is preferably an image from which form information such as the shape of the observation target can be grasped. The base image is constituted by a B2 image signal, a G2 image signal, and an R2 image signal. The base image may be a narrow-band light image in which a blood vessel, a structure (gland duct structure), or the like is highlighted by narrow-band light or the like.

The arithmetic value calculation unit 71 calculates arithmetic values by arithmetic processing based on the B1 image signal, the G2 image signal, and the R2 image signal included in the oxygen-saturation image signal. Specifically, the arithmetic value calculation unit 71 calculates a signal ratio B1/G2 between the B1 image signal and the G2 image signal and a signal ratio R2/G2 between the R2 image signal and the G2 image signal as arithmetic values to be used for the calculation of the oxygen saturation. The signal ratio B1/G2 and the signal ratio R2/G2 are each preferably converted into a logarithm (In). Alternatively, color difference signals Cr and Cb, or a saturation S, a hue H, or the like calculated from the B1 image signal, the G2 image signal, and the R2 image signal may be used as the arithmetic values.

The oxygen saturation calculation unit 72 refers to the oxygen saturation calculation table 73 and calculates the oxygen saturation on the basis of the arithmetic values. The oxygen saturation calculation table 73 stores correlations between the signal ratios B1/G2 and R2/G2, each of which is one of the arithmetic values, and the oxygen saturation. When the correlations are represented by two-dimensional coordinates with the signal ratio ln(B1/G2) on the vertical axis and the signal ratio ln(R2/G2) on the horizontal axis, the states of the oxygen saturations are represented by contours EL extending in the horizontal-axis direction, and the contours EL for different oxygen saturations are distributed at different positions in the vertical-axis direction (see FIG. 16).

Figure 25:
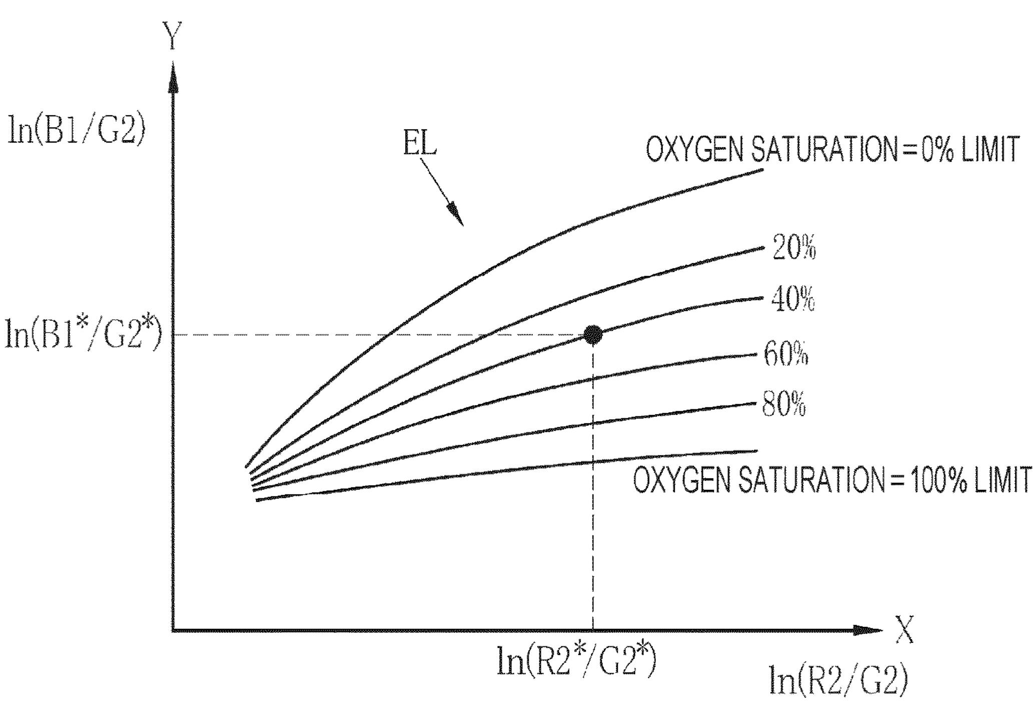
FIG. 25 is an explanatory diagram illustrating a method for calculating the oxygen saturation.

The oxygen saturation calculation unit 72 refers to the oxygen saturation calculation table 73 and calculates, for each pixel, an oxygen saturation corresponding to the signal ratios B1/G2 and R2/G2. For example, as illustrated in FIG. 25, when a specific pixel has signal ratios ln(B1*/G2*) and ln(R2*/G2*), an oxygen saturation corresponding to the signal ratios ln (B1*/G2*) and ln(R2*/G2*) is "40%".

Accordingly, the oxygen saturation calculation unit 72 calculates the oxygen saturation of the specific pixel as "40%".

The color tone adjustment unit 74 performs composite color processing for changing the color tone of the base image by using the oxygen saturation calculated by the oxygen saturation calculation unit 72 to generate an oxygen saturation image. The color tone adjustment unit 74 maintains the color tone of a region of the base image where the oxygen saturation exceeds a threshold value, and changes the color tone of a region of the base image where the oxygen saturation is less than or equal to the threshold value to a color tone that changes in accordance with the oxygen saturation. Accordingly, the color tone of a normal site having an oxygen saturation exceeding the threshold value is maintained, whereas only the color tone of an abnormal site having a low oxygen saturation equal to or less than the threshold value is changed. This makes it possible to grasp the oxygen state of the abnormal site in a situation that allows observation of the form information of the normal site.

The color tone adjustment unit 74 may generate an oxygen saturation image by pseudo-color processing in which colors corresponding to the oxygen saturations are assigned regardless of the magnitude of the oxygen saturations. The pseudo-color processing does not require the base image.

In the correction mode, the specific pigment concentration calculation unit 62 calculates a specific pigment concentration on the basis of a specific pigment image signal including image information of a wavelength range having sensitivity to a specific pigment other than blood hemoglobin among pigments included in the observation target. Examples of the specific pigment include a yellow pigment such as bilirubin. The specific pigment image signal preferably includes at least the B3 image signal. Specifically, the specific pigment concentration calculation unit 62 calculates the signal ratios ln(B1/G2), ln(G2/R2), and ln(B3/G3). Then, the specific pigment concentration calculation unit 62 refers to a specific pigment concentration calculation table 62*a* to calculate specific pigment concentrations corresponding to the signal ratios ln(B1/G2), ln(G2/R2), and ln(B3/G3).

The specific pigment concentration calculation table 62*a* stores correlations between the signal ratios ln(B1/G2), ln(G2/R2), and ln(B3/G3) and the specific pigment concentrations. For example, the range of the signal ratios ln(B1/G2), ln(G2/R2), and ln(B3/G3) is divided into five stages. In this case, the specific pigment concentrations "0" to "4" are stored in the specific pigment concentration calculation table 62*a* in association with the signal ratios ln (B1/G2), ln(G2/R2), and ln(B3/G3) in the ranges in the five stages, respectively. A signal ratio B3/G3 converted into a logarithm (In) is preferably used.

The table correction unit 63 performs, as the correction processing to be performed in the correction mode, table correction processing for correcting the oxygen saturation calculation table 73 on the basis of the specific pigment concentration. The table correction processing corrects the correlations between the signal ratios B1/G2 and R2/G2 and the oxygen saturations, which are stored in the oxygen saturation calculation table 73. Specifically, for the specific pigment concentration "2", as illustrated in FIG. 26, the table correction unit 63 generates contours EL indicating the states of the oxygen saturations in a region AR2 corresponding to the specific pigment concentration "2" among regions AR0 to AR4 determined in accordance with the specific pigment concentrations. The table correction unit 63 corrects the oxygen saturation calculation table 73 so as to obtain the generated contours EL.

Figures 27, 28:
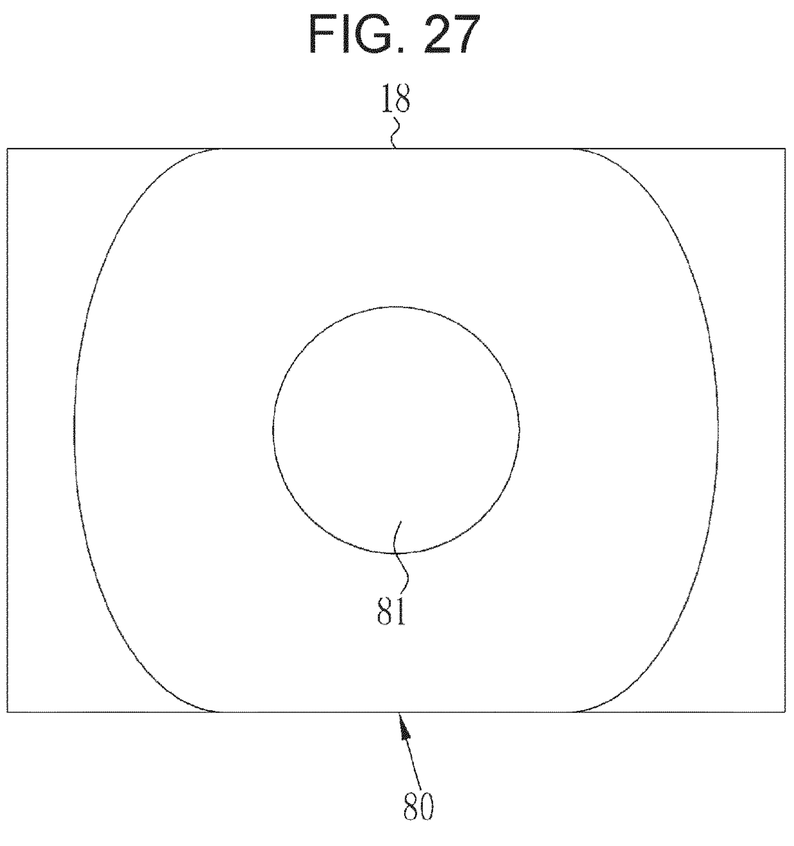
FIG. 27 is an image diagram of the display that displays a correction image and a specific region.
FIG. 28 is a graph illustrating a relationship between a pixel value and reliability.

In this embodiment, in the correction mode, as illustrated in FIG. 27, a correction image 80 is displayed on the extension display 18, and a specific region 81 to be used to calculate a specific pigment concentration is displayed in the correction image 80. The specific region 81 may have a circular shape, an elliptic shape, a rectangular shape, or any other shape. The specific region 81 is preferably located in the center of the screen, but may be located at any other position. While observing the correction image, the user operates the endoscope 12 so that a region suitable for correction of the oxygen saturation calculation table 73 falls within the specific region 81. When a region appropriate for correction falls within the specific region 81, the user performs a correction operation by using the processor-side user interface 16 or the scope-side user interface 19. The table correction unit 63 corrects the oxygen saturation calculation table 73 by using a specific pigment concentration in the specific region at the timing when the correction operation is performed. The specific pigment concentration in the specific region is preferably the average value of the specific pigment concentrations of the respective pixels in the specific region, or is preferably a weighted average value obtained by weighting the specific pigment concentrations in accordance with reliability calculated by the reliability calculation unit 66 described below.

In this embodiment, correction support is performed to clearly display, as the region suitable for correction of the oxygen saturation calculation table 73, an appropriate correction region less affected by disturbance affecting the calculation of the oxygen saturation and to allow the user to select the appropriate correction region by a correction operation. The details of the correction support will be described below.

The mode switching unit 64 switches between the oxygen saturation mode and the correction mode in accordance with the user operating the mode switch 12*f*. When the mode is switched to the oxygen saturation mode, the oxygen saturation image generation unit 61 generates an oxygen saturation image. When the mode is switched to the correction mode, a correction operation for performing the correction processing is made acceptable, and the correction processing is executed in accordance with the correction operation.

Correction support in the correction mode will be described below. When the mode is switched to the correction mode, the correction image 80 is displayed on the extension display 18, and the specific region 81, which is used to calculate a specific pigment concentration, is displayed on the extension display 18 (see FIG. 27). The display style control unit 65 performs at least one of changing the display style of the correction image so as to allow the user to select an appropriate correction region by a correction operation or changing the display style of the specific region in accordance with the reliability related to the calculation of the oxygen saturation. The correction image is preferably a color image constituted by the B1 image signal, the G1 image signal, and the R1 image signal, but may be any other image.

In some cases, a residue, bleeding, fat, residual liquid, or mucus may be thinly present on the mucous membrane or may be difficult to visually recognize in the white-light-equivalent image, and accordingly, it may be difficult to determine whether it is possible to appropriately perform the correction processing. In such a case, the display style control unit 65 preferably generates a correction image described below, regardless of the magnitude of the reliability described below. For example, to facilitate visual recognition of a residue, bleeding, fat, residual liquid, or mucus, the display style control unit 65 preferably emphasizes the saturation of an image such as a white-light-equivalent image to generate a correction image. To further darken a dark portion having insufficient signal intensity, such as the lumen, the display style control unit 65 preferably reduces the luminance of the dark portion to generate a correction image.

The display style of the correction image may be changed in accordance with the reliability. Specifically, the display style control unit 65 changes the display style of the correction image 80 so that a difference between a low-reliability region having low reliability and a high-reliability region having high reliability for the calculation of the oxygen saturation is emphasized. The reliability indicates the calculation accuracy of the oxygen saturation for each pixel, with higher reliability indicating higher calculation accuracy of the oxygen saturation. The low-reliability region is a region having reliability less than a reliability threshold value. The high-reliability region is a region having reliability greater than or equal to the reliability threshold value. In the correction image, emphasizing the difference between the low-reliability region and the high-reliability region enables the specific region to include the high-reliability region while avoiding the low-reliability region.

The reliability is calculated by the reliability calculation unit 66. Specifically, the reliability calculation unit 66 calculates at least one reliability that affects the calculation of the oxygen saturation on the basis of the B1 image signal, the G1 image signal, and the R1 image signal included in the first illumination light image or the B2 image signal, the G2 image signal, and the R2 image signal included in the second illumination light image. The reliability is represented by, for example, a decimal number between 0 and 1. In a case where the reliability calculation unit 66 calculates a plurality of types of reliabilities, the reliability of each pixel is preferably the minimum reliability among the plurality of types of reliabilities.

For example, for a brightness value that affects the calculation accuracy of the oxygen saturation, as illustrated in FIG. 28, the reliability for a brightness value of a G2 image signal outside a certain range Rx is lower than the reliability for a brightness value of a G2 image signal within the certain range Rx. The case of being outside the certain range Rx is a case of a high brightness value such as halation, or is a case of a very low brightness value such as in a dark portion. As described above, the calculation accuracy of the oxygen saturation is low for a brightness value outside the certain range Rx, and the reliability is also low accordingly. The G1 image signal may be used instead of the G2 image signal to calculate the reliability.

Figure 29:
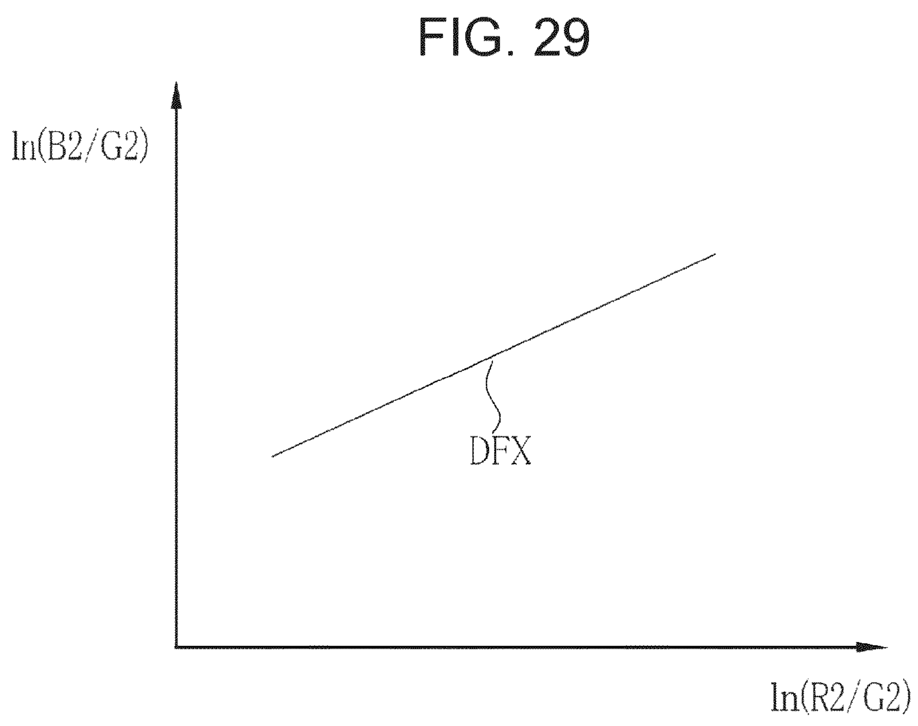
FIG. 29 is a graph illustrating a two-dimensional plane for representing a relationship between bleeding and reliability.

The calculation accuracy of the oxygen saturation is affected by a disturbance, examples of which includes at least bleeding, fat, a residue, mucus, or a residual liquid, and such a disturbance may also cause a variation in reliability. For bleeding, which is one of the disturbances described above, as illustrated in FIG. 29, the reliability is determined in accordance with a distance from a definition line DFX in a two-dimensional plane defined by a vertical axis ln(B2/G2) and a horizontal axis ln(R2/G2). As the distance from the definition line DFX to coordinates plotted on the two-dimensional plane on the basis of the B2 image signal, the G2 image signal, and the R2 image signal increases, the reliability decreases. For example, the closer the coordinates plotted on the two-dimensional plane are to the lower right, the lower the reliability. In FIG. 29, In denotes the natural logarithm. B2/G2 denotes the signal ratio of the B2 image signal to the G2 image signal, and R2/G2 denotes the signal ratio of the R2 image signal to the G2 image signal.

Figure 30:
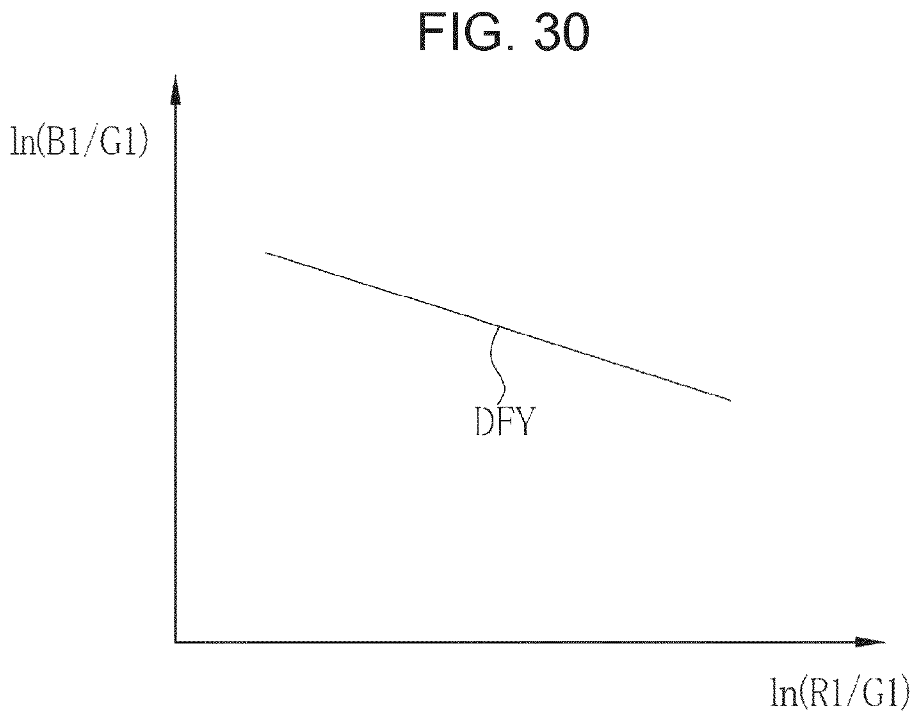
FIG. 30 is a graph illustrating a two-dimensional plane for representing a relationship between fat, a residue, mucus, or a residual liquid and reliability.

For fat, a residue, a residual liquid, or mucus, which is included in the disturbances described above, as illustrated in FIG. 30, the reliability is determined in accordance with a distance from a definition line DFY in a two-dimensional plane defined by a vertical axis ln (B1/G1) and a horizontal axis ln(R1/G1). As the distance from the definition line DFY to coordinates plotted on the two-dimensional plane on the basis of the B1 image signal, the G1 image signal, and the R1 image signal increases, the reliability decreases. For example, the closer the coordinates plotted on the two-dimensional plane are to the lower left, the lower the reliability. In FIG. 30, In denotes the natural logarithm. B1/G1 denotes the signal ratio of the B1 image signal to the G1 image signal, and R1/G1 denotes the signal ratio of the R1 image signal to the G1 image signal.

Figure 31:
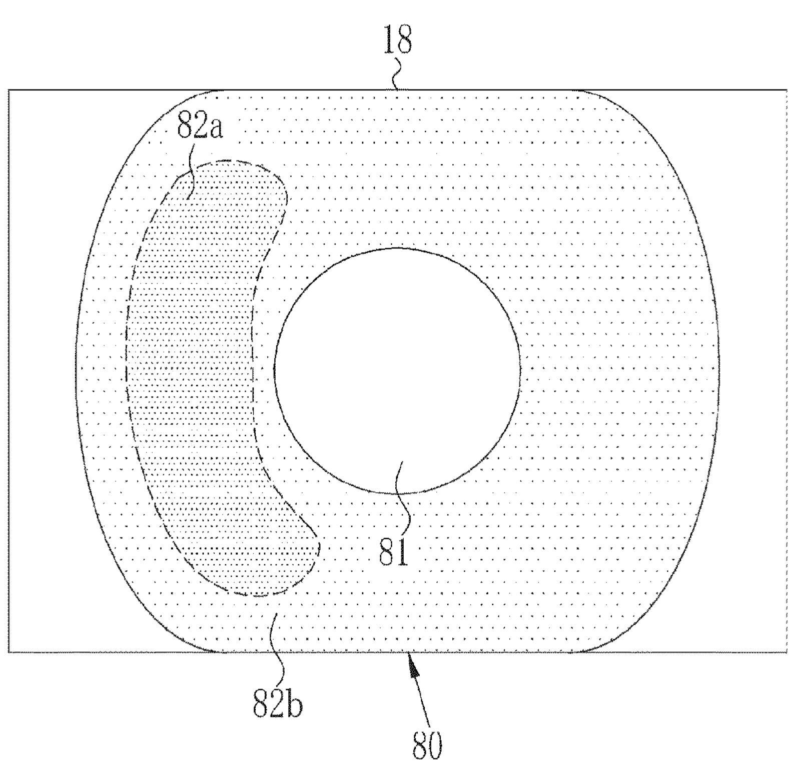
FIG. 31 is an image diagram of the display that displays a low-reliability region and a high-reliability region having different saturations.

In one method by which the display style control unit 65 emphasizes a difference between a low-reliability region and a high-reliability region, as illustrated in FIG. 31, the display style control unit 65 sets the saturation of a low-reliability region 82*a* to be higher than the saturation of a high-reliability region 82*b*. This allows the user to easily select the high-reliability region 82*b* as the specific region 81 while avoiding the low-reliability region 82*a*. Further, the display style control unit 65 reduces the luminance of a dark portion BA in the low-reliability region 82*a*. This allows the user to easily avoid the dark portion BA when selecting the specific region 81. The dark portion is a dark region having a brightness value less than or equal to a certain value. The low-reliability region 82*a* and the high-reliability region 82*b* may have opposite colors.

Figure 32:
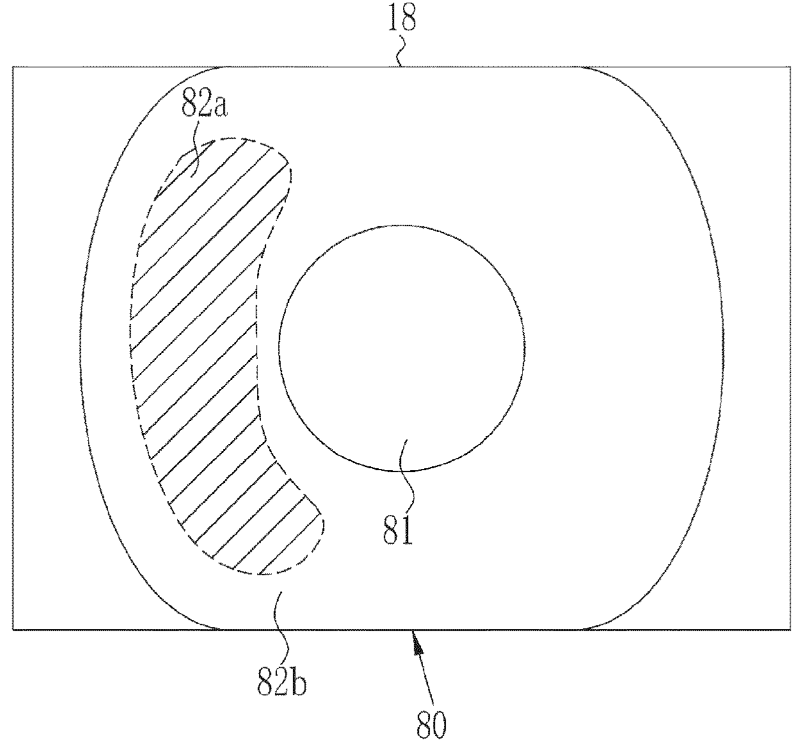
FIG. 32 is an image diagram of the display that displays the low-reliability region with a region highlighting line superimposed thereon.

Preferably, the display style control unit 65 performs at least one of superimposing a region highlighting line on the low-reliability region 82*a* or displaying the low-reliability region 82*a* in monochrome. For example, as illustrated in FIG. 32, the low-reliability region 82*a* preferably has diagonal lines superimposed thereon at regular intervals as region highlighting lines. This allows the user to easily select the high-reliability region 82*b* as the specific region 81 while avoiding the low-reliability region 82*a*. While the region highlighting lines are diagonal lines spaced at constant intervals, the diagonal lines may be spaced at intervals that are changed in accordance with the reliability.

The display style control unit 65 preferably changes the display style of the specific region in accordance with the reliability in the specific region. In the correction mode, before the correction operation is performed, the first correction determination unit 67 determines whether it is possible to appropriately perform correction processing on the basis of the reliability in the specific region. If the number of effective pixels having reliability greater than or equal to the reliability threshold value among the pixels in the specific region is greater than or equal to a certain value, the first correction determination unit 67 determines that it is possible to appropriately perform the correction processing. On the other hand, if the number of effective pixels among the pixels in the specific region is less than the certain value, the first correction determination unit 67 determines that it is not possible to appropriately perform the correction processing. The first correction determination unit 67 preferably performs the determination each time an image is acquired and the reliability is calculated until a correction operation is performed. The period in which the determination is performed may be changed as appropriate.

Figures 33A, 33B, 34:
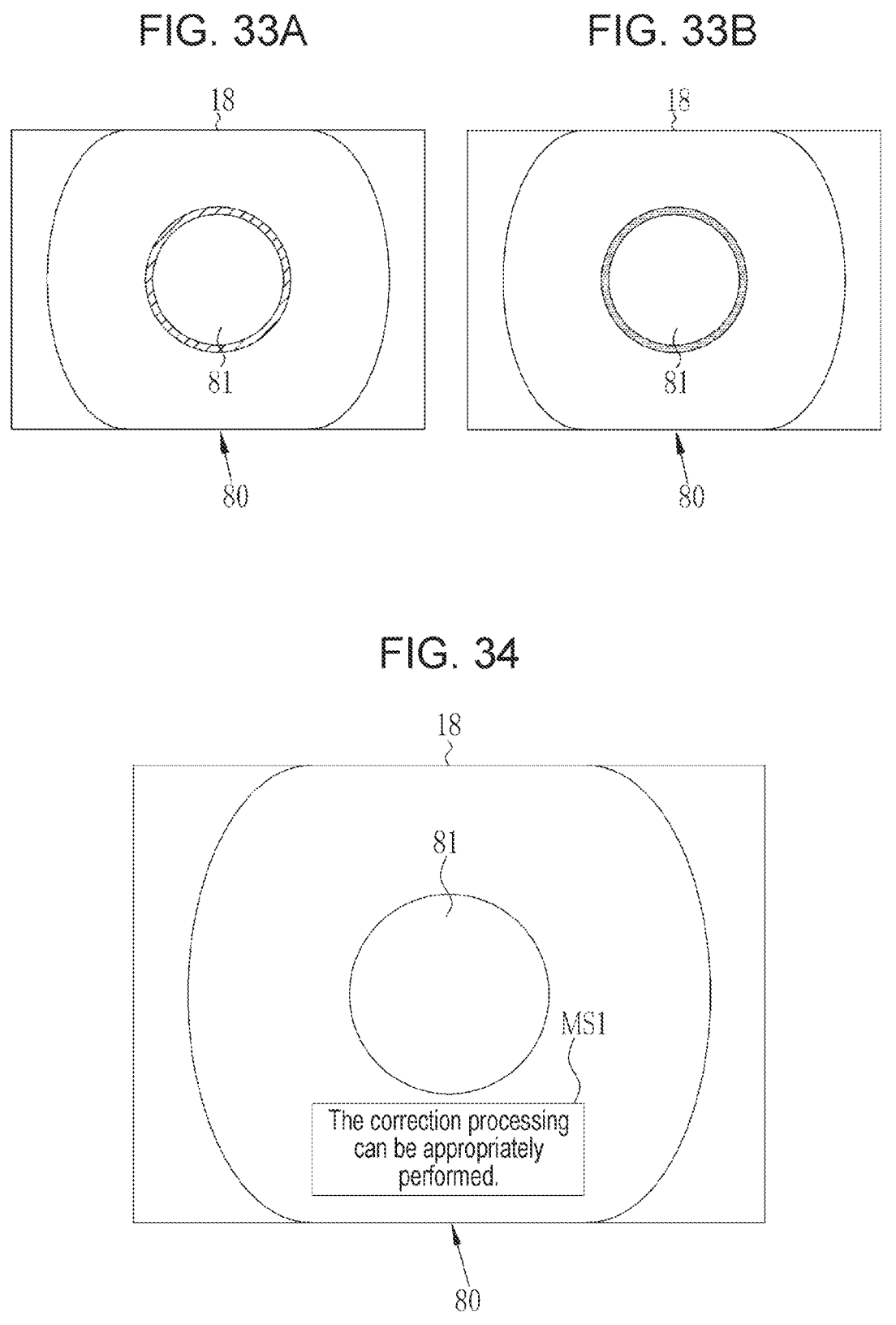

The display style control unit 65 preferably makes the display style of the specific region different between a case where the first correction determination unit 67 determines that it is possible to appropriately perform the correction processing and a case where the first correction determination unit 67 determines that it is not possible to appropriately perform the correction processing. For example, as illustrated in FIG. 33A, if the first correction determination unit 67 determines that it is possible to appropriately perform the correction processing, the specific region 81 is highlighted in a first color. On the other hand, as illustrated in FIG. 33B, if the first correction determination unit 67 determines that it is not possible to appropriately perform the correction processing, the specific region 81 is highlighted in a second color different from the first color. The first color and the second color are preferably opposite colors to facilitate understanding of the appropriateness.

In the correction mode, after the correction operation has been performed, by contrast, the second correction determination unit 68 determines whether it is possible to appropriately perform correction processing on the basis of the reliability in the specific region at the timing when the correction operation was performed. The second correction determination unit 68 performs the determination in a manner similar to that of the first correction determination unit 67. The determination notification unit 69 provides a notification related to the determination made by the second correction determination unit 68.

If the second correction determination unit 68 determines that it is possible to appropriately perform the correction processing, the determination notification unit 69 provides a notification indicating that it is possible to appropriately perform the correction processing. For example, as illustrated in FIG. 34, a message MS1 such as "The correction processing can be appropriately performed" is displayed on the extension display 18. In this case, the table correction unit 63 performs, as the correction processing, table correction processing on the basis of the specific pigment concentration in the specific region.

Figure 35:
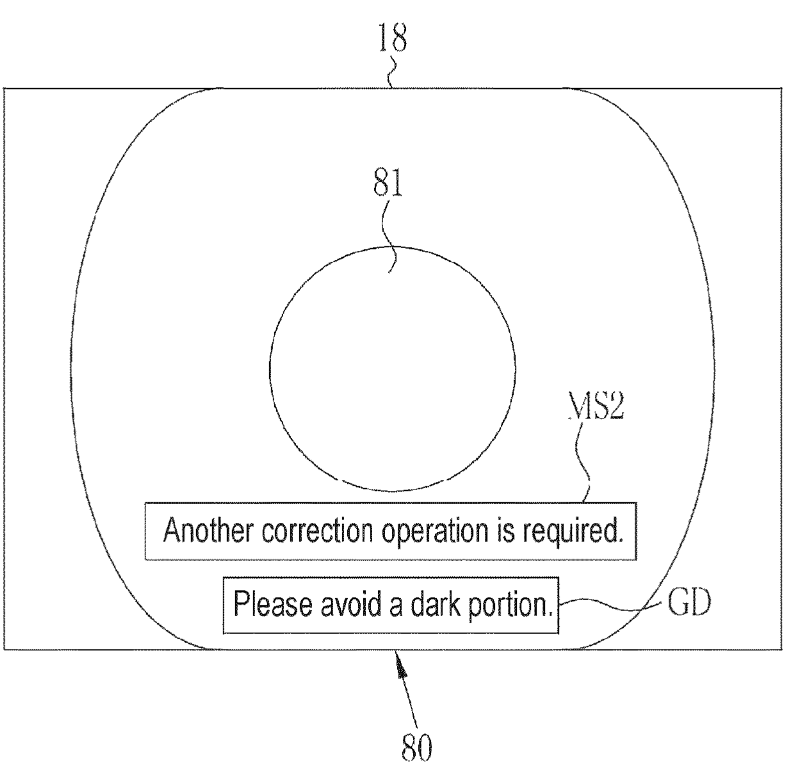
FIG. 35 is an image diagram of the display when it is determined that it is not possible to appropriately perform the table correction processing.

On the other hand, if the second correction determination unit 68 determines that it is not possible to appropriately perform the correction processing, the determination notification unit 69 provides a notification indicating that another correction operation is required since it is not possible to appropriately perform the correction processing. For example, as illustrated in FIG. 35, a message MS2 such as "Another correction operation is required" is displayed on the extension display 18. In this case, in addition to or instead of the message MS2, the determination notification unit 69 preferably provides a notification of operational guidance GD for performing appropriate table correction processing. Preferable examples of the operational guidance GD to be displayed on the extension display 18 include operational guidance such as "Please avoid a dark portion". Other examples of the operational guidance include operational guidance such as "Please avoid bleeding, a residual liquid, fat, and so on".

Next, the flow of a series of operations in the correction mode will be described with reference to a flowchart in FIG. 36. In response to the user operating the mode switch 12*f*, the mode is switched to the correction mode. In the correction mode, the correction image 80 and the specific region 81 are displayed on the extension display 18 when the mode is switched to the correction mode. In addition, the correction processing related to oxygen saturation calculation is made executable on the basis of the specific pigment concentration of a specific pigment other than blood hemoglobin included in the specific region 81.

In the correction mode, the selection of a specific region by the user is facilitated by performing at least one of changing the display style of the correction image 80 or changing the display style of the specific region 81 in accordance with the reliability related to the calculation of the oxygen saturation. When an appropriate correction region less affected by disturbance affecting the calculation of the oxygen saturation falls within the specific region 81, the user performs a correction operation by using the processor-side user interface 16 or the scope-side user interface 19. The correction processing is performed on the basis of the specific pigment concentration in the specific region at the timing when the correction operation is performed. When the correction processing is completed, the mode is switched to the oxygen saturation mode manually or automatically.

Second Embodiment

Figure 37:
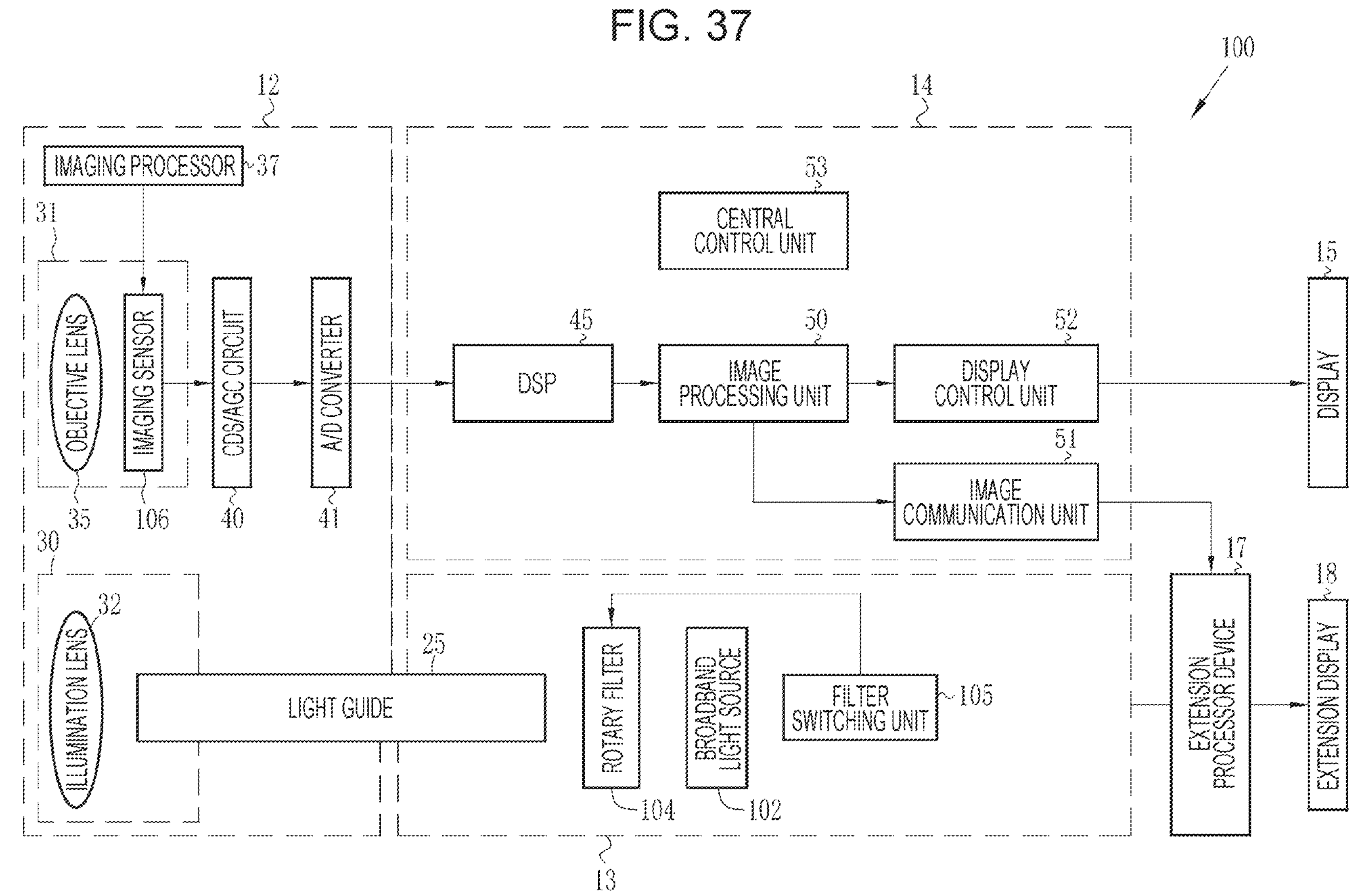
FIG. 37 is a block diagram illustrating functions of an endoscope system according to a second embodiment.

In a second embodiment, in place of the LEDs 20*a* to 20*e* described in the first embodiment, a broadband light source such as a xenon lamp and a rotary filter may be used to illuminate the observation target. In this case, as illustrated in FIG. 37, in an endoscope system 100, the light source device 13 is provided with a broadband light source 102, a rotary filter 104, and a filter switching unit 105 in place of the LEDs 20*a* to 20*e*. The imaging optical system 31 is provided with, in place of the color imaging sensor 36, a monochrome imaging sensor 106 without a color filter. The other elements are similar to those of the endoscope system 10 described above.

The broadband light source 102 is a xenon lamp, a white LED, or the like, and emits white light having a wavelength range ranging from blue to red. The rotary filter 104 includes an inner filter 108 disposed on the inner side and an outer filter 109 disposed on the outer side (see FIG. 38). The filter switching unit 105 is configured to move the rotary filter 104 in the radial direction. When the normal mode is set by the mode switch 12*f*, the filter switching unit 105 inserts the inner filter 108 of the rotary filter 104 into the optical path of white light. When the oxygen saturation mode or the correction mode is set by the mode switch 12*f*, the filter switching unit 105 inserts the outer filter 109 of the rotary filter 104 into the optical path of white light.

Figure 38:
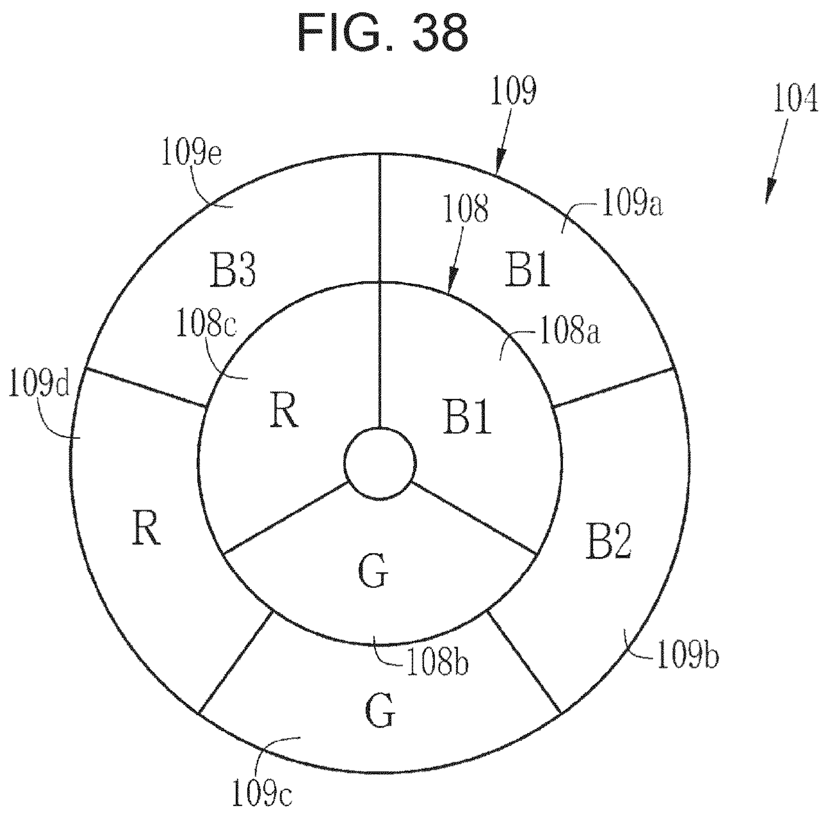
FIG. 38 is a plan view of a rotary filter.

As illustrated in FIG. 38, the inner filter 108 is provided with, in the circumferential direction thereof, a B1 filter 108*a* that transmits the violet light V and the second blue light BS of the white light, a G filter 108*b* that transmits the green light G of the white light, and an R filter 108*c* that transmits the red light R of the white light. Accordingly, in the normal mode, as the rotary filter 104 rotates, the observation target is alternately irradiated with the violet light V, the second blue light BS, the green light G, and the red light R.

The outer filter 109 is provided with, in the circumferential direction thereof, a B1 filter 109*a* that transmits the first blue light BL of the white light, a B2 filter 109*b* that transmits the second blue light BS of the white light, a G filter 109*c* that transmits the green light G of the white light, an R filter 109*d* that transmits the red light R of the white light, and a B3 filter 109*e* that transmits blue-green light BG having a wavelength range B3 of the white light. Accordingly, in the oxygen saturation mode, as the rotary filter 104 rotates, the observation target is alternately irradiated with the first blue light BL, the second blue light BS, the green light G, the red light R, and the blue-green light BG.

In the endoscope system 100, in the normal mode, each time the observation target is illuminated with the violet light V, the second blue light BS, the green light G, and the red light R, imaging of the observation target is performed by the monochrome imaging sensor 106. As a result, a Bc image signal, a Gc image signal, and an Rc image signal are obtained. Then, a white-light image is generated on the basis of the image signals of the three colors in a manner similar to that in the first embodiment described above.

In the oxygen saturation mode or the correction mode, by contrast, each time the observation target is illuminated with the first blue light BL, the second blue light BS, the green light G, the red light R, and the blue-green light BG, imaging of the observation target is performed by the monochrome imaging sensor 106. As a result, a B1 image signal, a B2 image signal, a G2 image signal, an R2 image signal, and a B3 image signal are obtained. The oxygen saturation mode or the correction mode is performed on the basis of the image signals of the five colors in a manner similar to that of the first embodiment. In the second embodiment, however, a signal ratio ln(B3/G2) is used instead of the signal ratio ln(B3/G3).

In the first and second embodiments described above, table correction processing for correcting the oxygen saturation calculation table 73 is performed as the correction processing related to the calculation of the oxygen saturation in the correction mode. Alternatively, calculation value correction processing for adding or subtracting a correction value obtained from the specific pigment concentration to or from the oxygen saturation calculated on the basis of the oxygen saturation calculation table 73 may be performed.

Figure 39:
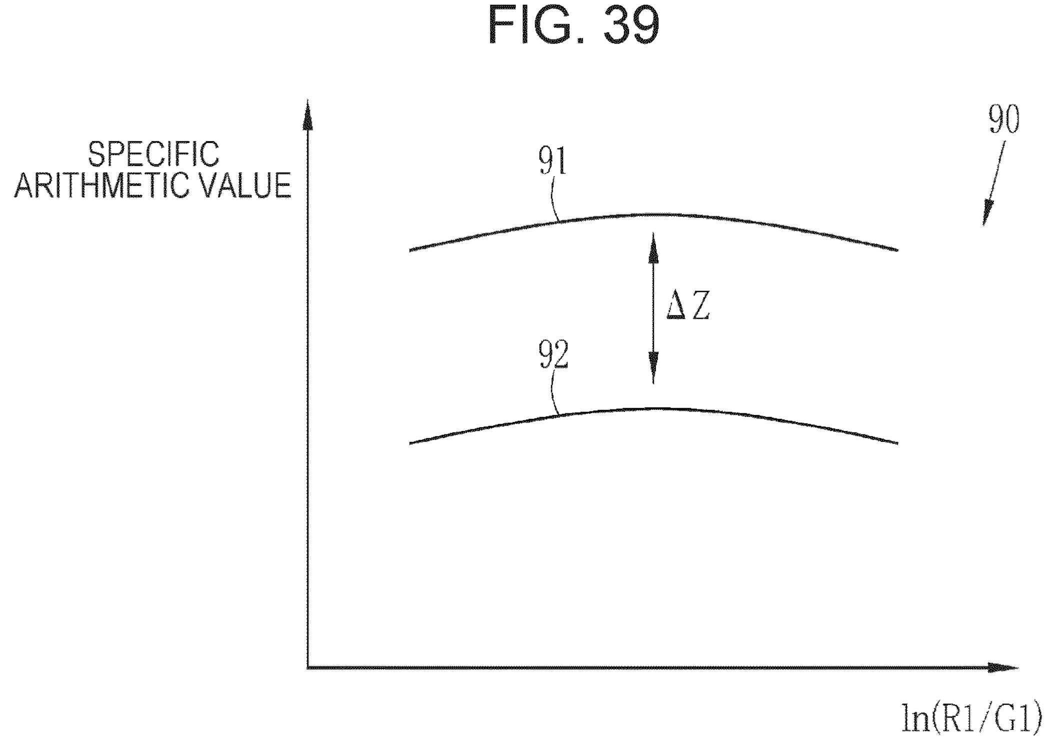
FIG. 39 is an explanatory diagram illustrating a difference value AZ to be used in calculation value correction processing.

Specifically, in the calculation value correction processing, two-dimensional coordinates 90 illustrated in FIG. 39 are used to calculate a correction value to be used for correcting the oxygen saturation calculated on the basis of the oxygen saturation calculation table 73. The vertical axis of the two-dimensional coordinates represents a specific arithmetic value obtained on the basis of the B1 image signal, the G2 image signal, the R2 image signal, and the B3 image signal, and the horizontal axis thereof represents ln(R2/G2). The specific arithmetic value is determined by Expression (A) below.

$$B1/G2\times\cos\phi - B3/G2\times\sin\phi \qquad \text{Expression (A)}$$

The two-dimensional coordinates 90 present a reference line 91 indicating the distribution of predetermined reference baseline information and an actual measurement line 92 indicating the distribution of actual measurement baseline information obtained by actual imaging of the observation target. A difference value AZ between the reference line 91 and the actual measurement line 92 is calculated as a correction value. In the calculation value correction processing, the correction value is added to or subtracted from the oxygen saturation calculated on the basis of the oxygen saturation calculation table 73. The reference baseline information is obtained in the absence of the specific pigment and is determined as information independent of the oxygen saturation. Specifically, a value obtained by adjusting ¢ so that Expression (A) described above is kept constant even when the oxygen saturation changes is set as the reference baseline information.

Figure 40:
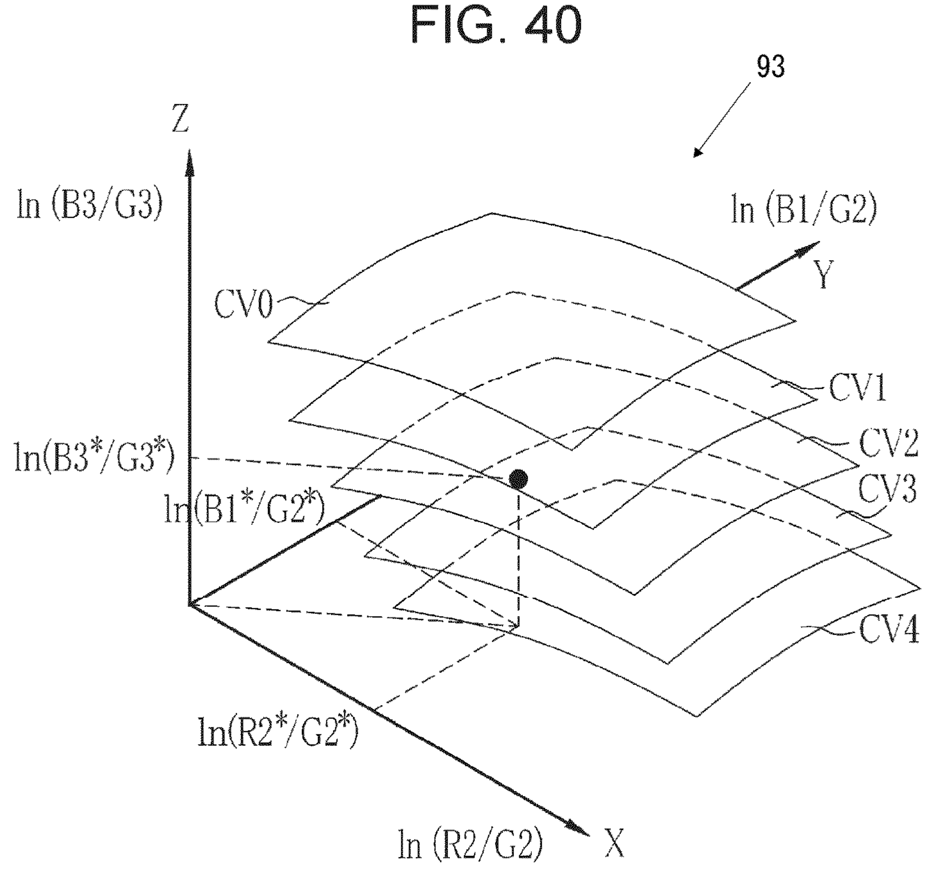
FIG. 40 is an explanatory diagram illustrating a calculation method of specific oxygen saturation calculation processing.

In the correction mode, instead of the correction processing, specific oxygen saturation calculation processing for calculating the oxygen saturation in accordance with the specific pigment concentration on the basis of at least the oxygen-saturation image signal and the specific pigment image signal may be performed. Specifically, three-dimensional coordinates 93 illustrated in FIG. 40 are used for the specific oxygen saturation calculation processing. In the three-dimensional coordinates 93, the X-axis is assigned the signal ratio ln(R2/G2), the Y-axis is assigned the signal ratio ln(B1/G2), and the Z-axis is assigned the signal ratio ln(B3/G3). Curved surfaces CV0 to CV4 represent the states of the oxygen saturations corresponding to the specific pigment concentrations "0" to "4" at the three-dimensional coordinates 93.

In the specific oxygen saturation calculation processing, at the three-dimensional coordinates 93, a value obtained by plotting on the three-dimensional coordinates 93 the signal ratios ln(R1*/G1*), ln(B2*/G1*), and ln(B3*/G3*) calculated on the basis of the B1 image signal, the G2 image signal, the R2 image signal, the B3 image signal, and the G3 image signal is calculated as the oxygen saturation. The calculated oxygen saturation is not affected by the specific pigment concentrations and is thus an accurate value.

Figure 41:
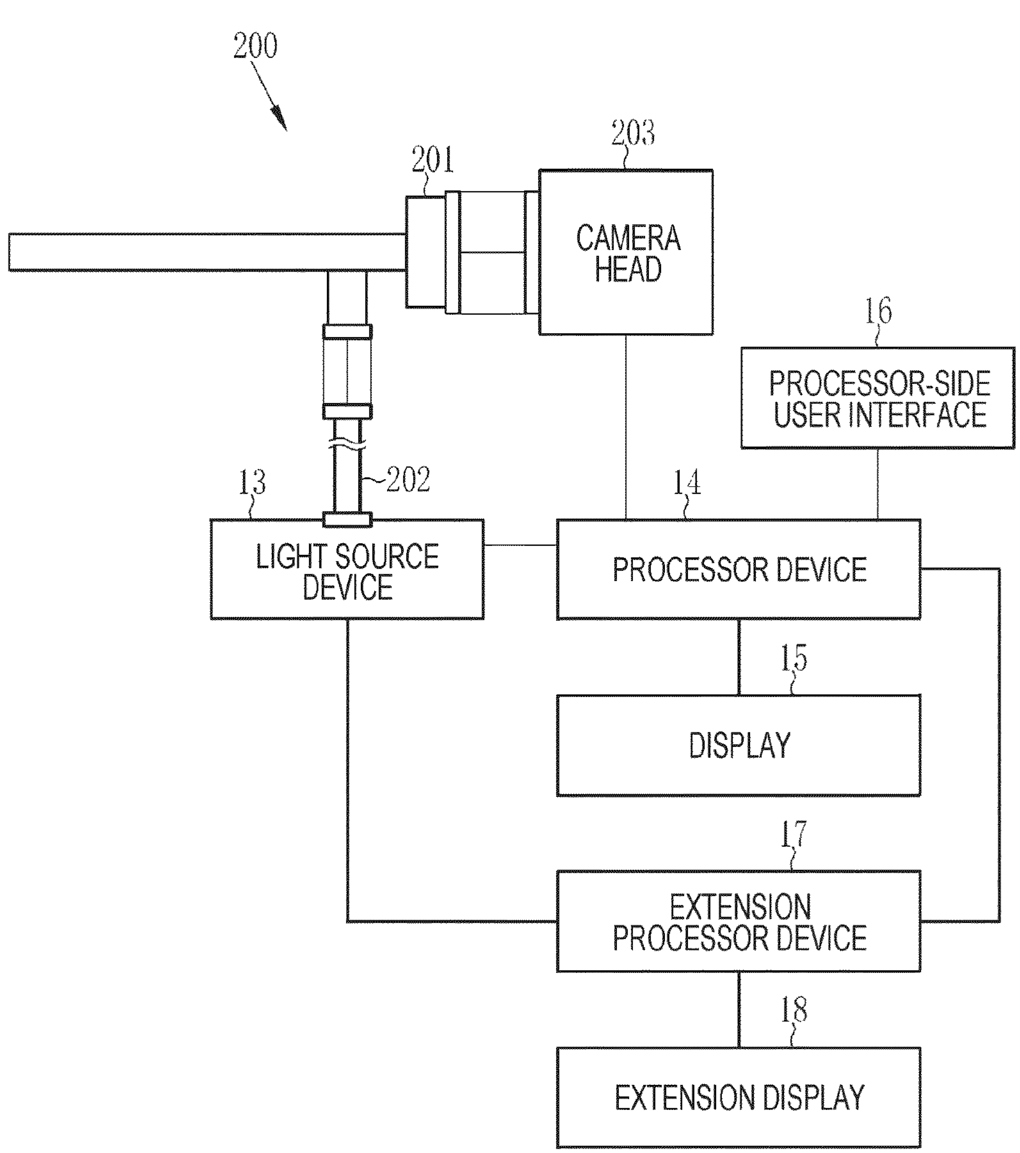
FIG. 41 is a schematic diagram of an endoscope system for laparoscopic endoscopy.

In the first and second embodiments, the endoscope 12, which is a soft endoscope for digestive-tract endoscopy, is used. Alternatively, an endoscope serving as a rigid endoscope for laparoscopic endoscopy may be used. When an endoscope that is a rigid endoscope is used, an endoscope system 200 illustrated in FIG. 41 is used. The endoscope system 200 includes an endoscope 201, a light source device 13, a processor device 14, a display 15, a processor-side user interface 16, an extension processor device 17, and an extension display 18. In the following, portions of the endoscope system 200 common to those of the first and second embodiments will not be described, and only different portions will be described.

The endoscope 201, which is used for laparoscopic surgery or the like, is formed to be rigid and elongated and is inserted into a subject. The endoscope 201 illuminates the observation target with illumination light supplied from the light source device 13 via a light guide 202. Further, the endoscope 201 receives reflected light from the observation target being illuminated with the illumination light. A camera head 203 is attached to the endoscope 201 and is configured to perform imaging of the observation target on the basis of reflected light guided from the endoscope 201. An image signal obtained by the camera head 203 through imaging is transmitted to the processor device 14.

In the normal mode, the light source device 13 supplies white light including the violet light V, the second blue light BS, the green light G, and the red light R to the endoscope 201. In the oxygen saturation mode and the correction mode, as illustrated in FIG. 42, the light source device 13 supplies mixed light including the first blue light BL, the second blue light BS, the green light G, and the red light R to the endoscope 12.

Figures 42, 43:
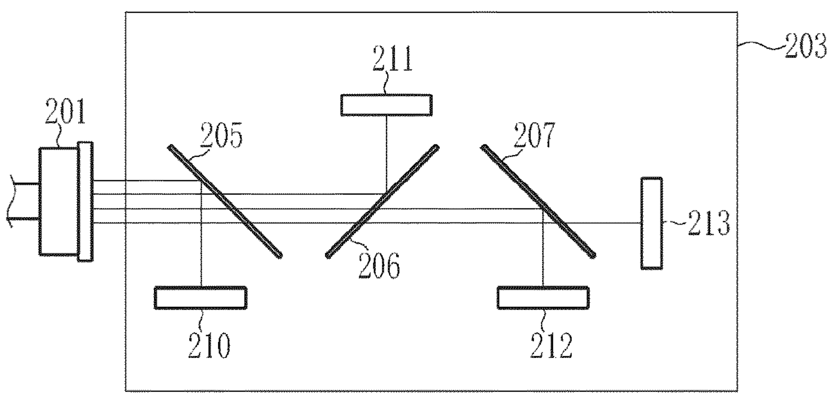
FIG. 42 is a graph illustrating emission spectra of mixed light.
FIG. 43 is an explanatory diagram illustrating functions of a camera head having four monochrome imaging sensors.
Figure 44:
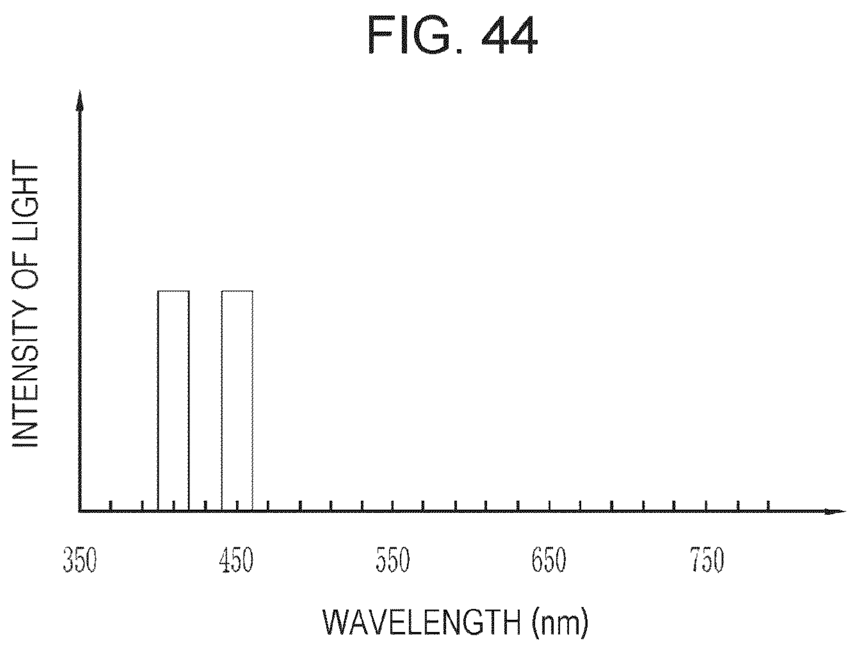
FIG. 44 is a graph illustrating emission spectra of violet light and second blue light.

As illustrated in FIG. 43, the camera head 203 includes dichroic mirrors 205, 206, and 207, and monochrome imaging sensors 210, 211, 212, and 213. The dichroic mirror 205 reflects, of the reflected light of the mixed light from the endoscope 201, the violet light V and the second blue light BS and transmits the first blue light BL, the green light G, and the red light R. As illustrated in FIG. 44, the violet light V or the second blue light BS reflected by the dichroic mirror 205 is incident on the imaging sensor 210. The imaging sensor 210 outputs a Bc image signal in response to the incidence of the violet light V and the second blue light BS in the normal mode, and outputs a B2 image signal in response to the incidence of the second blue light BS in the oxygen saturation mode or the correction mode.

Figure 45:
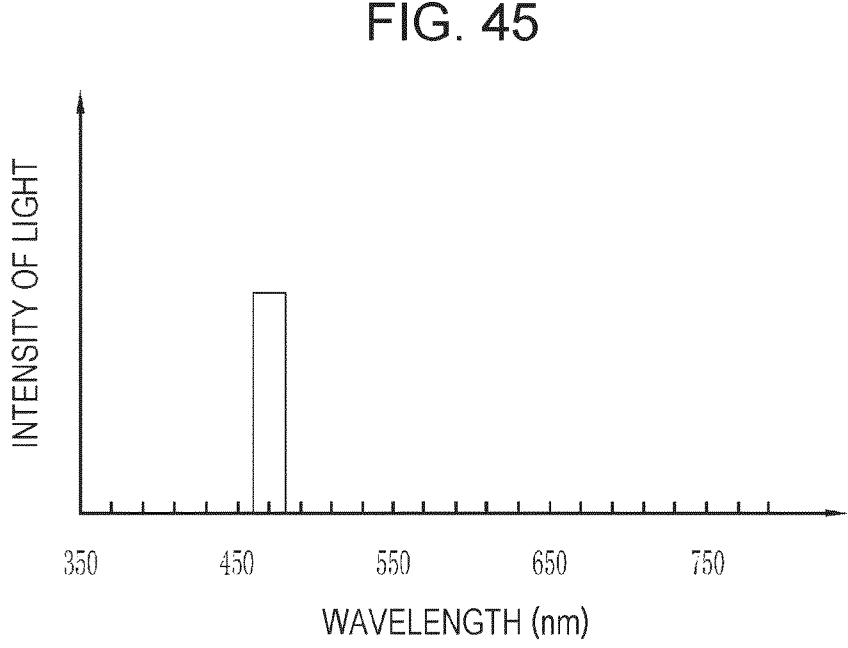
FIG. 45 is a graph illustrating an emission spectrum of first blue light.

The dichroic mirror 206 reflects, of the light transmitted through the dichroic mirror 205, the first blue light BL and transmits the green light G and the red light R. As illustrated in FIG. 45, the first blue light BL reflected by the dichroic mirror 206 is incident on the imaging sensor 211. The imaging sensor 211 stops outputting an image signal in the normal mode, and outputs a B1 image signal in response to the incidence of the first blue light BL in the oxygen saturation mode or the correction mode.

Figure 46:
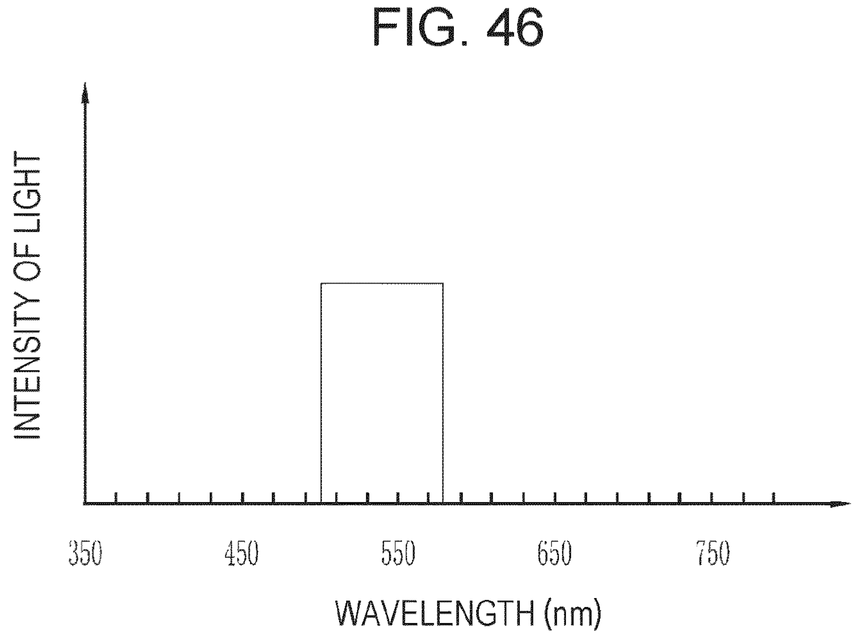
FIG. 46 is a graph illustrating an emission spectrum of green light.

The dichroic mirror 207 reflects, of the light transmitted through the dichroic mirror 206, the green light G and transmits the red light R. As illustrated in FIG. 46, the green light G reflected by the dichroic mirror 207 is incident on the imaging sensor 212. The imaging sensor 212 outputs a Gc image signal in response to the incidence of the green light G in the normal mode, and outputs a G2 image signal in response to the incidence of the green light G in the oxygen saturation mode or the correction mode.

Figure 47:
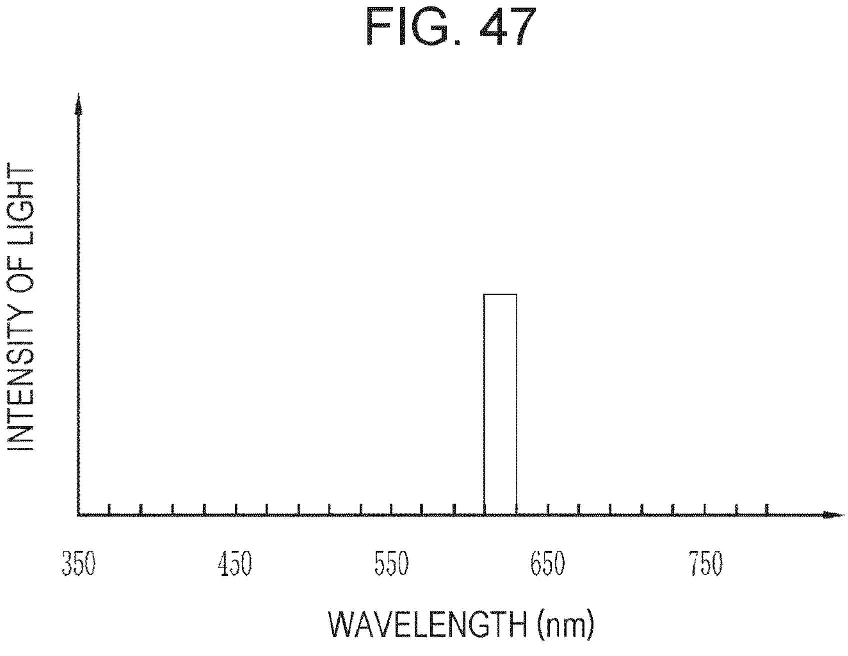
FIG. 47 is a graph illustrating an emission spectrum of red light.

As illustrated in FIG. 47, the red light R transmitted through the dichroic mirror 207 is incident on the imaging sensor 213. The imaging sensor 213 outputs an Rc image signal in response to the incidence of the red light R in the normal mode, and outputs an R2 image signal in response to the incidence of the red light R in the oxygen saturation mode or the correction mode.

In the first and second embodiments described above, the B1 image signal, the G2 image signal, and the R2 image signal including the image information of the wavelength range B1 in which the reflection spectrum changes in accordance with a change in the oxygen saturation of blood hemoglobin are used to calculate the oxygen saturation. Alternatively, any other image signal may be used instead of the B1 image signal. For example, as illustrated in FIG. 48, instead of the B1 image signal, an Rk image signal including image information of a wavelength range Rx in which the reflection spectrum changes in accordance with a change in the oxygen saturation of blood hemoglobin may be used. The wavelength range Rx is preferably 680 nm±10 nm. As illustrated in FIG. 49, the Rk image signal has "medium to low" oxygen saturation dependence, but has "low" blood concentration dependence and "low" yellow pigment dependence. Accordingly, even in a situation where the yellow pigment is present in the observation target, the oxygen saturation can be accurately calculated using only three image signals, namely, the G2 image signals, the R2 image signal, and the Rk image signal.

Figure 50:
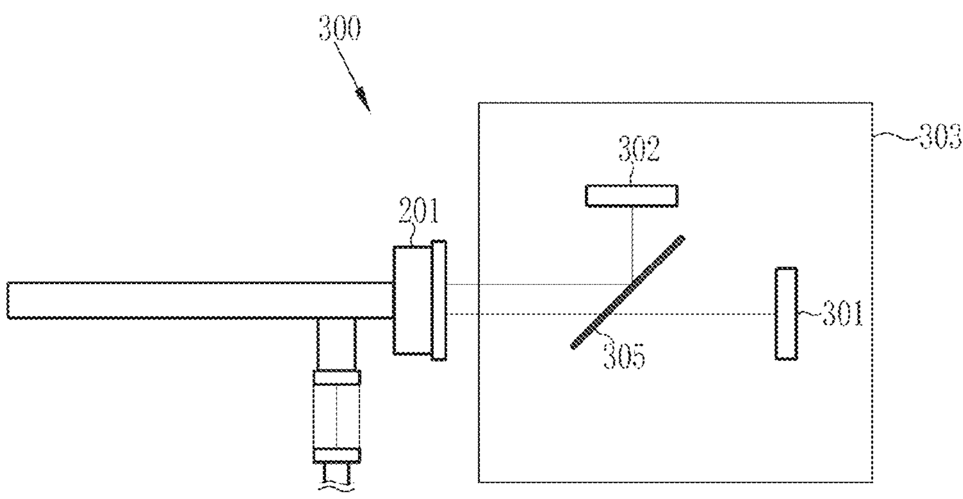
FIG. 50 is an explanatory diagram of a two-sensor laparoscopic endoscope having a camera head having a color imaging sensor and a monochrome imaging sensor.

When the endoscope (see FIG. 41), which is a rigid endoscope for laparoscopic endoscopy, is used, unlike the endoscope 201 (see FIG. 43) that performs imaging of the observation target by using the four monochrome imaging sensors 210 to 213, the endoscope may be used to perform imaging of the observation target by using any other imaging method. As illustrated in FIG. 50, an endoscope 300 is a two-sensor endoscope for the abdominal cavity having one color imaging sensor 301 and one monochrome imaging sensor 302. A camera head 303 of the endoscope 300 is provided with, in addition to the color imaging sensor 301 and the monochrome imaging sensor 302, a dichroic mirror 305 that transmits part of the light incident on the camera head 303 and reflects the remaining part of the light.

Figure 51A:
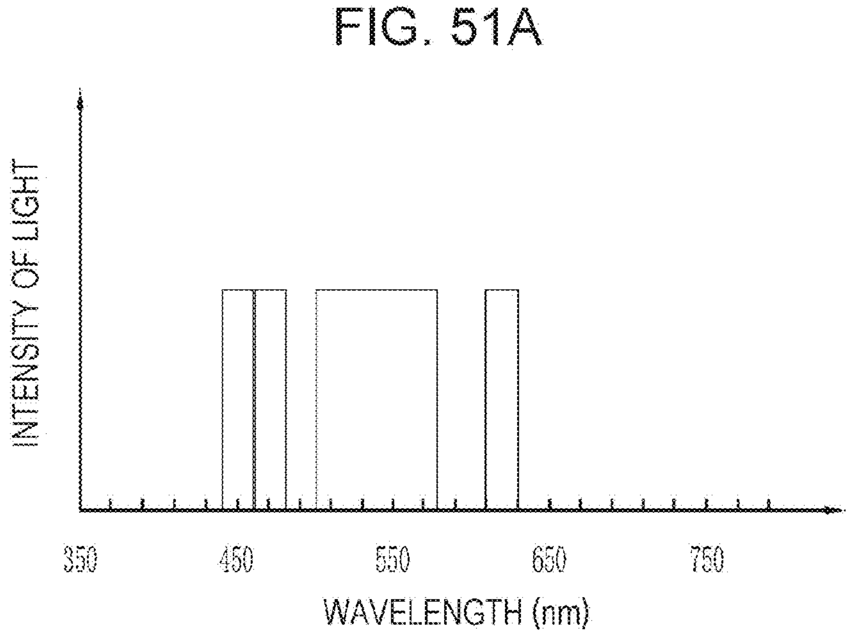
Figure 51B:
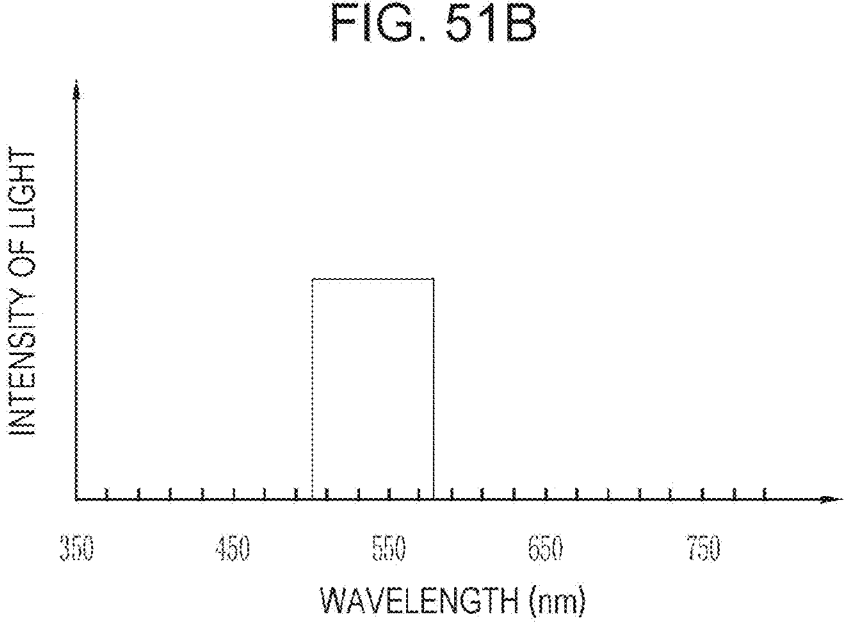

In the light emission control of the light source device 13 when the endoscope 300 is used, as illustrated in FIGS. 51A and 51B, a white frame (see FIG. 51A) in which the first blue light BL, the second blue light BS, the green light G, and the red light R are simultaneously emitted and a green frame (see FIG. 51B) in which only the green light G is emitted are switched and emitted in accordance with a specific light emission pattern.

Figures 52A, 52B, 52C, 52D:
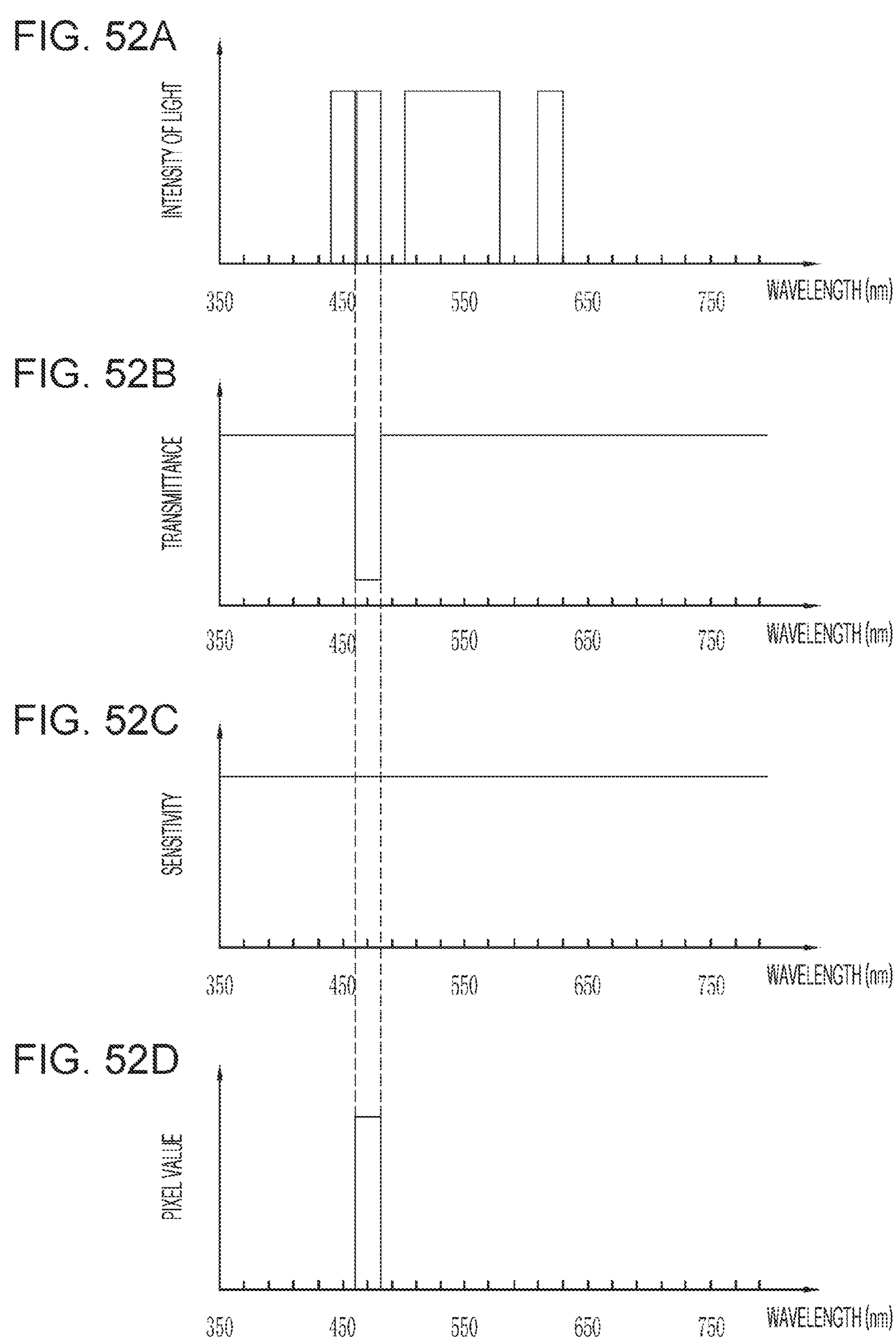
FIG. 52A is a graph illustrating light emission patterns during the white frame.
FIG. 52B is a graph illustrating transmittance of a dichroic mirror.
FIG. 52C is a graph illustrating sensitivity of the monochrome imaging sensor.
FIG. 52D is a graph illustrating a pixel value of an image signal output from the monochrome imaging sensor during the white frame.

As illustrated in FIGS. 52A to 52D, when the first blue light BL, the second blue light BS, the green light G, and the red light R are simultaneously emitted in the white frame (see FIG. 52A), of the light incident on the camera head 303, the first blue light BL is reflected by the dichroic mirror 305 (see FIG. 52B), and the other light, namely, the second blue light BS, the green light G, and the red light R, is transmitted through the dichroic mirror 305 (see FIG. 52B). The first blue light BL reflected by the dichroic mirror 305 is incident on the monochrome imaging sensor 302 (see FIG. 52C). The monochrome imaging sensor 302 outputs a B1 image signal having a pixel value corresponding to the incident first blue light BL (see FIG. 52D).

Figures 53A, 53B, 53C, 53D:
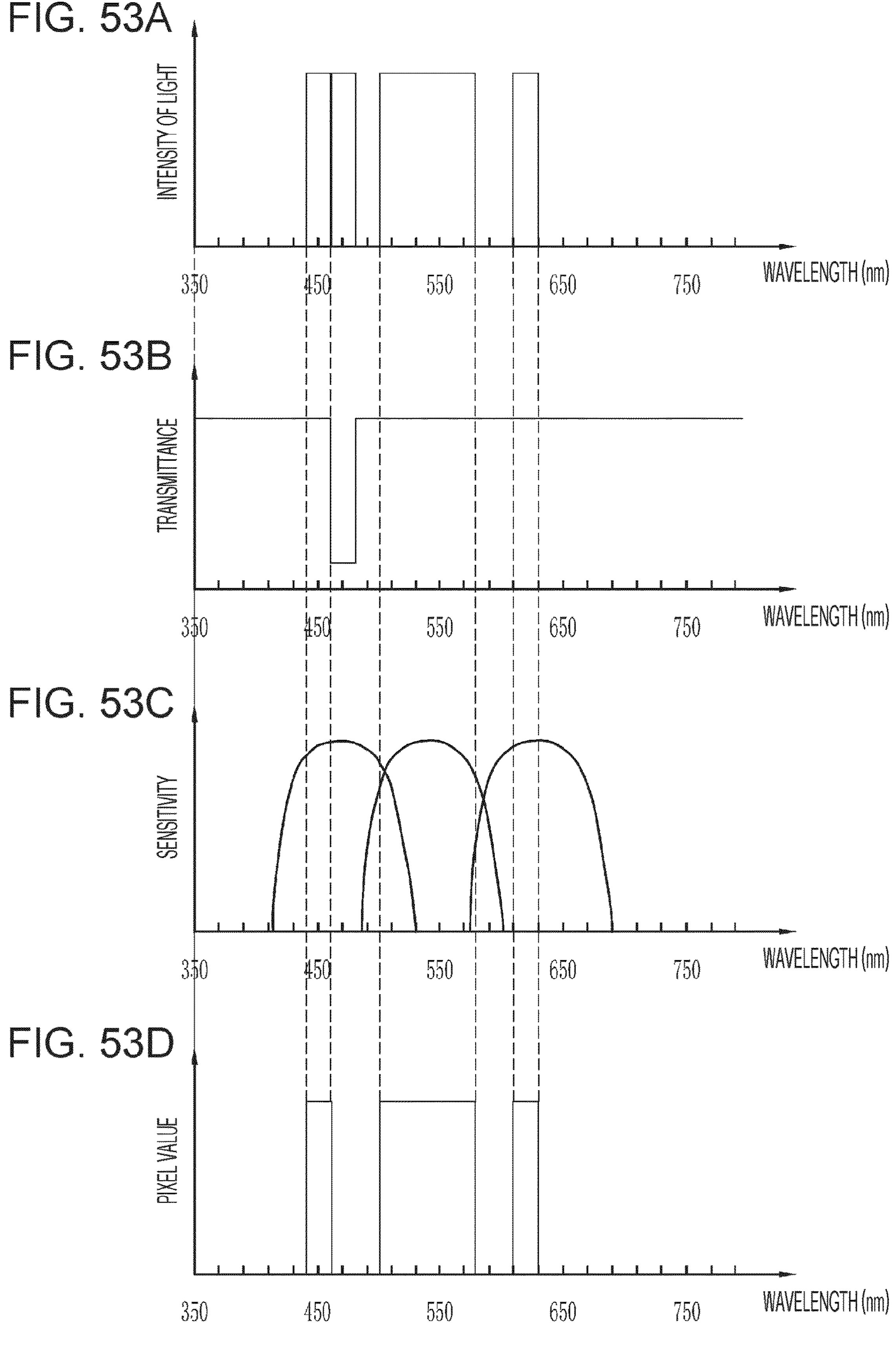
FIG. 53A is a graph illustrating the light emission patterns during the white frame.
FIG. 53B is a graph illustrating the transmittance of the dichroic mirror.
FIG. 53C is a graph illustrating sensitivity of the color imaging sensor.
FIG. 53D is a graph illustrating a pixel value of an image signal output from the color imaging sensor during the white frame.
Figures 54A, 54B, 54C, 54D, 54E:
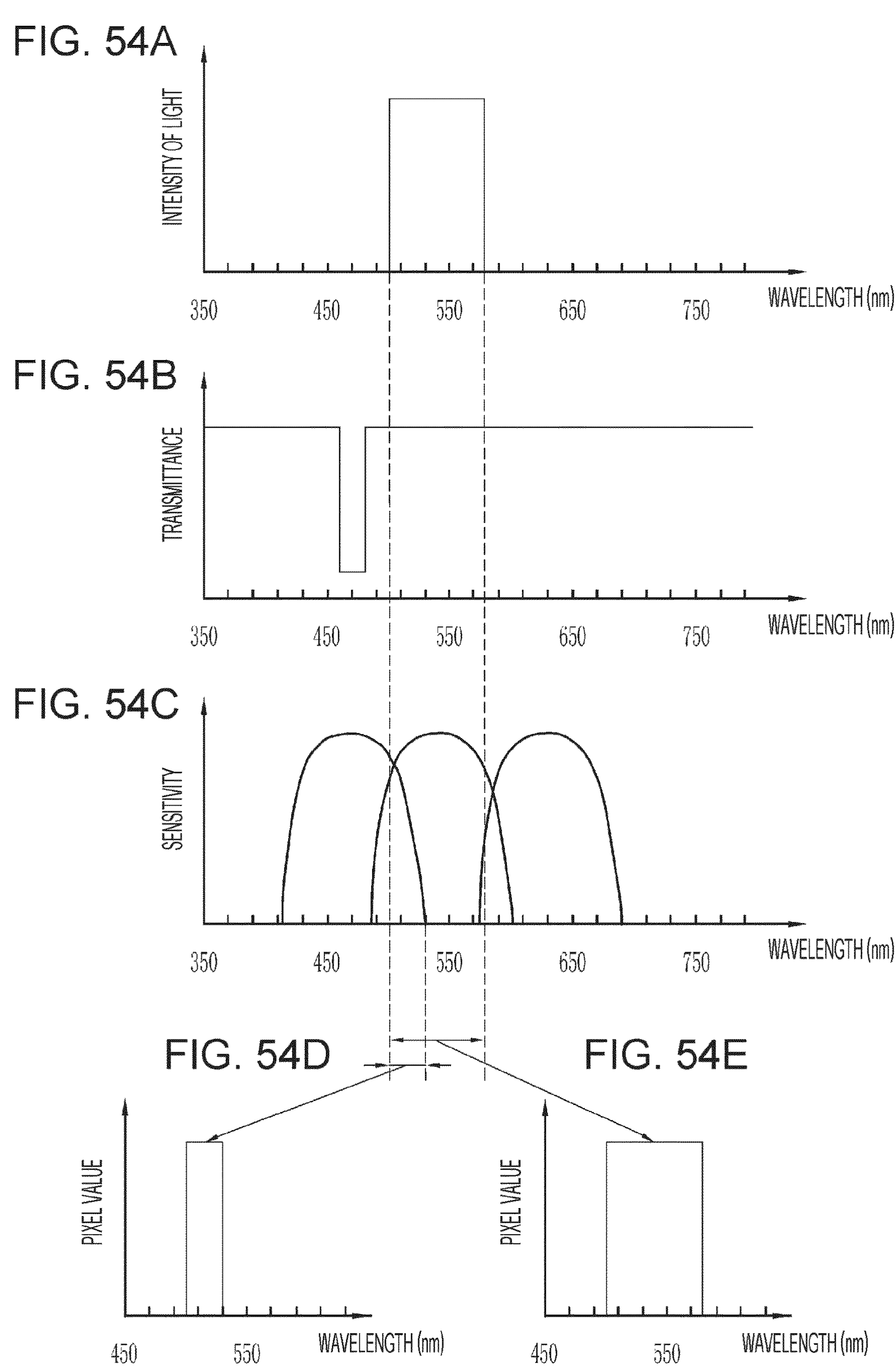
FIG. 54A is a graph illustrating light emission patterns during a green frame.
FIG. 54B is a graph illustrating the transmittance of the dichroic mirror.
FIG. 54C is a graph illustrating sensitivity of the color imaging sensor.
FIG. 54D is a graph illustrating a pixel value of an image signal output from B pixels of the color imaging sensor during the green frame.
FIG. 54E is a graph illustrating a pixel value of an image signal output from G pixels of the color imaging sensor during the green frame.

Further, as illustrated in FIGS. 53A to 53D, in the white frame, the second blue light BS, the green light G, and the red light R transmitted through the dichroic mirror 305 are incident on the color imaging sensor 301 (see FIG. 53C). In the color imaging sensor 301, the B pixels output a B2 image signal having a pixel value corresponding to the light transmitted through the B color filter BF out of the second blue light BS. The G pixels output a G2 image signal having a pixel value corresponding to the light transmitted through the G color filter GF out of the green light G. The R pixels output an R2 image signal having a pixel value corresponding to the light transmitted through the R color filter RF out of the red light R.

In contrast, as illustrated in FIGS. 54A to 54E, when only the green light G is emitted in the green frame (see FIG. 54A), the green light G incident on the camera head 303 is transmitted through the dichroic mirror 305. The green light G transmitted through the dichroic mirror 305 is incident on the color imaging sensor 301. In the color imaging sensor 301, the B pixels output a B3 image signal having a pixel value corresponding to light transmitted through the B color filter BF out of the green light G. The G pixels output a G3 image signal having a pixel value corresponding to light transmitted through the G color filter GF out of the green light G. In the green frame, the image signals output from the monochrome imaging sensor 302 and the image signals output from the R pixels of the color imaging sensor 301 are not used in the subsequent processing steps.

As illustrated in FIG. 55, as described above, in a white frame, a B1 image signal is output from the monochrome imaging sensor 302, and a B2 image signal, a G2 image signal, and an R2 image signal are output from the color imaging sensor 301. The B1, B2, G2, and R2 image signals are used in the subsequent processing steps. In a green frame, by contrast, a B3 image signal and a G3 image signal are output from the color imaging sensor 301 and are used in the subsequent processing steps.

As illustrated in FIG. 56, the image signals output from the camera head 303 are sent to the processor device 14, and data on which various types of processing are performed by the processor device 14 is sent to the extension processor device 17. When the endoscope 300 is used, the processing load on the processor device 14 is taken into account, and the processes are performed in the oxygen saturation mode and the correction mode such that the processor device 14 performs low-load processing and then the extension processor device 17 performs high-load processing. Of the processes to be performed in the oxygen saturation mode and the correction mode, the processing to be performed by the processor device 14 is mainly performed by an FPGA (Field-Programmable Gate Array) and is thus referred to as FPGA processing. On the other hand, the processing to be performed by the extension processor device 17 is referred to as PC processing since the extension processor device 17 is implemented as a PC (Personal Computer).

When the endoscope 300 is provided with an FPGA (not illustrated), the FPGA of the endoscope 300 may perform the FPGA processing. While the following describes the FPGA processing and the PC processing in the correction mode, the processes are preferably divided into the FPGA processing and the PC processing also in the oxygen saturation mode to share the processing load.

In a case where the endoscope 300 is used and light emission control is performed for a white frame W and a green frame Gr in accordance with a specific light emission pattern, as illustrated in FIG. 57, the specific light emission pattern is such that light is emitted in two white frames W and then two blank frames BN are used in which no light is emitted from the light source device 13. Thereafter, light is emitted in two green frames Gr, and then two or more several (e.g., seven) blank frames are used. Thereafter, light is emitted again in two white frames W. The specific light emission pattern described above is repeatedly performed. As in the specific light emission pattern described above, light is emitted in the white frame W and the green frame Gr at least in the correction mode. In the oxygen saturation mode, light may be emitted in only the white frame W, but no light is emitted in the green frame Gr.

In the following, of the first two white frames, the first white frame is referred to as a white frame W1, and the subsequent white frame is referred to as a white frame W2 to distinguish the light emission frames in which light is emitted in accordance with a specific light emission pattern. Of the two green frames, the first green frame is referred to as a green frame Gr1, and the subsequent green frame is referred to as a green frame Gr2. Of the last two white frames, the first white frame is referred to as a white frame W3, and the subsequent white frame is referred to as a white frame W4.

The image signals for the correction mode (the B1 image signal, the B2 image signal, the G2 image signal, the R2 image signal, the B3 image signal, and the G3 image signal) obtained in the white frame W1 are referred to as an image signal set W1. Likewise, the image signals for the correction mode obtained in the white frame W2 are referred to as an image signal set W2. The image signals for the correction mode obtained in the green frame Gr1 are referred to as an image signal set Gr1. The image signals for the correction mode obtained in the green frame Gr2 are referred to as an image signal set Gr2. The image signals for the correction mode obtained in the white frame W3 are referred to as an image signal set W3. The image signals for the correction mode obtained in the white frame W4 are referred to as an image signal set W4. The image signals for the oxygen saturation mode are image signals included in a white frame (the B1 image signal, the B2 image signal, the G2 image signal, and the R2 image signal).

The number of blank frames between the white frame W and the green frame Gr is desirably about two because it is only required to eliminate the light other than the green light G, whereas the number of blank frames between the green frame Gr and the white frame W is two or more because it is necessary to take time to stabilize the light emission state because of the start of turning on the light other than the green light G.

Figure 58:
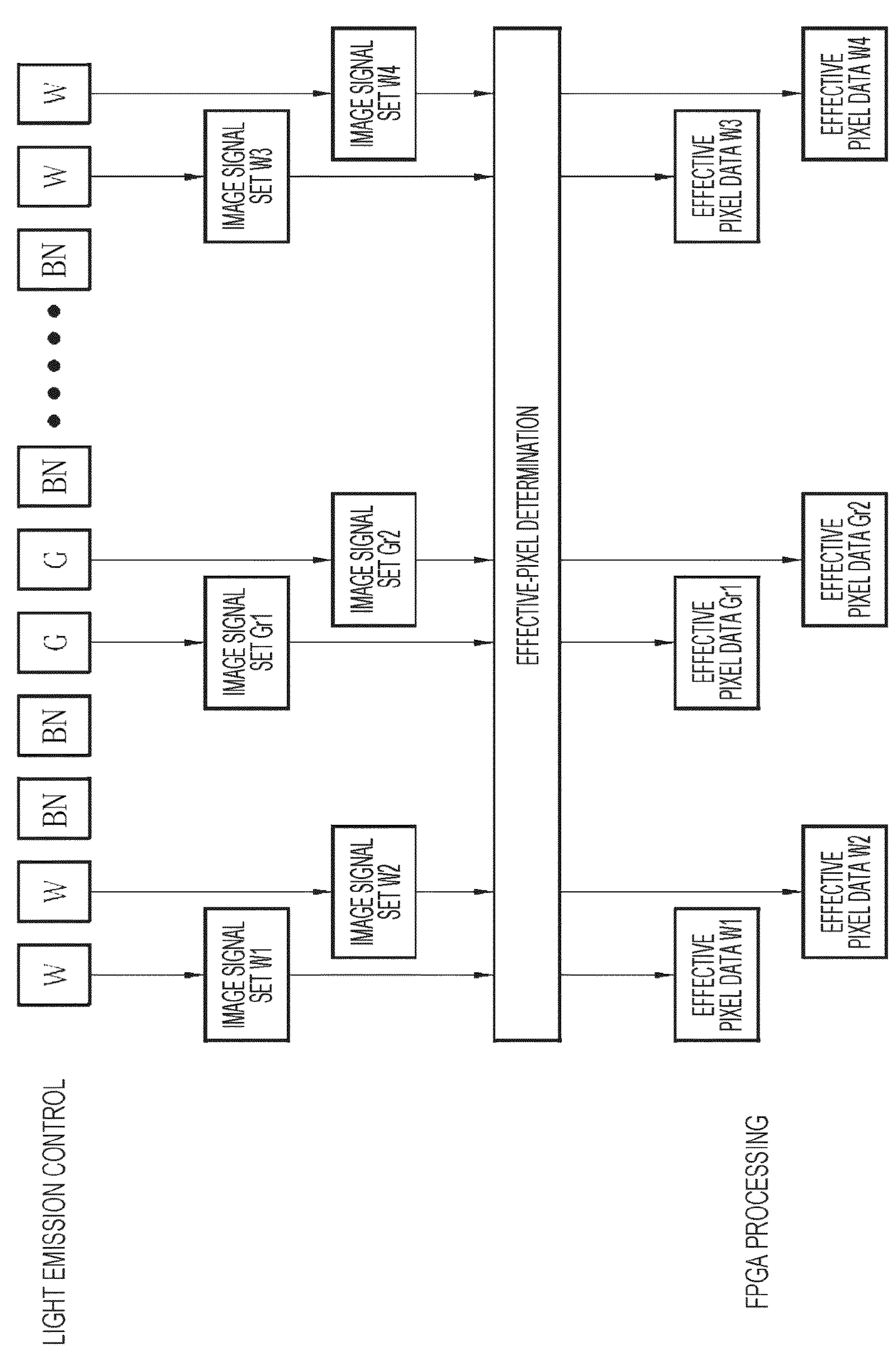
FIG. 58 is an explanatory diagram illustrating effective pixel data subjected to effective-pixel determination.
Figure 59:
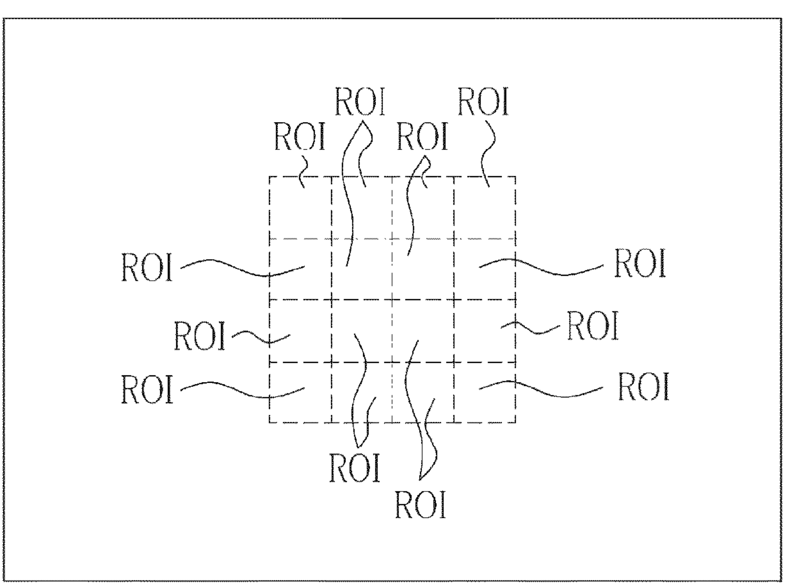
FIG. 59 is an explanatory diagram illustrating ROIs.

In the FPGA processing, as illustrated in FIG. 58, the pixels of all the image signals included in the image signal sets W1, W2, Gr1, Gr2, W3, and W4 are subjected to effective-pixel determination to determine whether the processing can be accurately performed in the oxygen saturation mode or the correction mode. As illustrated in FIG. 59, the effective-pixel determination is performed on the basis of pixel values in 16 regions of interest (ROIs) provided in a center portion of an image. Specifically, for each of the pixels in the ROIs, if the pixel value falls within a range between an upper limit threshold value and a lower limit threshold value, the pixel is determined to be an effective pixel. The effective-pixel determination is performed on the pixels of all the image signals included in the image signal sets. The upper limit threshold value or the lower limit threshold value is set in advance in accordance with the sensitivity of the B pixels, the G pixels, and the R pixels of the color imaging sensor 301 or the sensitivity of the monochrome imaging sensor 302.

On the basis of the effective-pixel determination described above, the number of effective pixels, the total pixel value of the effective pixels, and the sum of squares of the pixel values of the effective pixels are calculated for each ROI. The number of effective pixels, the total pixel value of the effective pixels, and the sum of squares of the pixel values of the effective pixels for each ROI are output to the extension processor device 17 as each of pieces of effective pixel data W1, W2, Gr1, Gr2, W3, and W4. The FPGA processing is arithmetic processing using image signals of the same frame, such as effective-pixel determination, and has a lighter processing load than arithmetic processing using inter-frame image signals of different light emission frames, such as PC processing described below. The pieces of effective pixel data W1, W2, Gr1, Gr2, W3, and W4 correspond to pieces of data obtained by performing effective-pixel determination on all the image signals included in the image signal sets W1, W2, Gr1, Gr2, W3, and W4, respectively.

In the PC processing, intra-frame PC processing and inter-frame PC processing are performed on image signals of the same frame and image signals of different frames, respectively, among the pieces of effective pixel data W1, W2, Gr1, Gr2, W3, and W4. In the intra-frame PC processing, the average value of pixel values, the standard deviation value of the pixel values, and the effective pixel rate in the ROIs are calculated for all the image signals included in each piece of effective pixel data. The average value of the pixel values and the like in the ROIs, which are obtained by the intra-frame PC processing, are used in an arithmetic operation for obtaining a specific result in the oxygen saturation mode or the correction mode.

Figure 60:
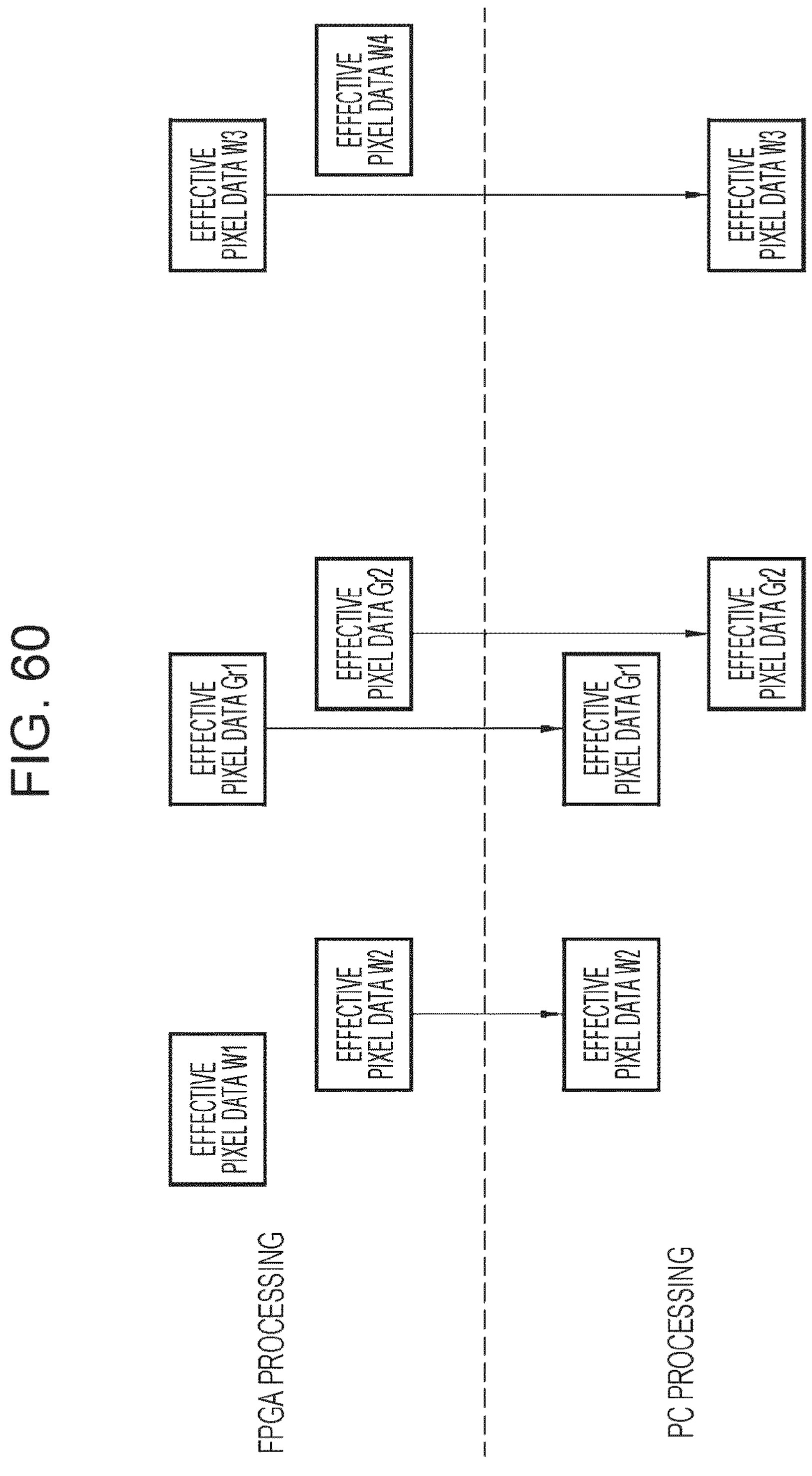
FIG. 60 is an explanatory diagram illustrating effective pixel data used in the PC processing.

In the inter-frame PC processing, as illustrated in FIG. 60, among the pieces of effective pixel data W1, W2, Gr1, Gr2, W3, and W4 obtained in the FPGA processing, effective pixel data having a short time interval between the white frame and the green frame is used, and the other effective pixel data is not used in the inter-frame PC processing. Specifically, a pair of the effective pixel data W2 and the effective pixel data Gr1 and a pair of the effective pixel data Gr2 and the effective pixel data W3 are used in the inter-frame PC processing. The other pieces of effective pixel data W1 and W4 are not used in the inter-frame PC processing. The use of a pair of image signals having a short time interval provides accurate inter-frame PC processing without misalignment of pixels.

Figure 61:
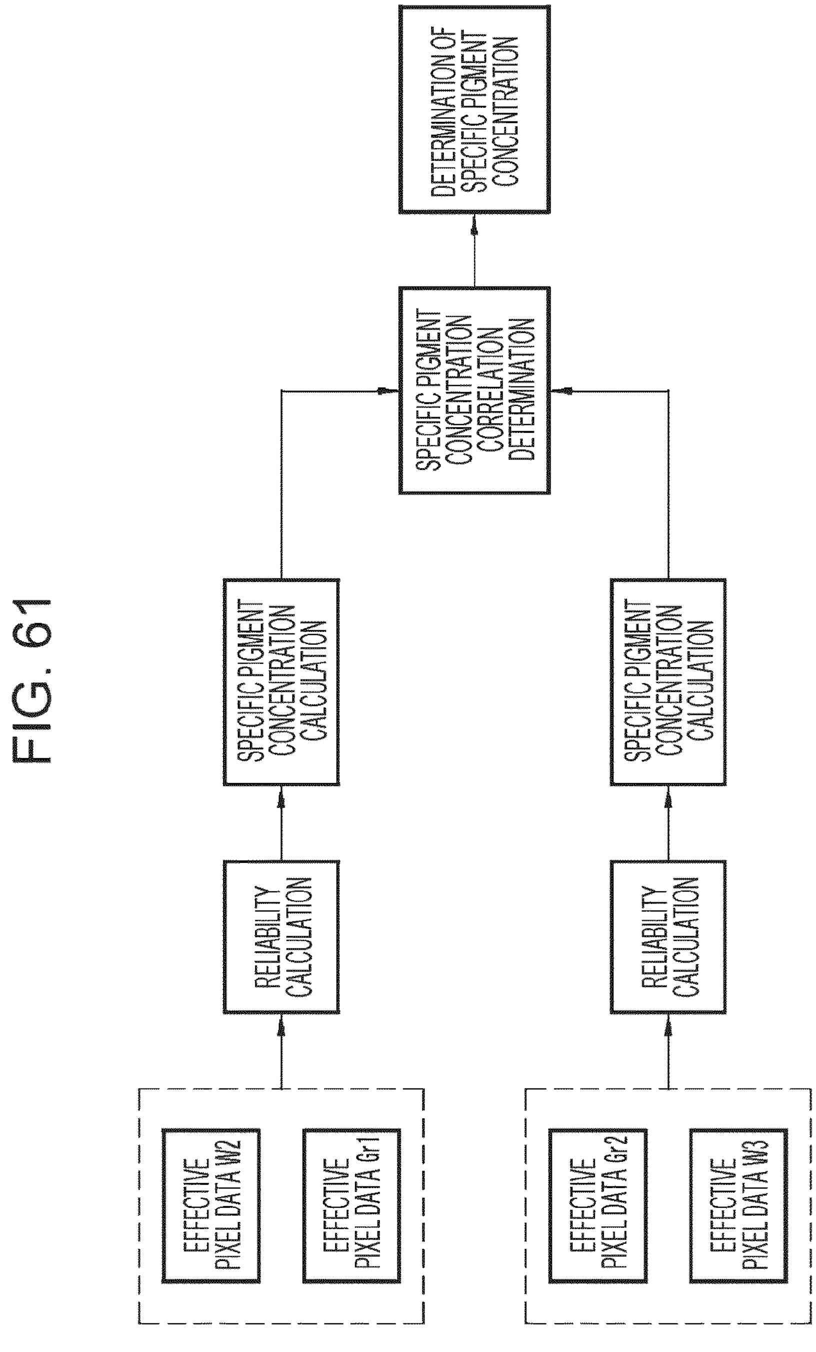
FIG. 61 is an explanatory diagram illustrating reliability calculation, specific pigment concentration calculation, and specific pigment concentration correlation determination.

As illustrated in FIG. 61, the inter-frame PC processing using the pair of the effective pixel data W2 and the effective pixel data Gr1 involves reliability calculation and specific pigment concentration calculation, and the inter-frame PC processing using the pair of the effective pixel data Gr2 and the effective pixel data W3 also involves reliability calculation and specific pigment concentration calculation. Then, specific pigment concentration correlation determination is performed on the basis of the calculated specific pigment concentrations.

In the calculation of the reliability, the reliability is calculated for each of the 16 ROIs. The method for calculating the reliability is similar to the calculation method performed by the reliability calculation unit 66 described above. For example, the reliability for a brightness value of a G2 image signal outside the certain range Rx is preferably set to be lower than the reliability for a brightness value of a G2 image signal within the certain range Rx (see FIG. 28). In the case of the pair of the effective pixel data W2 and the effective pixel data Gr1, a total of 32 reliabilities are calculated by reliability calculation of a G2 image signal included in each piece of effective pixel data for each ROI. Likewise, in the pair of the effective pixel data Gr2 and the effective pixel data W3, a total of 32 reliabilities are calculated. When the reliability is calculated, for example, if a ROI having low reliability is present or if the average reliability value of the ROIs is less than a predetermined value, error determination is performed for the reliability. The result of the error determination for the reliability is displayed on the extension display 18 or the like to provide a notification to the user.

In the specific pigment concentration calculation, a specific pigment concentration is calculated for each of the 16 ROIs. The method for calculating the specific pigment concentration is similar to the calculation method performed by the specific pigment concentration calculation unit 62 described above. For example, the specific pigment concentration calculation table 62*a* is referred to by using the B1 image signal, the G2 image signal, the R2 image signal, the B3 image signal, and the G3 image signal included in the effective pixel data W2 and the effective pixel data Gr1, and a specific pigment concentration corresponding to the signal ratios ln(B1/G2), ln(G2/R2), and ln(B3/G3) is calculated. As a result, a total of 16 specific pigment concentrations PG1 are calculated for the respective ROIs. Also in the case of the pair of the effective pixel data Gr2 and the effective pixel data W3, a total of 16 specific pigment concentrations PG2 are calculated for the respective ROIs in a similar manner.

When the specific pigment concentrations PG1 and the specific pigment concentrations PG2 are calculated, correlation values between the specific pigment concentrations PG1 and the specific pigment concentrations PG2 are calculated for the respective ROIs. The correlation values are preferably calculated for the respective ROIs at the same position. If a certain number or more of ROIs having correlation values lower than a predetermined value are present, it is determined that a motion has occurred between the frames, and error determination for the motion is performed. The result of the error determination for the motion is notified to the user by, for example, being displayed on the extension display 18.

If no error is present in the error determination for the motion, one specific pigment concentration is calculated from among the total of 32 specific pigment concentrations PG1 and specific pigment concentrations PG2 by using a specific estimation method (e.g., a robust estimation method). The calculated specific pigment concentration is used in the correction processing for the correction mode. The correction processing for the correction mode is similar to that described above, such as table correction processing.

In the embodiments described above, the hardware structures of processing units that perform various types of processing, such as the oxygen saturation image generation unit 61, the specific pigment concentration calculation unit 62, the table correction unit 63, the mode switching unit 64, the display style control unit 65, the reliability calculation unit 66, the first correction determination unit 67, the second correction determination unit 68, the determination notification unit 69, the base image generation unit 70, the arithmetic value calculation unit 71, the oxygen saturation calculation unit 72, and the color tone adjustment unit 74, are various processors described below. The various processors include a CPU (Central Processing Unit), which is a general-purpose processor executing software (program) to function as various processing units, a GPU (Graphical Processing Unit), a programmable logic device (PLD) such as an FPGA (Field Programmable Gate Array), which is a processor whose circuit configuration is changeable after manufacturing, a dedicated electric circuit, which is a processor having a circuit configuration specifically designed to execute various types of processing, and so on.

A single processing unit may be configured as one of these various processors or as a combination of two or more processors of the same type or different types (such as a plurality of FPGAs, a combination of a CPU and an FPGA, or a combination of a CPU and a GPU, for example). Alternatively, a plurality of processing units may be configured as a single processor. Examples of configuring a plurality of processing units as a single processor include, first, a form in which, as typified by a computer such as a client or a server, the single processor is configured as a combination of one or more CPUs and software and the processor functions as the plurality of processing units. The examples include, second, a form in which, as typified by a system on chip (SoC) or the like, a processor is used in which the functions of the entire system including the plurality of processing units are implemented as one IC (Integrated Circuit) chip. As described above, the various processing units are configured by using one or more of the various processors described above as a hardware structure.

More specifically, the hardware structure of these various processors is an electric circuit (circuitry) in which circuit elements such as semiconductor elements are combined. The hardware structure of a storage unit (memory) is a storage device such as an HDD (hard disc drive) or an SSD (solid state drive).

[Appendix 1]

An endoscope system including a processor configured to:

switch between an oxygen saturation mode for calculating an oxygen saturation of blood hemoglobin and a correction mode for displaying a correction image on a display and displaying a specific region on the display, the correction mode being a mode in which correction processing related to calculation of the oxygen saturation is performed based on a specific pigment concentration of a specific pigment other than the blood hemoglobin included in the specific region, the specific pigment concentration being calculated based on a specific pigment image signal including image information of a wavelength range having sensitivity to the specific pigment; and in the correction mode, perform at least one of changing a display style of the correction image or changing a display style of the specific region in accordance with reliability related to the calculation of the oxygen saturation.

[Appendix 2]

The endoscope system according to Appendix 1, wherein the processor is configured to generate a correction image with a reduced luminance of a dark portion.

[Appendix 3]

The endoscope system according to Appendix 1 or 2, wherein the processor is configured to generate a correction image with saturation enhanced.

[Appendix 4]

The endoscope system according to Appendix 1, wherein the processor is configured to change the display style of the correction image so that a difference between a low-reliability region in which the reliability is low and a high-reliability region in which the reliability is high is emphasized.

[Appendix 5]

The endoscope system according to Appendix 4, wherein the processor is configured to set a saturation of the low-reliability region to be higher than a saturation of the high-reliability region.

[Appendix 6]

The endoscope system according to Appendix 4 or 5, wherein the processor is configured to reduce a luminance of a dark portion in the low-reliability region.

[Appendix 7]

The endoscope system according to any one of Appendices 4 to 6, wherein the processor is configured to perform at least one of superimposing a region highlighting line on the low-reliability region or displaying the low-reliability region in monochrome.

[Appendix 8]

The endoscope system according to any one of Appendices 1 to 7, wherein the processor is configured to:

determine whether it is possible to appropriately perform the correction processing, based on the reliability in the specific region; and make the display style of the specific region different between when it is possible to appropriately perform the correction processing and when it is not possible to appropriately perform the correction processing.

[Appendix 9]

The endoscope system according to any one of Appendices 1 to 7, wherein the processor is configured to:

make a determination as to whether it is possible to appropriately perform the correction processing, based on the reliability in the specific region at a timing at which a correction operation for performing the correction processing is performed; and provide a notification related to the determination.

[Appendix 10]

The endoscope system according to Appendix 9, wherein the processor is configured to provide a notification of operational guidance for performing the correction processing in an appropriate manner when it is determined that it is not possible to appropriately perform the correction processing.

[Appendix 11]

The endoscope system according to any one of Appendices 1 to 10, wherein the reliability for a brightness value outside a certain range is lower than the reliability for a brightness value within the certain range, and the reliability varies in accordance with a disturbance including at least bleeding, fat, a residue, mucus, or a residual liquid.

[Appendix 12]

The endoscope system according to any one of Appendices 1 to 11, wherein the correction processing is either table correction processing or calculation value correction processing, the table correction processing being for correcting an oxygen saturation calculation table used to calculate the oxygen saturation based on a specific pigment concentration of the specific pigment, the calculation value correction processing being for adding or subtracting a correction value obtained from the specific pigment concentration to or from the oxygen saturation calculated based on the oxygen saturation calculation table.

[Appendix 13]

The endoscope system according to any one of Appendices 1 to 11, wherein in the correction mode, instead of the correction processing, specific oxygen saturation calculation processing for calculating the oxygen saturation in accordance with the specific pigment concentration is performed based on an oxygen-saturation image signal and the specific pigment image signal, the oxygen-saturation image signal including at least image information of a wavelength range in which an absorption coefficient changes in accordance with a change in the oxygen saturation.

[Appendix 14]

A method for operating an endoscope system including a processor, the method including:

a step of, by the processor, switching between an oxygen saturation mode for calculating an oxygen saturation of blood hemoglobin and a correction mode for displaying a correction image on a display and displaying a specific region on the display, the correction mode being a mode in which correction processing related to calculation of the oxygen saturation is performed based on a specific pigment concentration of a specific pigment other than the blood hemoglobin included in the specific region, wherein the specific pigment concentration is calculated based on a specific pigment image signal including image information of a wavelength range having sensitivity to the specific pigment, and in the correction mode, at least one of changing a display style of the correction image or changing a display style of the specific region in accordance with reliability related to the calculation of the oxygen saturation is performed.

REFERENCE SIGNS LIST

10, 100 endoscope system
12 endoscope
12*a* insertion section
12*b* operation section
12*c* bending part
12*d* tip part
12*e* angle knob
12*f* mode switch
12*h* still-image acquisition instruction switch
12*i* zoom operation unit
12*j* forceps port
13 light source device
14 processor device

15 display
16 processor-side user interface
17 extension processor device
18 extension display
19 scope-side user interface
20 light source unit
20*a* V-LED
20*b* BS-LED
20*c* BL-LED
20*d* G-LED
20*e* R-LED
21 light-source processor
23 optical path coupling unit
25 light guide
30 illumination optical system
31 imaging optical system
32 illumination lens
35 objective lens
36, 106 imaging sensor
37 imaging processor
40 CDS/AGC circuit
41 A/D converter
45 DSP
50 image processing unit
51 image communication unit
52 display control unit
53 central control unit
55*a, b, c* curve
56*a, b* curve
61 oxygen saturation image generation unit
62 specific pigment concentration calculation unit
62*a* specific pigment concentration calculation table
63 table correction unit
64 mode switching unit
65 display style control unit
66 reliability calculation unit
67 first correction determination unit
68 second correction determination unit
69 determination notification unit
70 base image generation unit
71 arithmetic value calculation unit
72 oxygen saturation calculation unit
73 oxygen saturation calculation table
74 color tone adjustment unit
80 correction image
81 specific region
82*a* low-reliability region
82*b* high-reliability region
90 two-dimensional coordinate
91 reference line
92 actual measurement line
102 broadband light source
104 rotary filter
105 filter switching unit
108 inner filter
108*a* B1 filter
108*b* G filter
108*c* R filter
109 outer filter
109*a* B1 filter
109*b* B2 filter
109*c* G filter
109*d* R filter
109*e* B3 filter
200 endoscope system
201 endoscope
202 light guide
203 camera head
205 to 207 dichroic mirror
210 to 213 imaging sensor
300 endoscope
301 color imaging sensor
302 monochrome imaging sensor
303 camera head
305 dichroic mirror
AR0 to AR4 region
DFX, DFY definition line
BF B color filter
GD operational guidance
GF G color filter
MS0, MS1, MS2 message
RF R color filter
CV0 to CV4 curved surface
EL, ELL, ELH contour

What is claimed is:

1. An endoscope system comprising:

a processor configured to:

switch between an oxygen saturation mode for calculating an oxygen saturation of blood hemoglobin and a correction mode for displaying a correction image on a display and displaying a specific region on the display, the correction mode being a mode in which correction processing related to calculation of the oxygen saturation is performed based on a specific pigment concentration of a specific pigment other than the blood hemoglobin included in the specific region, the specific pigment concentration being calculated based on a specific pigment image signal including image information of a wavelength range having sensitivity to the specific pigment; and in the correction mode, perform at least one of changing a display style of the correction image, or changing a display style of the specific region in accordance with reliability related to the calculation of the oxygen saturation, wherein the processor is further configured to:

determine whether it is possible to appropriately perform the correction processing, based on the reliability in the specific region; and make the display style of the specific region different between when it is possible to appropriately perform the correction processing and when it is not possible to appropriately perform the correction processing.

2. The endoscope system according to claim 1, wherein the processor is configured to generate a correction image with a reduced luminance of a dark portion.

3. The endoscope system according to claim 1, wherein the processor is configured to generate a correction image with saturation enhanced.

4. The endoscope system according to claim 1, wherein the processor is configured to change the display style of the correction image so that a difference between a low-reliability region in which the reliability is low and a high-reliability region in which the reliability is high is emphasized.

5. The endoscope system according to claim 4, wherein the processor is configured to set a saturation of the low-reliability region to be higher than a saturation of the high-reliability region.

6. The endoscope system according to claim 4, wherein the processor is configured to reduce a luminance of a dark portion in the low-reliability region.

7. The endoscope system according to claim 4, wherein the processor is configured to perform at least one of superimposing a region highlighting line on the low-reliability region or displaying the low-reliability region in monochrome.

8. The endoscope system according to claim 1, wherein the processor is configured to:

make a determination as to whether it is possible to appropriately perform the correction processing, based on the reliability in the specific region at a timing at which a correction operation for performing the correction processing is performed; and provide a notification related to the determination.

9. The endoscope system according to claim 8, wherein the processor is configured to provide a notification of operational guidance for performing the correction processing in an appropriate manner when it is determined that it is not possible to appropriately perform the correction processing.

10. The endoscope system according to claim 1, wherein the reliability for a brightness value outside a certain range is lower than the reliability for a brightness value within the certain range, and the reliability varies in accordance with a disturbance including at least bleeding, fat, a residue, mucus, or a residual liquid.

11. The endoscope system according to claim 1, wherein the correction processing is either table correction processing or calculation value correction processing, the table correction processing being for correcting an oxygen saturation calculation table used to calculate the oxygen saturation based on a specific pigment concentration of the specific pigment, the calculation value correction processing being for adding or subtracting a correction value obtained from the specific pigment concentration to or from the oxygen saturation calculated based on the oxygen saturation calculation table.

12. The endoscope system according to claim 1, wherein in the correction mode, instead of the correction processing, specific oxygen saturation calculation processing for calculating the oxygen saturation in accordance with the specific pigment concentration is performed based on an oxygen-saturation image signal and the specific pigment image signal, the oxygen-saturation image signal including at least image information of a wavelength range in which an absorption coefficient changes in accordance with a change in the oxygen saturation.

13. A method for operating an endoscope system including a processor, the method comprising:

a step of, by the processor, switching between an oxygen saturation mode for calculating an oxygen saturation of blood hemoglobin and a correction mode for displaying a correction image on a display and displaying a specific region on the display, the correction mode being a mode in which correction processing related to calculation of the oxygen saturation is performed based on a specific pigment concentration of a specific pigment other than the blood hemoglobin included in the specific region, wherein the specific pigment concentration is calculated based on a specific pigment image signal including image information of a wavelength range having sensitivity to the specific pigment, and in the correction mode, at least one of changing a display style of the correction image or changing a display style of the specific region in accordance with reliability related to the calculation of the oxygen saturation is performed, wherein the processor further performs:

a step of determining whether it is possible to appropriately perform the correction processing, based on the reliability in the specific region; and a step of making the display style of the specific region different between when it is possible to appropriately perform the correction processing and when it is not possible to appropriately perform the correction processing.

* * * * *